United States Patent
Ilan et al.

(10) Patent No.: US 10,087,232 B2
(45) Date of Patent: Oct. 2, 2018

(54) USE OF PLANT CELLS EXPRESSING A TNFALPHA POLYPEPTIDE INHIBITOR IN THERAPY

(71) Applicants: Protalix Ltd., Carmiel (IL); Hadasit Medical Research Services and Development Ltd., Jerusalem (IL)

(72) Inventors: Yaron Ilan, Kfar-Tavor (IL); Yoseph Shaaltiel, Timrat (IL); Uri Hanania, Carmiel (IL); Tali Kizhner, Yishuv Atzmon-Segev (IL); Tami Ariel, Misgav (IL); Svetlana Gingis-Velitski, Kiryat-Motzkin (IL)

(73) Assignees: Protalix Ltd., Carmiel (IL); Hadasit Medical Research Services and Development Ltd., Jerusalem (IL)

( * ) Notice: Subject to any disclaimer, the term of this patent is extended or adjusted under 35 U.S.C. 154(b) by 120 days.

(21) Appl. No.: 14/773,349

(22) PCT Filed: Mar. 6, 2014

(86) PCT No.: PCT/IL2014/050231
§ 371 (c)(1),
(2) Date: Sep. 6, 2015

(87) PCT Pub. No.: WO2014/136117
PCT Pub. Date: Sep. 12, 2014

(65) Prior Publication Data
US 2016/0017019 A1 Jan. 21, 2016

Related U.S. Application Data

(60) Provisional application No. 61/773,392, filed on Mar. 6, 2013.

(51) Int. Cl.
| | | |
|---|---|---|
| *A61K 39/00* | (2006.01) | |
| *A61K 38/00* | (2006.01) | |
| *A61K 38/16* | (2006.01) | |
| *C07K 14/705* | (2006.01) | |
| *C07K 14/525* | (2006.01) | |
| *C12N 15/82* | (2006.01) | |
| *A61K 9/00* | (2006.01) | |
| *A61K 36/81* | (2006.01) | |
| *C07K 16/24* | (2006.01) | |

(52) U.S. Cl.
CPC ...... *C07K 14/70578* (2013.01); *A61K 9/0053* (2013.01); *A61K 36/81* (2013.01); *C07K 14/525* (2013.01); *C07K 16/241* (2013.01); *C12N 15/8257* (2013.01); *C12N 15/8258* (2013.01); *A61K 38/00* (2013.01); *C07K 2317/14* (2013.01); *C07K 2317/76* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 7,648,702 B2 | 1/2010 | Gombotz et al. | |
| 7,901,905 B2 | 3/2011 | Frazer | |
| 7,915,225 B2 | 3/2011 | Finck | |
| 2003/0084482 A1 | 5/2003 | Hall et al. | |
| 2014/0286986 A1 | 9/2014 | Matoba et al. | |
| 2016/0017021 A1 | 1/2016 | Shaaltiel et al. | |

FOREIGN PATENT DOCUMENTS

| | | |
|---|---|---|
| CN | 1533438 | 9/2004 |
| CN | 1694958 | 11/2005 |
| WO | WO 99/67401 | 12/1999 |
| WO | WO 02/12502 | 2/2002 |
| WO | WO 02/101006 | 12/2002 |
| WO | WO 2004/024915 | 3/2004 |
| WO | WO 2012/170938 | 12/2012 |
| WO | WO 2013/087911 | 6/2013 |

OTHER PUBLICATIONS

Menassa et al. "Therapeutic Effectiveness of Orally Administered Transgenic Low-Alkaloid Tobacco Expressing Human Interleukin-10 in a Mouse Model of Colitis", Plant Biotechnology Journal, XP002725896, 5(1): 50-59, Jan. 2007.
Protalix "Study to Evaluate the Safety and Pharmacokinetics of Oral OPRX-106 (TNFR-Fc Fusion Protein) in Healthy Volunteers", ClinicalTrials.gov, Sevice of the U.S. National Institute of Health, 3 P., Last Verified Aug. 2015.
Wilson et al. "Recent Advances Towards Development and Commercialization of Plant Cell Culture Processes for the Synthesis of Biomolecules", Plant Biotechnology Journal, XP002725895, 10(3): 249-268, Apr. 2012. p. 261, 1-h Col., Last Para—p. 262, 1-h Col., Para 1, p. 262, r-h Col., Para 2, Table 1.
Winichayakul et al. "Head-to-Tail Fusions of Camelid Antibodies Can Be Expressed in Planta and Bind in Rumen Fluid", Biotechnology and Applied Biochemistry, XP002725894, 53(Pt.2): 111-122, Jun. 2009.
Official Action dated Jul. 21, 2017 From the US Patent and Trademark Office Re. U.S. Appl. No. 14/849,963. (11 pages).
Office Action dated Nov. 7, 2017 From the Israel Patent Office Re. Application No. 241151 and Its Translation Into English. (4 Pages).
Office Action dated Nov. 7, 2017 From the Israel Patent Office Re. Application No. 241221 and Its Translation Into English. (4 Pages).
Communication Pursuant to Article 94(3) EPC dated Jan. 11, 2017 From the European Patent Office Re. Application No. 14716435.4. (5 Pages).

(Continued)

*Primary Examiner* — Shulamith H Shafer

(57) ABSTRACT

A method of treating a TNF Alpha associated medical condition selected from the group consisting of obesity, metabolic syndrome, diabetes and a liver disease or disorder is provided. The method comprising enterally administering to a subject in need thereof a therapeutically effective amount of plant cells expressing a TNF Alpha polypeptide inhibitor, thereby treating the TNF Alpha associated medical condition.

24 Claims, 25 Drawing Sheets
(13 of 25 Drawing Sheet(s) Filed in Color)
Specification includes a Sequence Listing.

(56) References Cited

OTHER PUBLICATIONS

Official Action dated Jan. 25, 2017 From the US Patent and Trademark Office Re. U.S. Appl. No. 14/849,963. (14 pages).

Sedger et al. "TNF and TNF-Receptors: From Mediators of Cell Death and Inflammation to Therapeutic Giants—Past, Present and Future", Cytokine & Growth Factor Reviews 25(4): 453-472, 2014.

Chan "Plant-Made Oral Vaccines Against Human Infectious Diseases—Are we there yet?",Plant Biotechnology Journal 13(8):1056-1070, Oct. 2015.

Kwon et al. "Oral Delivery of Protein Drugs Bioencapsulated in Plant Cells", Molecular Therapy 24(8): 1342-1350, Aug. 2016.

MacEwan "Review TNF Ligands and Receptors a Matter of Life and Death", British Journal of Pharmacology, 135(4): 855-875, 2002.

No Author "Protalix Releases Preclinical Data on Anti-TNF Follow-On Biologic Arthritis Drug". Health and Beauty Close-Up. Sep. 29, 2009.

Rosales-Mendoza et al. "Immunological Aspects of Using Plant Cells as Delivery Vehicles for Oral Vaccines", Expert Review of Vaccines 13(6): 737-749, Apr. 28, 2014.

Notification of Office Action and Search Report dated Feb. 24, 2018 From the State Intellectual Property Office of the People's Republic of China Re. Application No. 201480022865.6. (8 Pages).

Translation dated Mar. 13, 2018 of Notification of Office Action dated Feb. 24, 2018 From the State Intellectual Property Office of the People's Republic of China Re. Application No. 201480022865.6. (3 Pages).

Translation dated Apr. 19, 2018 of Notice of Reason for Rejection dated Apr. 3, 2018 From the Japan Patent Office Re. Application No. 2015-560846. (9 Pages).

Advisory Action Before the Filing of an Appeal Brief dated May 22, 2018 From the US Patent and Trademark Office Re. U.S. Appl. No. 14/773,348. (5 pages).

Examination Report dated Jul. 18, 2018 From the Australian Government, IP Australia Re. Application No. 2014224174. (5 Pages).

Official Action dated Jul. 11, 2018 From the US Patent and Trademark Office Re. U.S. Appl. No. 14/773,348. (8 pages).

Translation Dated Aug. 8, 2018 of Notification of Office Action dated Aug. 1, 2018 From the State Intellectual Property Office of the People's Republic of China Re. Application No. 201480022865.6. (3 Pages).

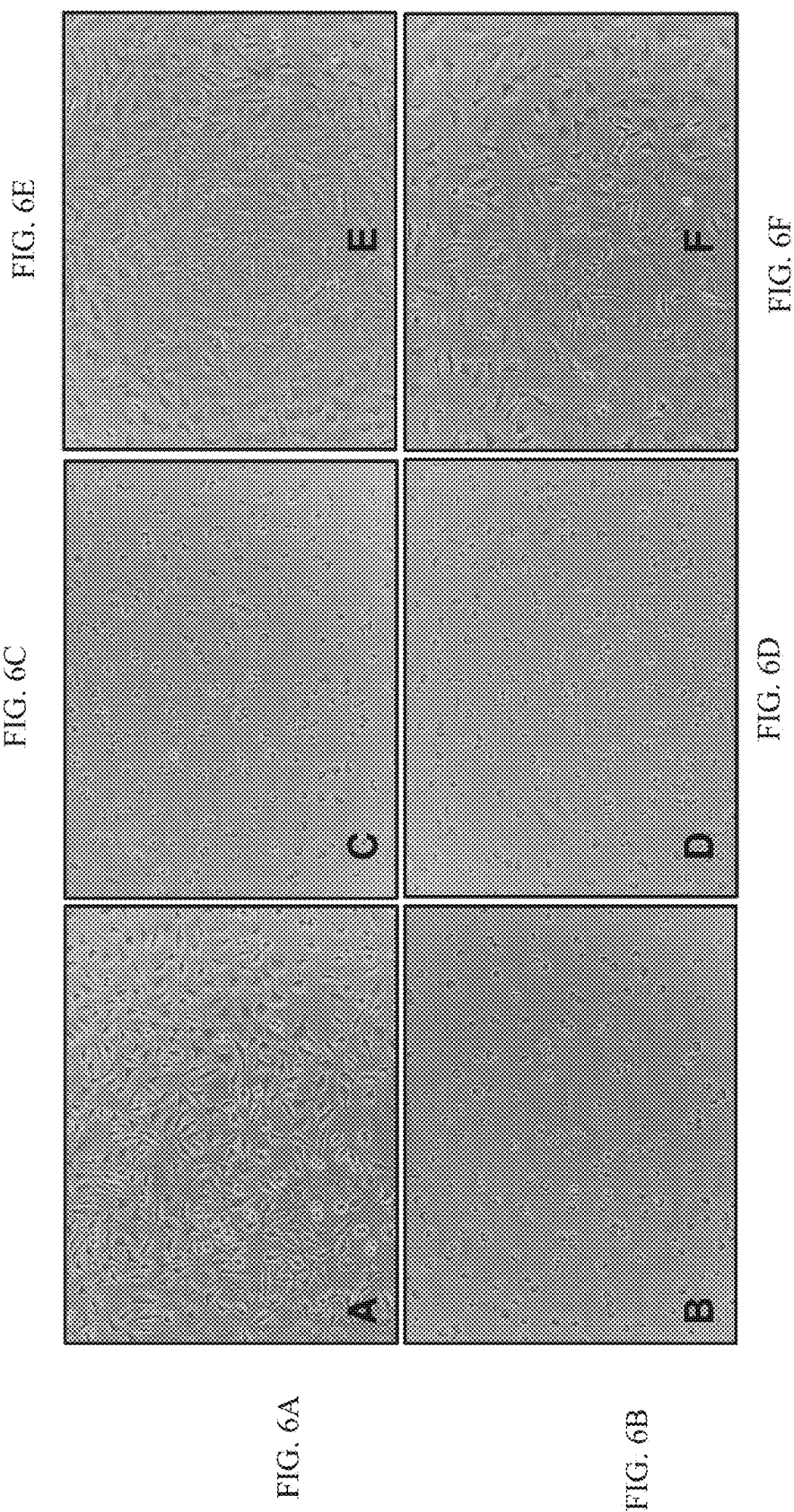

FIG. 9A
CON A +SALINE CONTROL
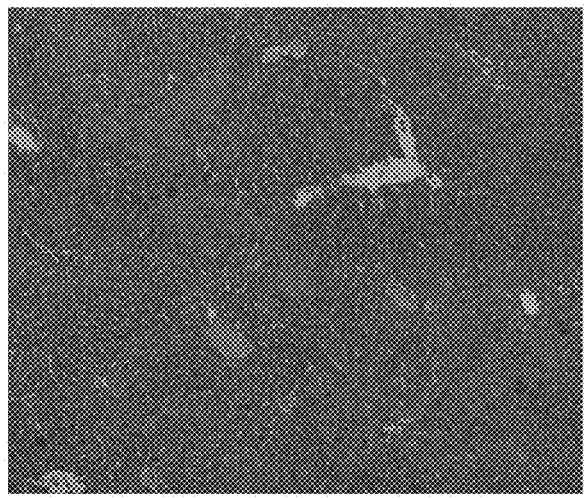
CON A + PLANT CELLS EXPRESSING RECOMBINANT TNFR:Fc 2.88 mg
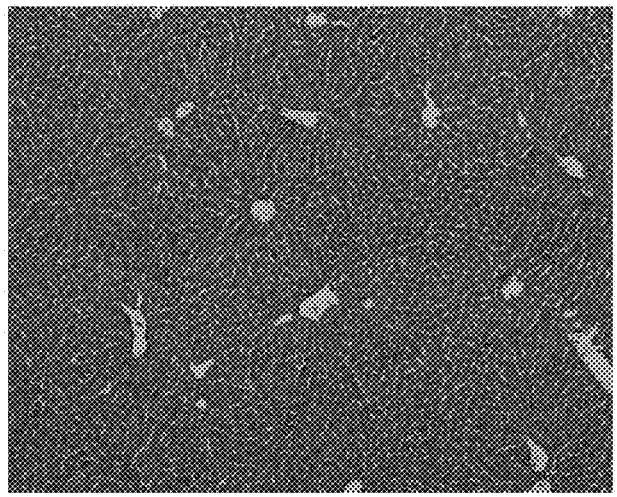
FIG. 9B

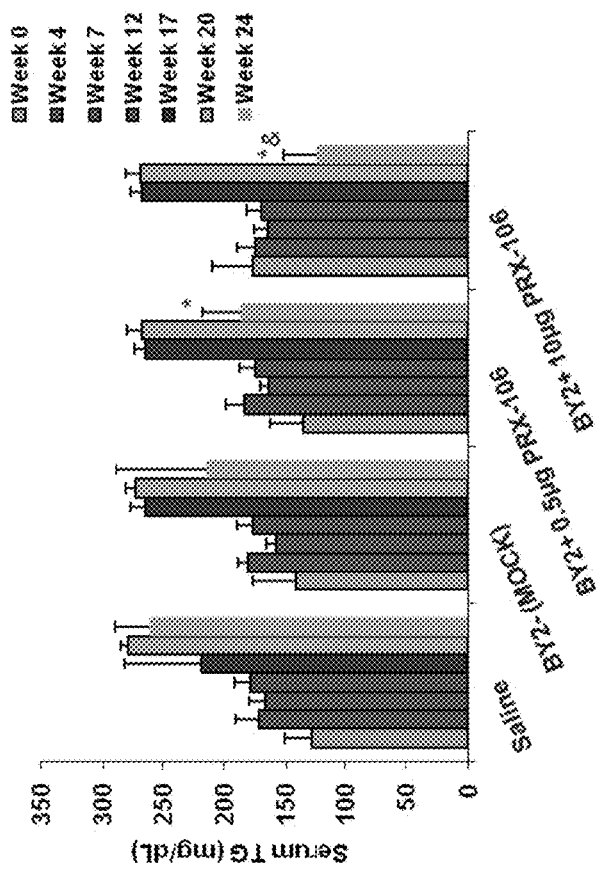
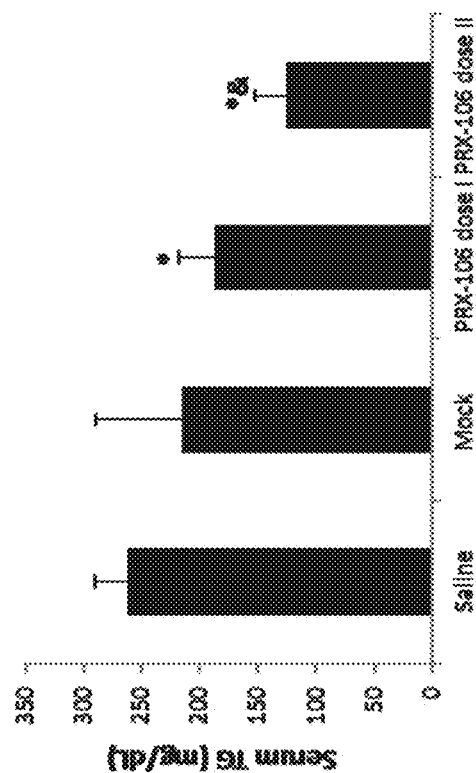
FIG. 12A
FIG. 12B

USE OF PLANT CELLS EXPRESSING A TNFALPHA POLYPEPTIDE INHIBITOR IN THERAPY

RELATED APPLICATIONS

This application is a National Phase of PCT Patent Application No. PCT/IL2014/050231 having International filing date of Mar. 6, 2014, which claims the benefit of priority under 35 USC § 119(e) of U.S. Provisional Patent Application No. 61/773,392 filed on Mar. 6, 2013. The contents of the above applications are all incorporated by reference as if fully set forth herein in their entirety.

SEQUENCE LISTING STATEMENT

The ASCII file, entitled 63847SequenceListing.txt, created on Aug. 19, 2015, comprising 86,872 bytes, submitted concurrently with the filing of this application is incorporated herein by reference.

FIELD AND BACKGROUND OF THE INVENTION

The present invention, in some embodiments thereof, relates to the use of plant cells expressing a TNFalpha polypeptide inhibitor in therapy.

Tumor necrosis factor alpha (TNFα) is an important, pro-inflammatory cytokine mediating the regulation of diverse inflammatory, infectious and immune-related processes and diseases, TNFα being considered the most important mediator responsible for inflammatory pathology.

TNF-alpha is a 17 kD molecular weight protein, initially synthesized as a transmembrane protein arranged in stable trimers, then cleaved by metalloprotease-TNF alpha converting enzyme (TACE) to form the homotrimeric soluble TNF (sTNF) which engages to its cognate receptors (TNFRI, p55 and TNFRII, p75), expressed ubiquitously. The ubiquitous TNF receptors provides the basis for the wide variety of TNF-alpha mediated cellular responses.

TNF-alpha induces a wide variety of cellular responses, many of which result in deleterious consequences, such as cachexia (loss of fat and whole body protein depletion, leading to anorexia, common in cancer and AIDS patients) and septic shock. Elevated secretion of TNF-alpha has been implicated in a variety of human diseases including diabetes, allograft rejection, sepsis, inflammatory bowel diseases, osteoporosis, in many autoimmune diseases such as multiple sclerosis, rheumatoid arthritis, psoriasis, psoriatic arthritis, hypersensitivity, immune complex diseases, and even in malaria, cancer and lung fibrosis.

The biological effect of TNFα is mediated by the two distinct receptors. TNF-alpha receptors, when shed from mononuclear cells, lower the TNF-alpha levels by "mopping up" and acting as natural inhibitors Neutralization of TNFα by specific antibodies and decoy receptors has become a common strategy for regulation of TNFα mediated toxicity.

To date, five protein-based TNFα antagonists have been approved by the US FDA for clinical use: Cimzia (Certolizumab pegol), a TNFmAb Fab' fragment—PEG conjugate; Remicade (Infliximab), a TNF rmAB; Humira (Adalimumab, a TNF rmAB, Simponi™ (Golimumab), an anti-TNF and etanercept, a fusion protein of soluble 75 kDa TNFα receptors fused to the Fc fragment of human IgG (registered as Enbrel™).

Etanercept is indicated for rheumatoid arthritis (RA) and other arthritic indications such as juvenile idiopathic arthritis (JIA), psoriasis and Ankylosing Spondylitis (AS). Rheumatoid arthritis (RA) is a chronic disease that affects approximately five million people World Wide. Nearly 500,000 patients worldwide across indications are treated with Enbrel. Enbrel sales in 2010 were 7.8 billion dollars and the total anti-TNF market amounted to 24.04 Billion dollars. Clinical trials of Enbrel therapy, current or completed, include such diverse indications as adult respiratory distress syndrome, pemphigus, Alzheimer's disease, Behcet's syndrome, HIV, myocardial infarct, knee joint synovitis, lupus nephritis, lichen planus, systemic amyloidosis, sciatica, vitiligo, chronic fatigue syndrome, anorexia, TMJ, asthma, bronchitis, diabetes, myelodysplastic disease and others.

Biopharmaceuticals typically pose a number of challenges, however, that drug developers must overcome in order to successfully develop these compounds into safe and effective therapeutics. For example, proteins and peptides tend to be destroyed by proteolytic enzymes or, in the case of the higher molecular weight proteins, may generate neutralizing antibodies. Moreover, large complex molecules can exhibit low solubility or poor stability, leading to short shelf lives. As a result, biopharmaceutical therapeutics often quickly lose their effectiveness or require frequent dosing. These factors impact not only cost of therapy, but also patient acceptance and compliance, thus affecting their therapeutic efficacy.

Oral Administration:

The most common mode of protein and peptide-based administration is by invasive methods of drug delivery, such as injections and infusions. Although these are the primary modes for administering macromolecular drugs for systemic diseases, they are also the least desirable for patients and practitioners. The obvious downside of this delivery method is patient acceptance and compliance, limiting most macromolecule development to indications in which the need to use invasive administration routes are not outweighed by associated expenses or inconvenience. As a simple, non-invasive method for systemically delivering drugs, oral administration provides many advantages: ease and convenience of use, access to extensive volume of absorptive surface, high degree of vascularization, relatively lengthy retention time, natural disposal of inactive, non-metabolized ingredients, and more.

Nonetheless, investigations of oral administration of macromolecular pharmaceuticals have not indicated satisfactory levels of efficiency to match the potential of this route. Some of the obstacles are difficulties of ingestion of pills and other solid formulations, lability of biologically active macromolecules in the GI tract, concentration of the biologically active agents at the mucosa, and permeability of GI membranes to biologically active macromolecules.

The oral route of administration of biologically active substances is complicated by both high acidity and enzymatic degradation in the stomach, which can inactivate or destroy biologically active macromolecules before they reach their intended target tissue. Further, effective concentrations of a biologically active macromolecule are difficult to achieve in the large volumes encountered in the GI tract. Thus, to be effective, most drugs must be protected from absorption and/or the environment in the upper GI tract, and then be abruptly released into the intestine or colon. Various strategies are being developed in the pharmaceutical industry to overcome the problems associated with oral or enteral administration of therapeutic macromolecules such as proteins. These strategies include covalent linkage with a carrier, coatings and formulations (pH sensitive coatings, polymers and multi-layered coatings, encapsulation, timed release formulations, bioadhesives systems, osmotic controlled delivery systems, etc) designed to slow or prevent release of active ingredients in harsh conditions such as the stomach and upper GI tract. However, preparation of biologically active agents in such formulations requires complex and costly processes. Also employed are mucosal adhesives and penetration enhancers (salicylates, lipid-bile salt-mixed micelles, glycerides, acylcarnitines, etc) for increasing uptake at the mucosa. However, some of these can cause serious local toxicity problems, such as local irritation, abrasion of the epithelial layer and inflammation of tissue. Other strategies to improve oral delivery include mixing the biologically active agent with protease inhibitors, such as aprotinin, soybean trypsin inhibitor, and amastatin; however, enzyme inhibitors are not selective, and also inhibit endogenous macromolecules, causing undesirable side effects. Thus, present methods of oral administration of biologically active biopharmaceuticals cannot ensure efficient delivery of desired biological activity at the target tissue. Attempts at orally administering TNFR2:Fc (Enbrel) have failed to due to the high acidity and enzymatic degradation in the stomach that inactivates or destroys the molecule before reaching the circulation. Elaborate, complicated mechanisms, including devices for automatic parenteral administration have evolved to ensure compliance with dosage regimens.

Additional background art includes: U.S. Pat. No. 7,915,225 to Finck et al, U.S. patent application Ser. Nos. 13/021,545 and 10/853,479 to Finck et al, U.S. patent application Ser. No. 11/906,600 to Li et al, U.S. patent application Ser. No. 10/115,625 to Warren et al and U.S. patent application Ser. No. 11/784,538 to Gombotz et al.

SUMMARY OF THE INVENTION

According to an aspect of some embodiments of the present invention there is provided a method of treating a TNFα associated medical condition selected from the group consisting of obesity, metabolic syndrome, diabetes and a liver disease or disorder, the method comprising enterally administering to a subject in need thereof a therapeutically effective amount of plant cells expressing a TNFα polypeptide inhibitor, thereby treating the TNFα associated medical condition.

According to an aspect of some embodiments of the present invention there is provided a use of plant cells expressing a TNFα polypeptide inhibitor for the enteral treatment of a TNFα associated medical condition selected from the group consisting of obesity, metabolic syndrome, diabetes and a liver disease or disorder.

According to some embodiments of the invention, the enteral is oral administration.

According to some embodiments of the invention, the TNFα polypeptide inhibitor is an anti-TNFα antibody.

According to some embodiments of the invention, the anti-TNFα antibody is infliximab, adalimumab or golimumab.

According to some embodiments of the invention, the TNFα polypeptide inhibitor is a chimeric polypeptide comprising:
(i) a first domain which comprises a TNFα binding domain of a TNF receptor; and
(ii) a second domain which comprises an Fc domain of an immunoglobulin, wherein the first domain and the second domain are N-terminally to C-terminally respectively sequentially translationally fused and wherein the chimeric polypeptide specifically binds TNFα.

According to some embodiments of the invention, the chimeric polypeptide further comprises a third domain which comprises an endoplasmic reticulum retention signal, wherein the first domain, second domain and third domain are N-terminally to C-terminally respectively sequentially translationally fused.

According to some embodiments of the invention, the method or use comprising an additional domain encoding an endoplasmic reticulum signal peptide translationally fused N-terminally to the first domain.

According to some embodiments of the invention, the signal peptide is a plant signal peptide.

According to some embodiments of the invention, the plant signal peptide is as set forth in SEQ ID NO: 4.

According to some embodiments of the invention, the first domain is 200-250 amino acids long.

According to some embodiments of the invention, the first domain comprises the amino acid sequence LCAP (SEQ ID NO: 11) and VFCT (SEQ ID NO: 12).

According to some embodiments of the invention, the first domain further comprises the amino acid sequence LPAQVAFXPYAPEPGSTC (SEQ ID NO: 13).

According to some embodiments of the invention, the first domain is as set forth in SEQ ID NO: 2.

According to some embodiments of the invention, the immunoglobulin is IgG$_1$.

According to some embodiments of the invention, the second domain is as set forth in SEQ ID NO: 9.

According to some embodiments of the invention, the chimeric polypeptide is as set forth in SEQ ID NO: 6.

According to some embodiments of the invention, the chimeric polypeptide is as set forth in SEQ ID NO: 7, 204 or 205.

According to some embodiments of the invention, the chimeric polypeptide is capable of inhibiting TNFα-induced apoptosis.

According to some embodiments of the invention, the TNFα polypeptide inhibitor comprises a plant-specific glycan.

According to some embodiments of the invention, the plant-specific glycan is selected from the group consisting of a core xylose and a core α-(1,3) fucose. According to some embodiments of the invention, the plant cells are *Nicotiana tabacum* plant cells.

According to some embodiments of the invention, the *Nicotiana tabacum* plant cell is a Bright Yellow (BY-2) cell.

According to some embodiments of the invention, the plant cells are lyophilized.

According to some embodiments of the invention, the plant cells are grown in suspension.

According to some embodiments of the invention, the liver disease or disorder is selected from the group consisting of hepatitis, liver cirrhosis, liver cancer, hepatotoxicity, chronic liver disease, fatty liver disease and non-alcoholic steatohepatitis (NASH).

According to some embodiments of the invention, the hepatotoxicity is induced by a chemical agent selected from the group consisting of acetaminophen, NTHES, glucocorticoid, isniazed, arsenic, carbon tetrachloride and vinyl chloride.

According to some embodiments of the invention, the diabetes is selected from the group consisting of type I diabetes, type II diabetes and LADA disease.

According to some embodiments of the invention, the plant cells are provided in an oral nutritional form.

According to some embodiments of the invention, the oral nutritional form is a complete meal, a powder for dissolution, a bar, a baked product, a cereal bar, a dairy bar, a snack-food, a breakfast cereal, muesli, candies, tabs, cookies, biscuits, crackers, chocolate, and dairy products.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
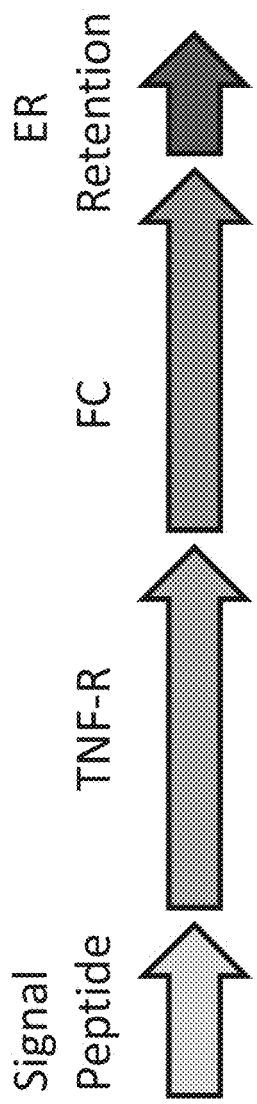
Figures 2A, 2B:
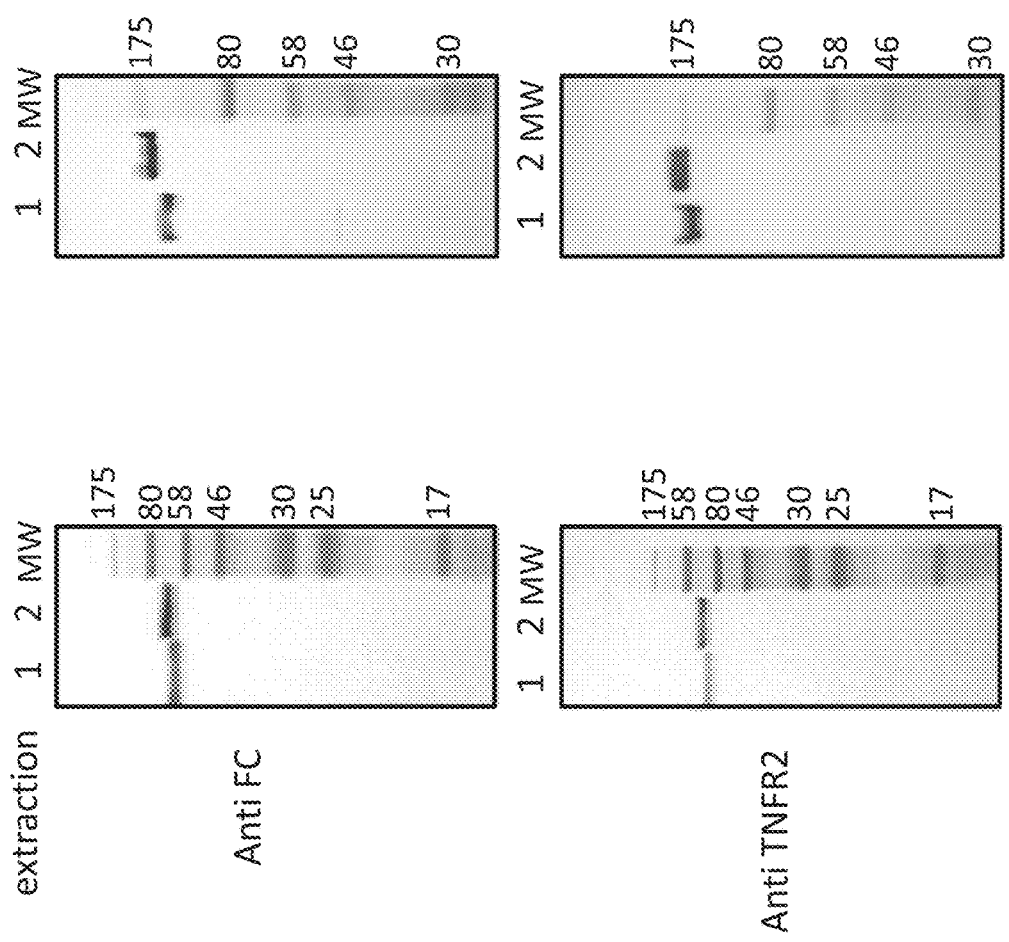
Figure 3:
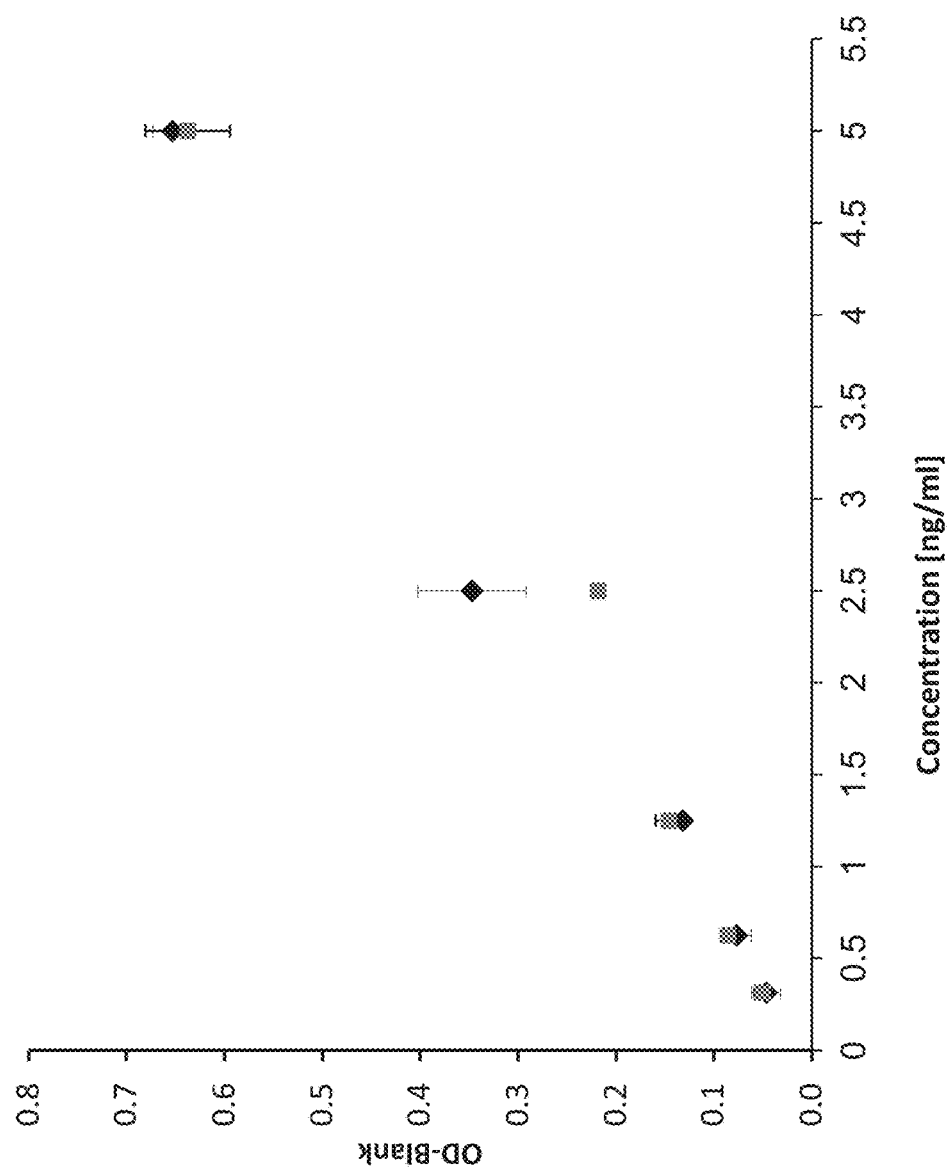
Figure 4:
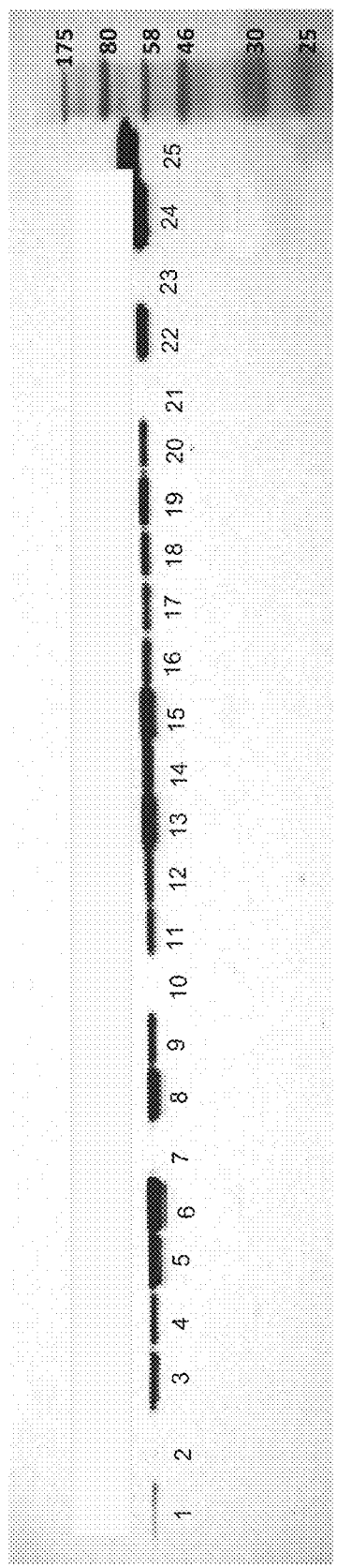
Figures 5A, 5B, 5C, 5D, 5E, 5F:
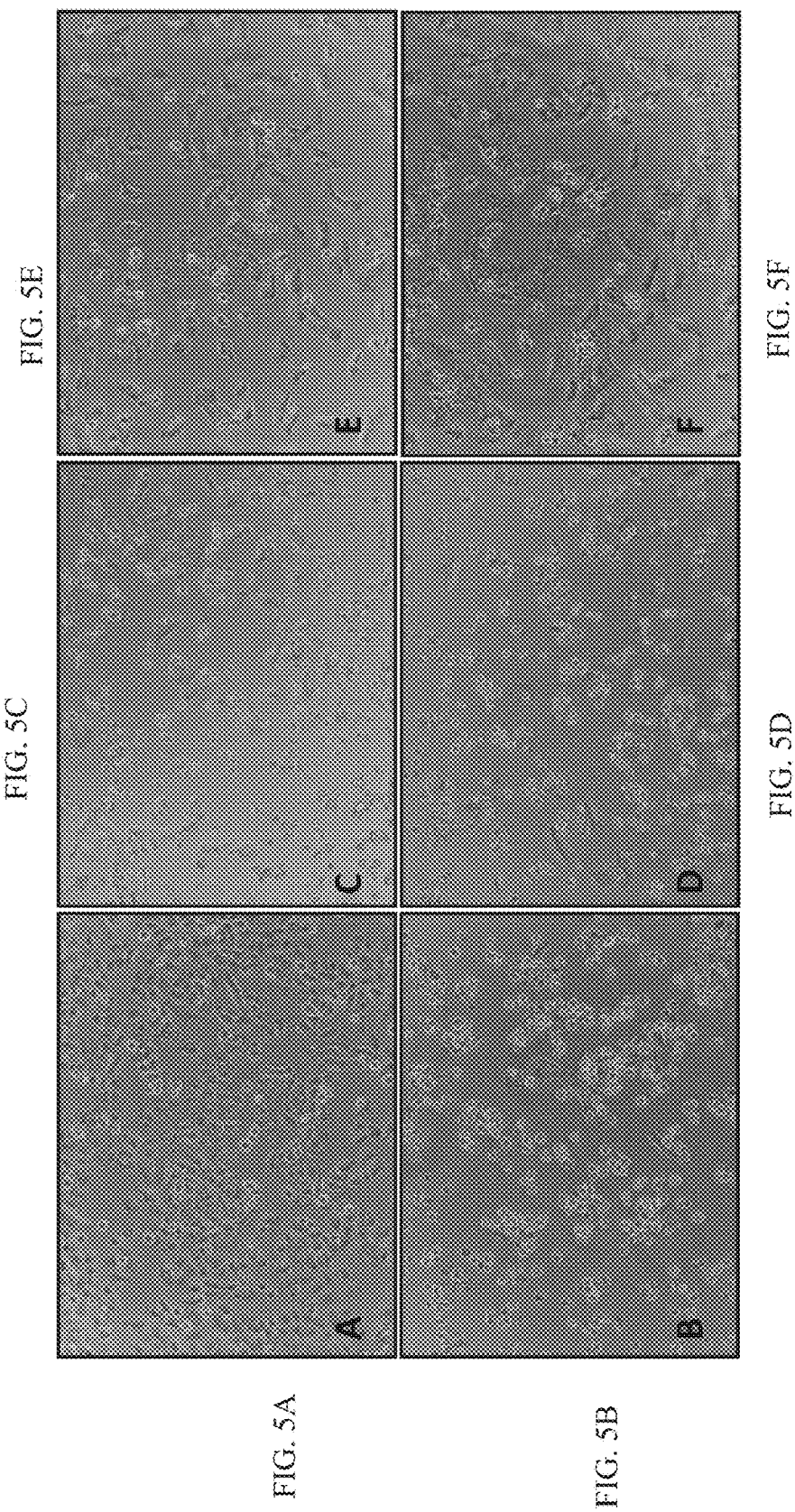
Figure 5G:
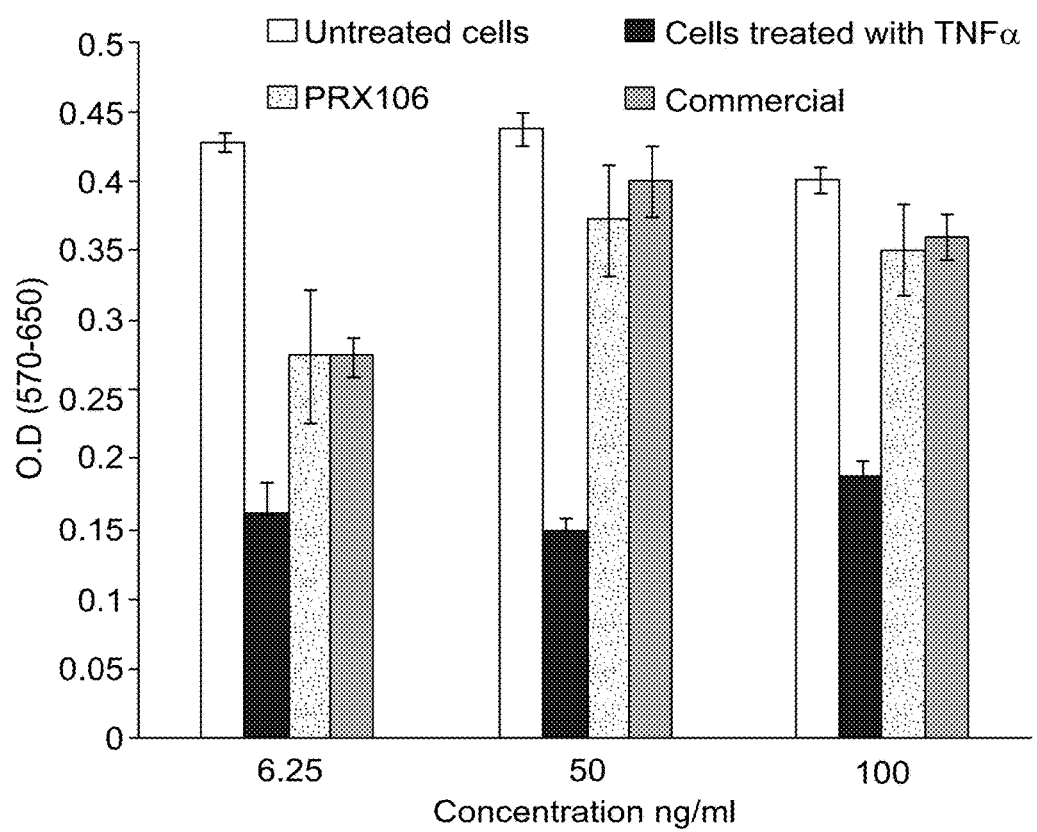
Figure 6G:
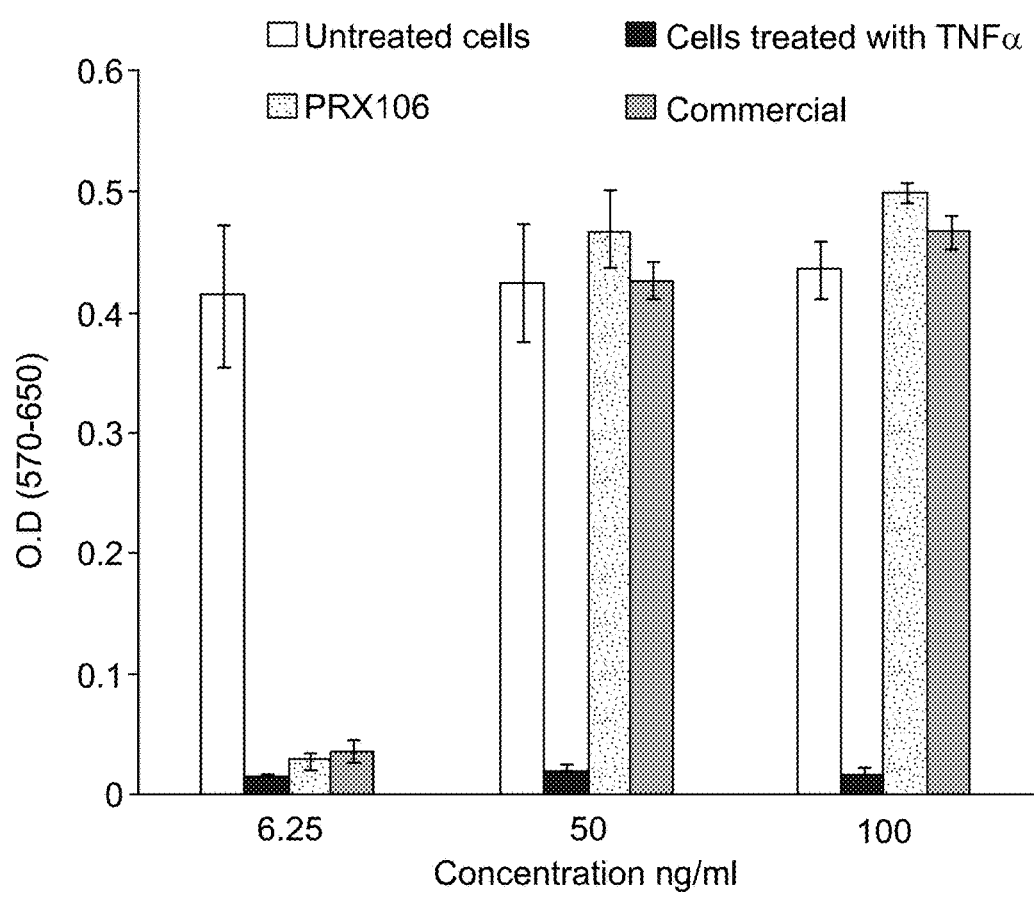
Figure 7A:
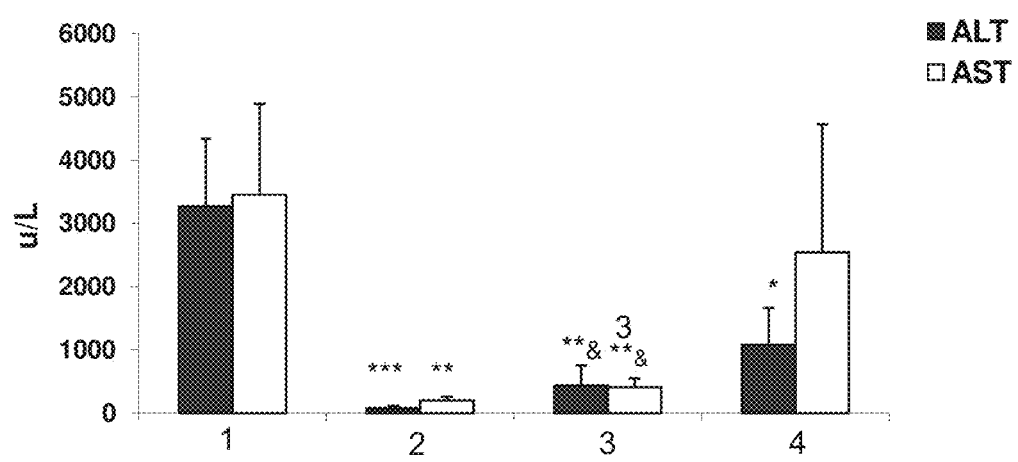
Figure 7B:
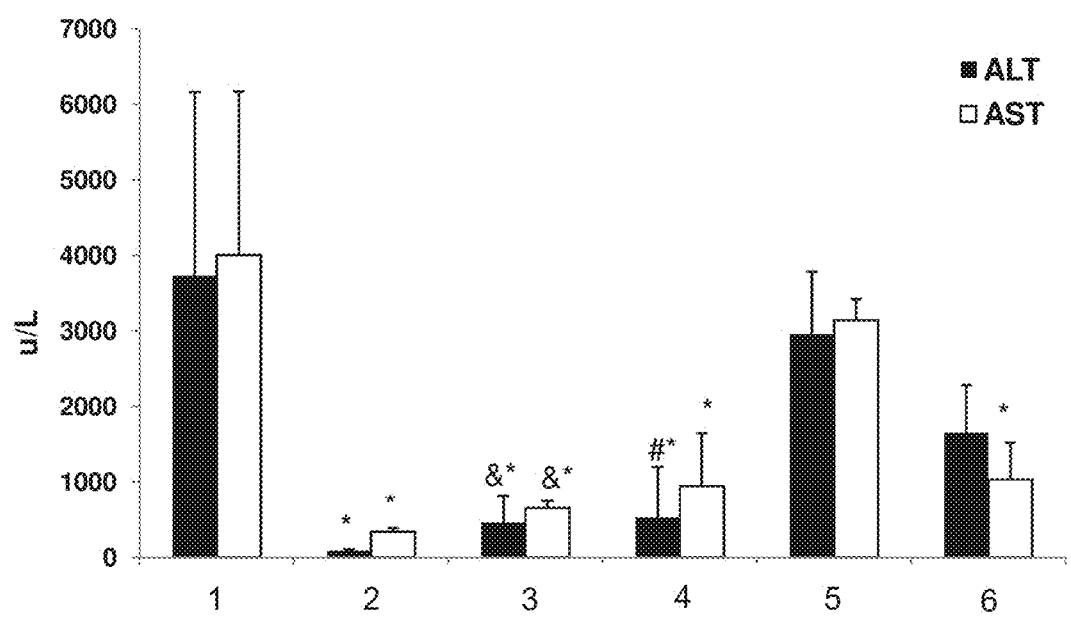
Figure 7C:
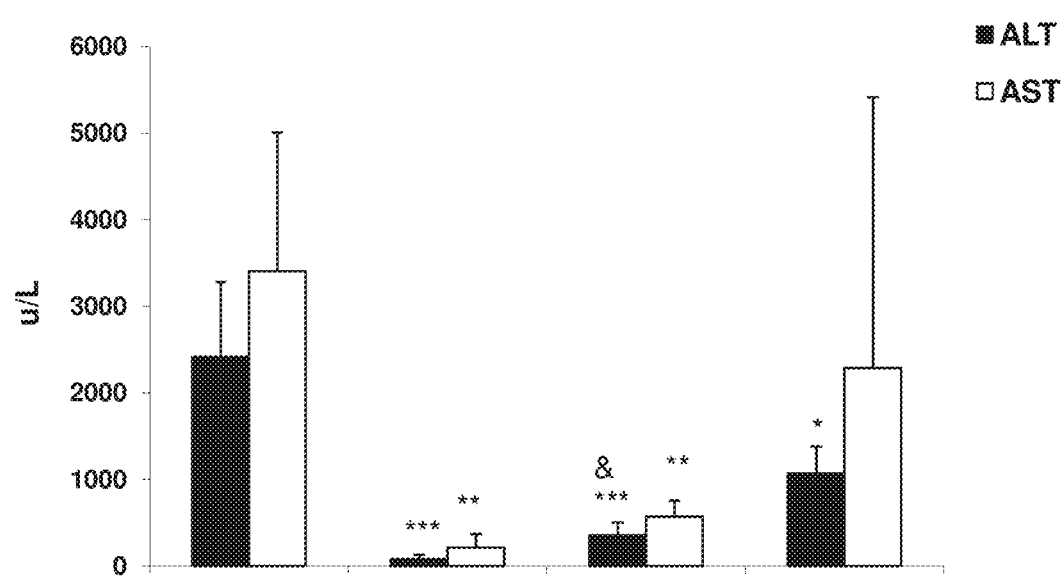
Figure 8A:
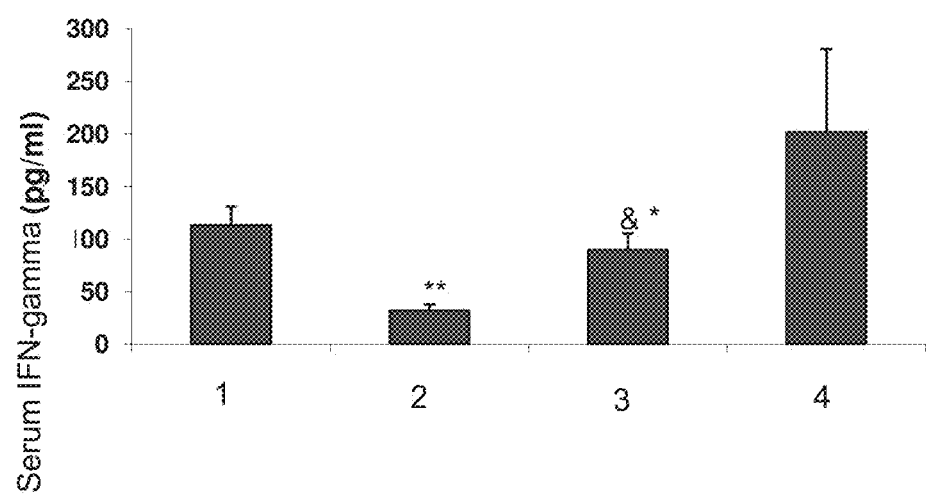
Figure 8B:
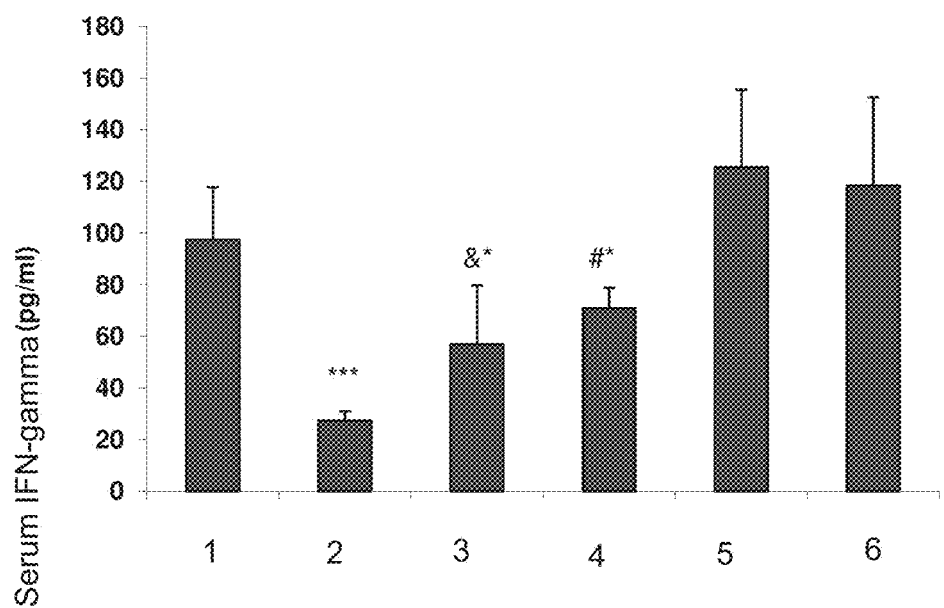
Figure 8C:
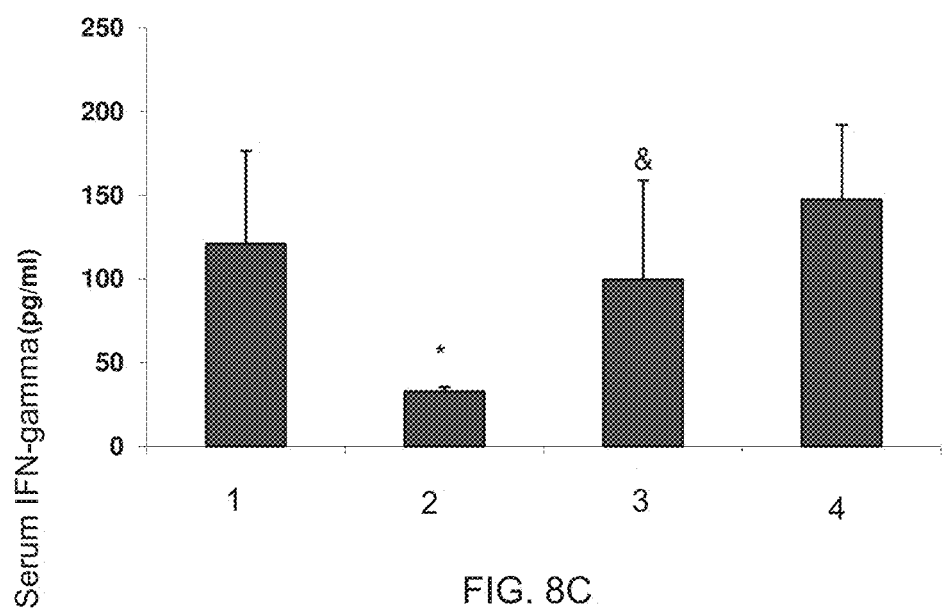
Figure 9C:
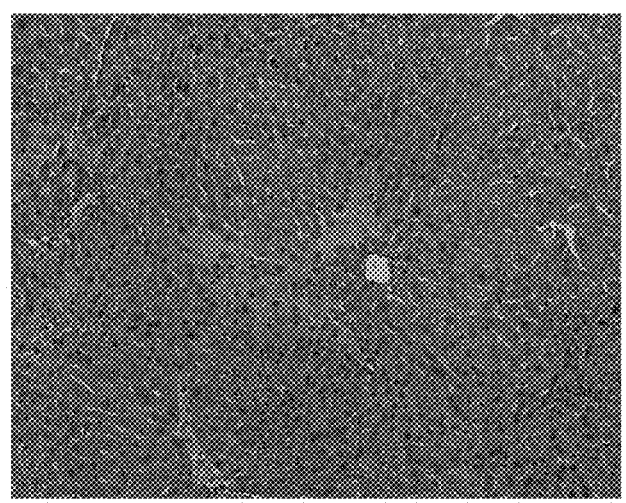
Figure 10A:
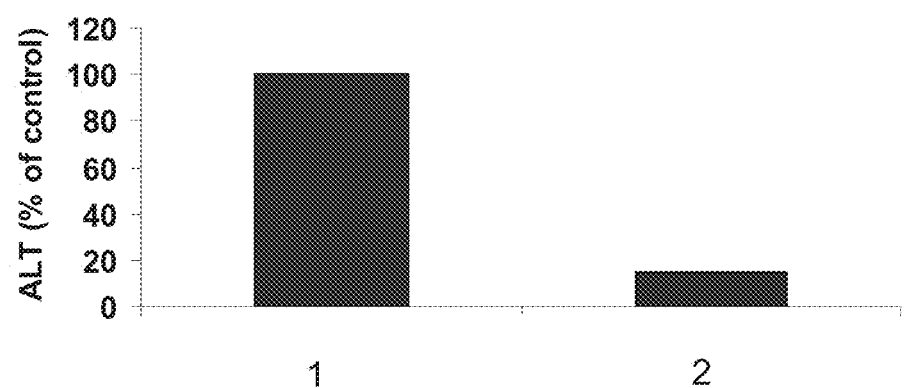
Figure 10B:
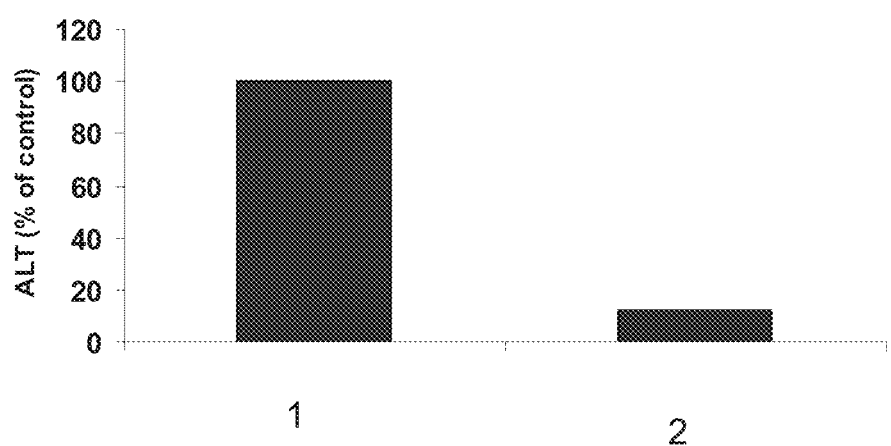

FIG. 1 is a schematic illustration of the amino acid sequence of plant expressed recombinant human (prh) TNFR2:Fc (also termed herein PRX-106, SEQ ID NO:6). prh TNFR2:Fc cDNA for expression in BY2 cells was assembled with a signal peptide for targeting the fusion polypeptide composed of the TNF-binding moiety of the TNF receptor and FC protein to the secretory pathway. Colour code for the amino acid sequence: Yellow: signal peptide; Black: TNF receptor portion; Blue: Fc portion of IgG1; Red: ER retention signal;

FIGS. 2A-B show a comparison of PRH TNFR2:FC and commercial Enbrel® by Western-blot. Prh TNFR2:Fc (lane 1) and commercial Enbrel (lane 2) were analyzed under reducing conditions (FIG. 2A) and non-reducing conditions (FIG. 2B) by 12% and 8% Tris-Glycine SDS-PAGE, respectively. Membranes were blotted with an anti human IgG (antiFC) antibody (upper panel) and with an anti TNFR2 antibody (lower panel). Molecular weight marker is shown in right lanes. Lane 1: PRH TNFR2:FC; Lane 2: commercial Enbrel®;

FIG. 3 is a graph showing TNFα binding by prh TNFR2:Fc and commercial Enbrel® by quantitative non radioactive assay for prh TNFR2:Fc binding activity and molecular integrity. An ELISA plate pre-coated with antibodies against TNFα, was incubated with TNFα followed by exposure to commercial Enbrel® and supernatant from BY2 cells expressing prh TNFR2:Fc. Serial dilutions of both preparations are shown in the X axis. Fc portion of the molecule was detected with Goat anti human IgG Fc HRP;

FIG. 4 is an image showing screening of individual plant cell lines for expression of prh TNFR2:Fc by Western blot analysis with anti-IgG (anti-Fc) antibody;

FIGS. 5A-F are images showing TNFα cytotoxicity in A375 cells in the presence of prh TNFR2:Fc or commercial Enbrel® by MTT viability assay. FIG. 5A—untreated cultured A375 cells; FIG. 5B—treated with TNFα; FIG. 5C—TNFα exposed cells treated with prh TNFR2:Fc (3.125 ng/ml); FIG. 5D—TNFα exposed cells treated with commercial Enbrel® (3.125 ng/ml); FIG. 5E—TNFα exposed cells treated with prh TNFR2:Fc (100 ng/ml); FIG. 5F—TNFα exposed cells treated with commercial Enbrel® (100 ng/ml);

FIG. 5G is a bar graph showing TNFα cytotoxicity in A375 cells in the presence of prh TNFR2:Fc or commercial Enbrel by MTT viability assay;

FIGS. 6A-F are images showing TNFα cytotoxicity in L929 cells in the presence of prh TNFR2:Fc or commercial Enbrel® by MTT viability assay. FIG. 6A—untreated cultured L929 cells; FIG. 6B—treated with TNFα; FIG. 6C—TNFα exposed cells treated with prh TNFR2:Fc (3.125 ng/ml); FIG. 6D—TNFα exposed cells treated with commercial Enbrel® (3.125 ng/ml); FIG. 6E—TNFα exposed cells treated with prh TNFR2:Fc (100 ng/ml); FIG. 6F—TNFα exposed cells treated with commercial Enbrel® (100 ng/ml);

FIG. 6G is a bar graph showing are images showing TNFα cytotoxicity in L929 cells in the presence of prh TNFR2:Fc or commercial Enbrel® by MTT viability assay;

FIGS. 7A-C are bar graphs illustrating the effective anti-inflammatory activity of plant cells expressing recombinant TNFR2:Fc on serum markers of hepatotoxicity in the concanavalin A (Con A) mouse immune mediated hepatitis model. Mice received plant cells expressing recombinant TNFR2:Fc (plant TNFR2:Fc), steroid anti-inflammatory treatment (Dexamethasone), host plant control cells (BY2) or no treatment (Saline) 6 hours prior to i.v. administration of concanavalin A (Con A). 14 hours after con A administration serum liver enzymes (alanine aminotranferase ALT and aspartate aminotransferase AST) were assayed to assess extent of liver parenchymal damage. FIGS. 7A and 7C—column 1—saline control; column 2—Dexamethasone; column 3—plant cells expressing recombinant TNFR2:Fc equivalent to 5 μg TNFR2:Fc protein; column 4—equivalent volume host plant control cells (BY2). FIG. 7B—column 1—saline control; column 2—Dexamethasone; column 3—plant cells expressing recombinant TNFR2:Fc equivalent to 0.5 μg TNFR2:Fc protein; column 4—plant cells expressing recombinant TNFR2:Fc equivalent to 5 μg TNFR2:Fc protein; column 5—host plant control cells (BY2) equivalent volume to column 3; column 6—host plant control cells (BY2) equivalent volume to column 4. FIG. 7A—n=6, *p<0.01; p<0.0005; *p<0.00005, relative to saline & p<0.05, relative to negative control. FIG. 7B—n=6, *p<0.02; relative to saline, & p<0.0005, relative to negative control, # p<0.03, relative to negative control. FIG. 7C—n=6, *p<0.01; p<0.0005; *p<0.00005, relative to saline, & p<0.00005, relative to negative control;

FIGS. 8A-8C are bar graphs illustrating the effective anti-inflammatory activity of oral administration of plant cells expressing recombinant TNFR2:Fc on serum IFN-gamma levels in the concanavalin A (Con A) mouse immune-mediated hepatitis model. Mice received oral administration of plant cells expressing recombinant TNFR2:Fc, host plant control cells (BY2), steroid or saline prior to administration of Con A as described in FIGS. 7A-7C. 14 hours after con A administration serum INF-gamma was assayed by ELISA. FIGS. 8A and 8C—column 1—saline control; column 2—Dexamethasone; column 3—plant cells expressing recombinant TNFR2:Fc equivalent to 5 μg TNFR2:Fc protein; column 4—host plant control cells (BY2) equivalent volume. FIG. 8B—column 1—saline control; column 2—Dexamethasone; column 3—plant cells expressing recombinant TNFR2:Fc equivalent to 0.5 μg TNFR2:Fc protein; column 4—plant cells expressing recombinant TNFR2:Fc equivalent to 5 μg TNFR2:Fc protein; column 5—host plant control cells (BY2) equivalent to column 3; column 6—host plant control cells (BY2) equivalent to column 4. FIG. 8A—n=6, *p<0.05; **p<0.00001, relative to saline, & p<0.0004, relative to negative control. FIG. 8B—n=6, *p<0.05; **p<0.00001, relative to saline, & p<0.004, relative to negative control, # p<0.02, relative to negative control. FIG. 8C—n=6, *p<0.05, relative to saline, & p<0.09, relative to negative control;

FIGS. 9A-9C are photomicrographs of exemplary liver slices illustrating prevention of hepatotoxicity by oral administration of plant cells expressing recombinant TNFR2:Fc in the mouse concanavalin A (Con A) immune-mediated hepatitis model. Mice received plant cells expressing recombinant TNFR2:Fc, host plant control cells (BY2), or saline prior to administration of Con A as described in FIGS. 6A-6C. 14 hours after con A administration livers were excised, fixed in formaldehyde, sectioned and stained with hematoxylin and evaluated by light microscopy. FIG. 9A—Con A+saline (control). FIG. 9B—Con A+plant cells expressing recombinant TNFR2:Fc equivalent to 0.5 μg TNFR2:Fc protein. FIG. 9C—Con A+mass of host plant control BY2 cells (BY2) equivalent to FIG. 9B; and FIGS. 10A and 10B are bar graphs illustrating the effective anti-inflammatory activity of orally administered plant cells expressing recombinant TNFR2:Fc on serum markers of hepatotoxicity in the concanavalin A (Con A) mouse immune-mediated hepatitis model, as compared to that of mammalian recombinant cell-produced TNFR2:Fc. Mice received plant cells expressing recombinant TNFR2:Fc (plant TNFR2:Fc) equivalent to 5 μg TNFR2:Fc protein, administered orally (FIG. 10A, column 2), 0.1 mg mammalian recombinant TNFR2:Fc (Etanercept), administered intraperitoneally (FIG. 9B, column 2) or control treatment (FIGS. 10A and 10B, column 1), 6 hours prior to i.v. administration of concanavalin A (Con A). 14 hours after con A administration serum liver biochemistry marker alanine aminotranferase (ALT) was assayed to assess extent of liver parenchymal damage. FIG. 10A—n=6, *p<0.01; p<0.0005; *p<0.00005, relative to saline & p<0.05, relative to negative control. Note the equivalent anti-inflammatory effect of the orally administered plant cells expressing recombinant TNFR2:Fc to that of 0.1 mg mammalian recombinant TNFR2:Fc fusion protein (Etanercept) administered i.p.

Figure 11:
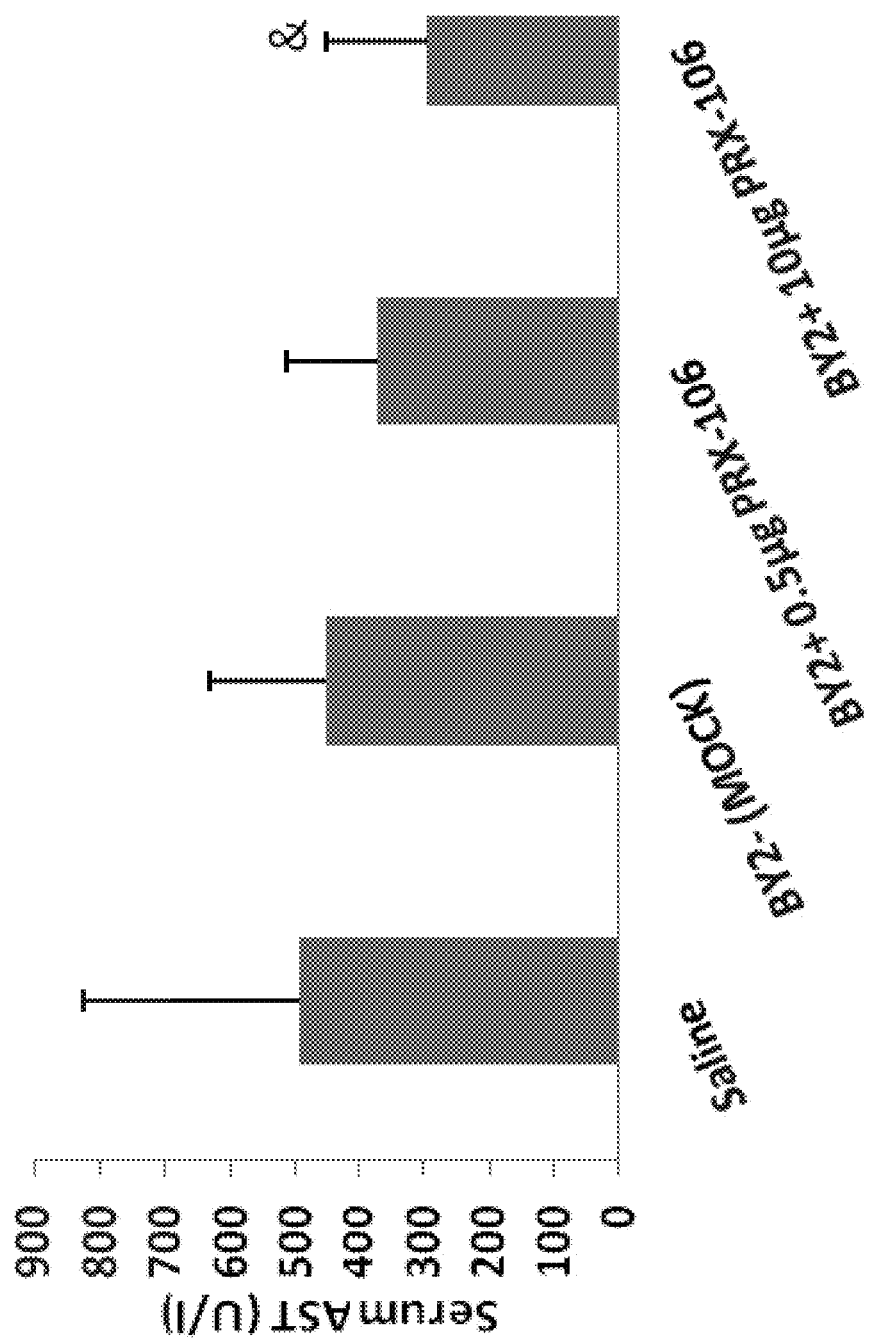

FIG. 11 is a bar graph showing the effect of oral administration of recombinant TNFR2:Fc in plant cells on serum levels in high fat diet mouse model.

FIGS. 12A-B are bar graphs showing the effect of oral administration of recombinant TNFR2:Fc in plant cells on serum TGs in high fat diet mouse model. *p<0.0001, compared to saline; &, p<0.002, compared to mock.

Figure 13:
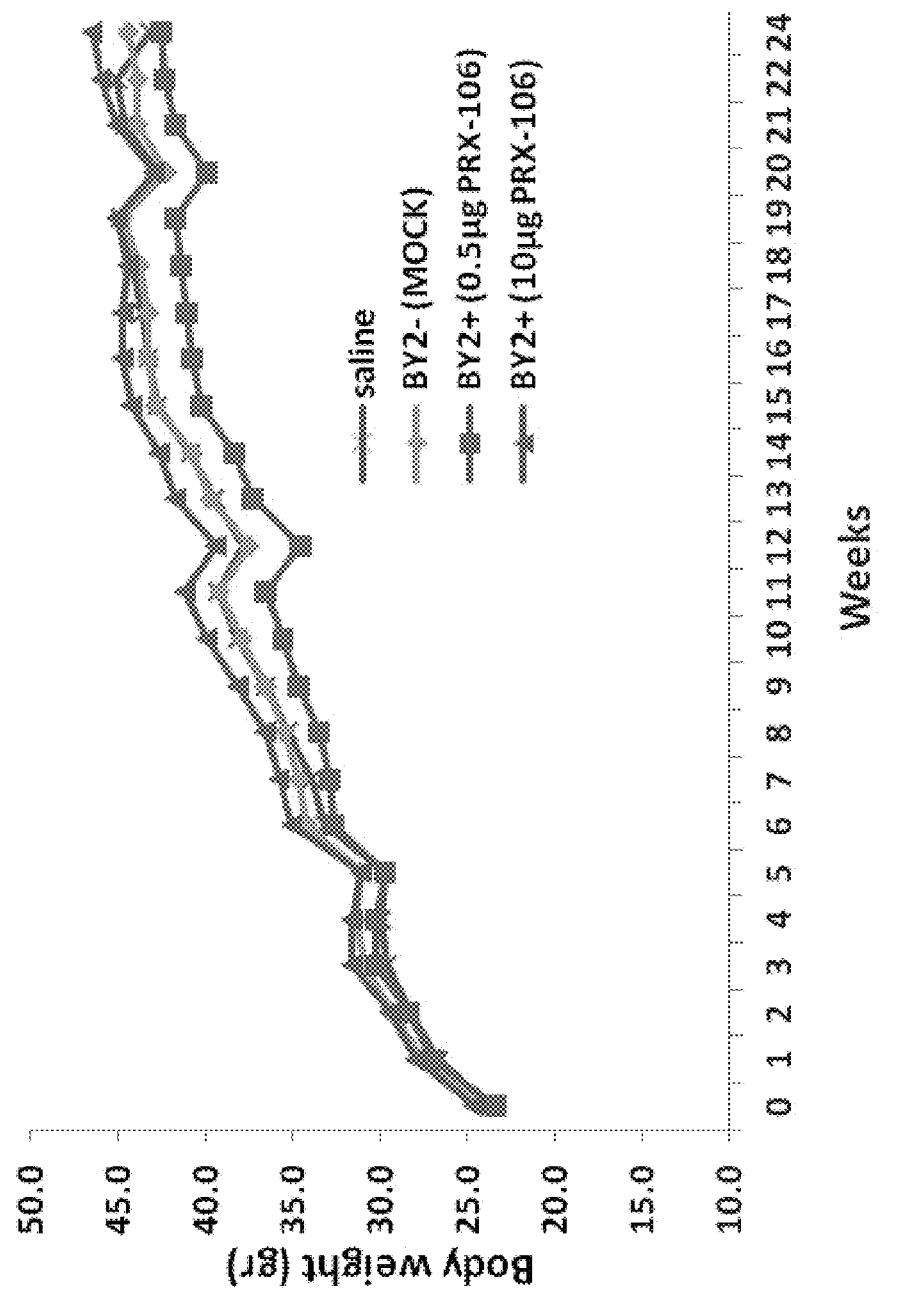

FIG. 13 is a graph showing weight gain in HFD mice.

Figure 14:
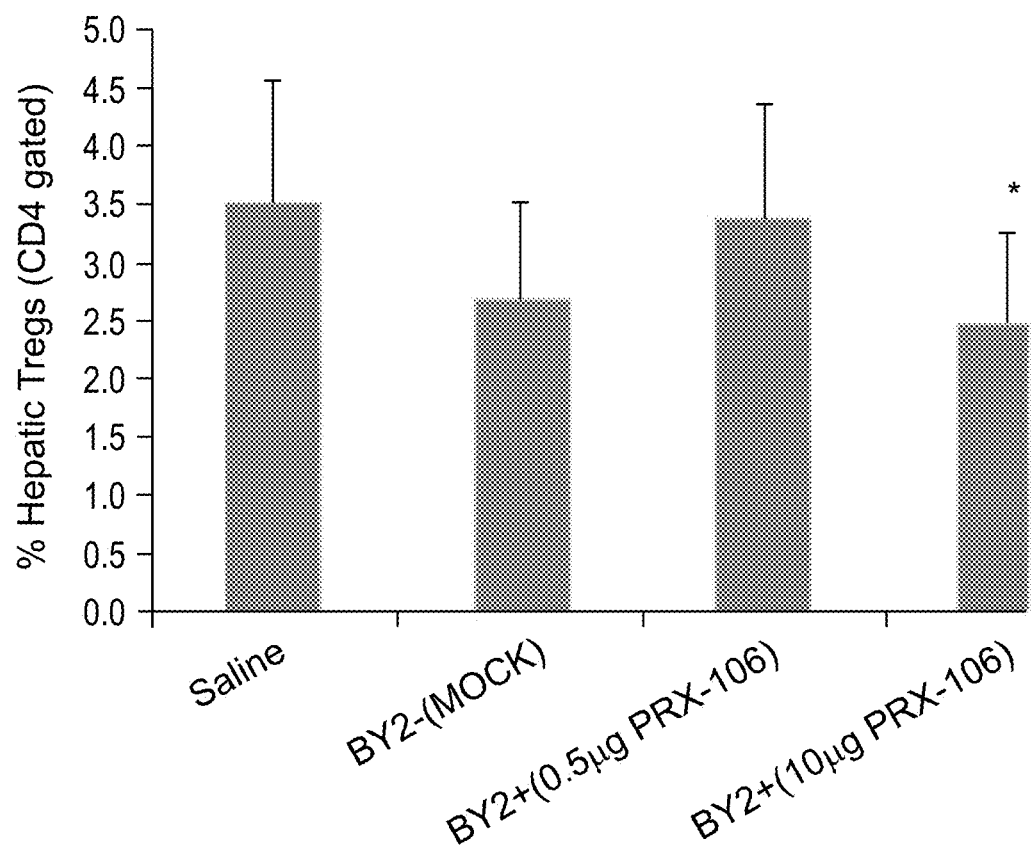

FIG. 14 is a bar graph showing the effect of oral administration of recombinant TNFR2:Fc in plant cells on hepatic Tregs in HFD mice. *p<0.05, compared to saline.

Figure 15:
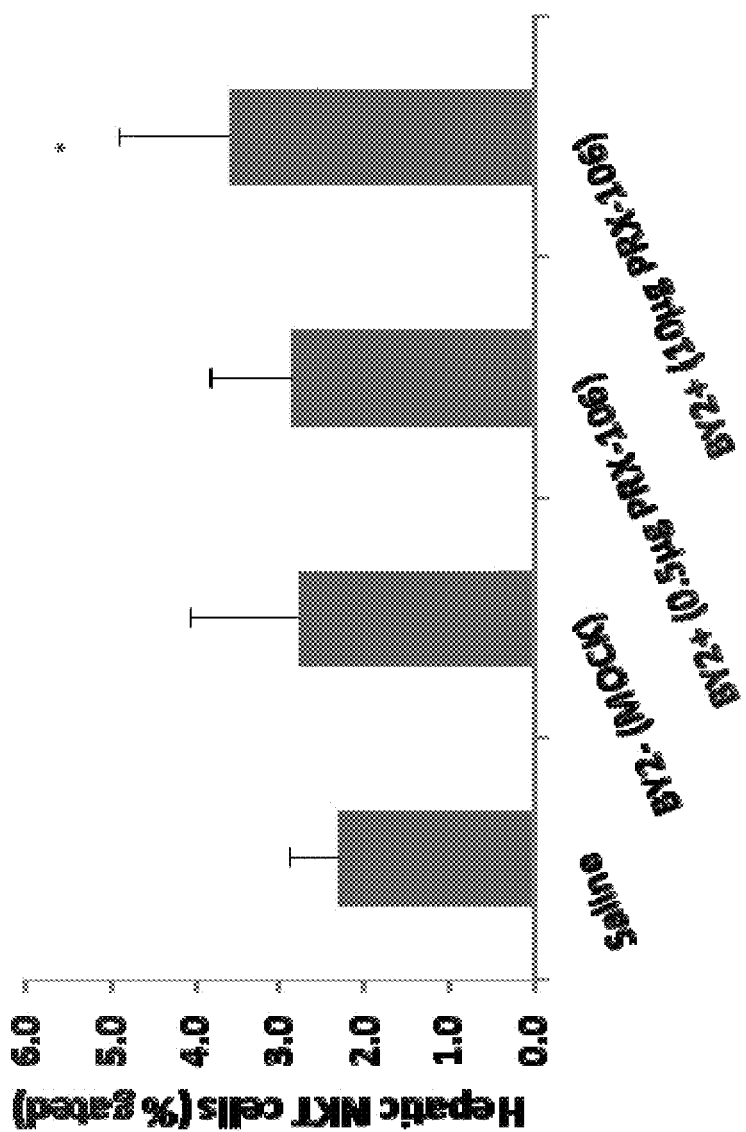

FIG. 15 is a bar graph showing the effect of oral administration of recombinant TNFR2:Fc in plant cells on hepatic NK cells in HFD mice. *p<0.05, compared to saline.

Figure 16:
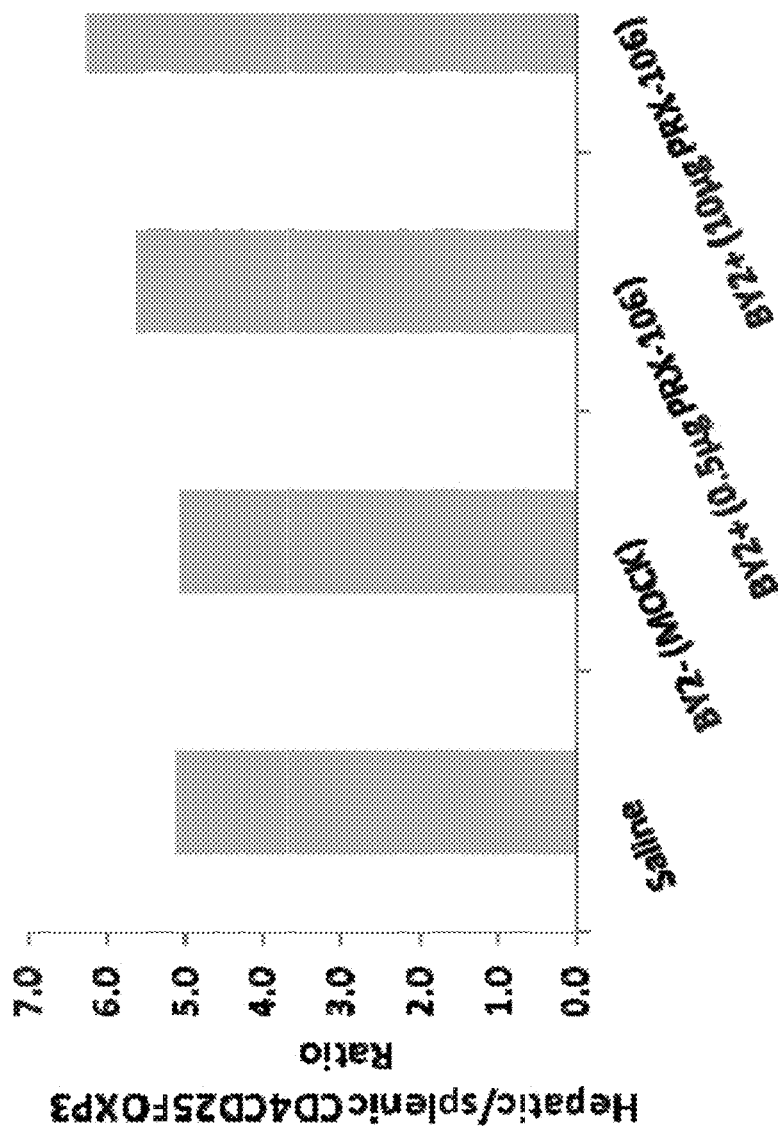

FIG. 16 is a bar graph showing the effect of oral administration of recombinant TNFR2:Fc in plant cells on splenic/hepatic CD4+CD25+FOXP3+ Ratio.

Figure 17:
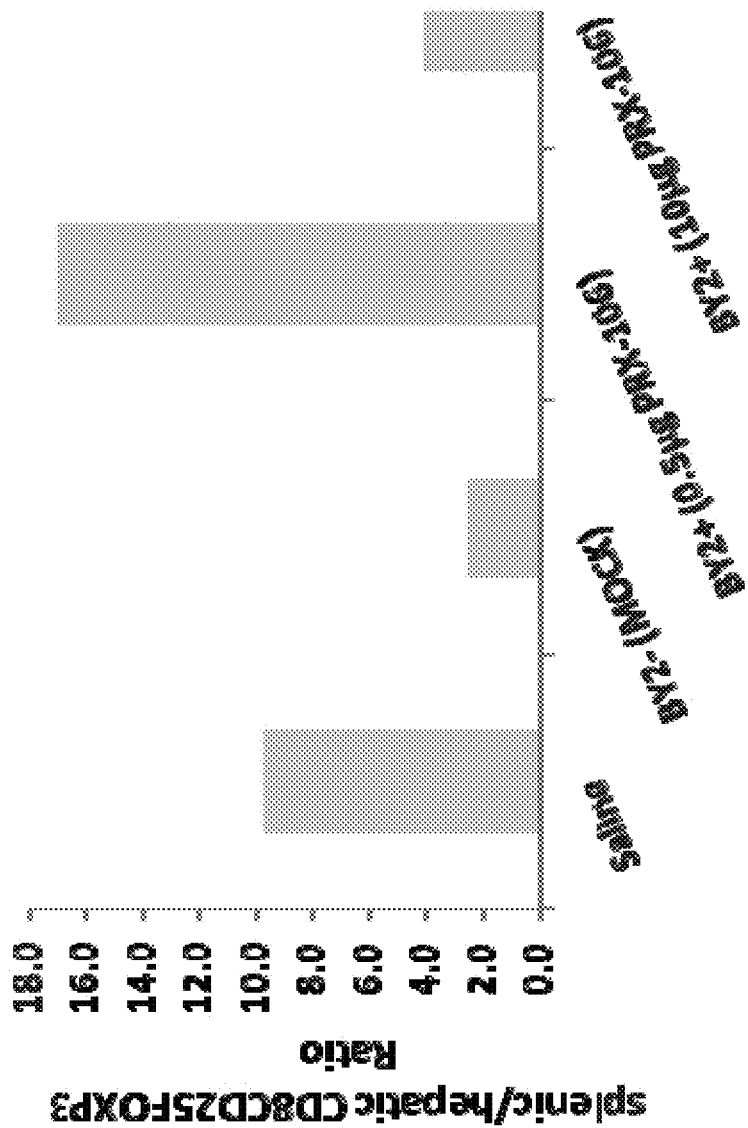

FIG. 17 is a bar graph showing the effect of oral administration of recombinant TNFR2:Fc in plant cells on splenic/hepatic CD8+CD25+FOXP3+ Ratio.

DESCRIPTION OF SPECIFIC EMBODIMENTS OF THE INVENTION

The present invention, in some embodiments thereof, relates to the use of plant cells expressing a TNF-alpha inhibitor in therapy.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Accurate delivery of biopharmaceuticals to their target tissues poses challenges impacting not only cost of therapy, but also patient acceptance and compliance, thus affecting their therapeutic efficacy. Oral administration of macromolecular biopharmaceuticals must overcome obstacles such as ingestion of pills and other solid formulations, lability of biologically active macromolecules in the GI tract, concentration of the biologically active agents at the mucosa, and low permeability of GI membranes to biologically active macromolecules.

Previous attempts at orally administering TNFR2:Fc (Enbrel®) have failed due to acidity and enzymatic degradation in the stomach. The present inventors have surprisingly shown that a biologically active TNF-binding protein (TNFR2:Fc) can be effectively orally administered by feeding plant cells expressing the recombinant TNFR2:Fc, and that oral administration of the plant cells expressing recombinant TNFR2:Fc provides significant protection from immune-mediated inflammatory disease.

When tobacco BY2 cells were transformed with a nucleic acid construct encoding recombinant TNFR2:Fc and cultured, the resulting TNF-binding protein was shown to be accurately expressed (see Example 1), having similar electrophoretic mobility, immunological cross reactivity and TNF alpha binding characteristics to those of commercial, mammalian cell expressed recombinant TNFR2:Fc (Enbrel®)(see FIGS. 2A-3). In vitro assay of biological function of the plant cell expressed recombinant TNFR2:Fc provided further evidence of protection of cells from TNF-mediated apoptosis, using two distinct types of target cells, (see FIGS. 5A-F and 6A-6G) comparable to that of Enbrel®.

Surprisingly, when cultured plant cells expressing the recombinant TNFR2:Fc were fed to mice prior to induction of concanavalin A immune-mediated hepatotoxicity, a significant and dose-dependent reduction in liver damage and serum levels of cytokine markers of inflammation was observed (Example 3, FIGS. 7A-C to 9A-C). Comparison of oral administration of plant cells expressing the recombinant TNFR2:Fc and conventional intraperitoneal administration of Enbrel® revealed nearly identical reduction of serum liver enzyme levels, indicating effective protection from the immune-related inflammatory injury characteristic of the con A hepatotxicity model.

While further reducing some embodiment of the present invention to practice, the present inventors have uncovered that oral administration of plant cells expressing the recombinant TNFR2:Fc causes ameliorates certain clinical manifestation of fatty acid disease modeled by high fat diet mice (see FIGS. 11-17). Thus, oral administration of plant cells expressing the recombinant TNFR2:Fc caused a decrease in serum enzymes and triglycerides in the animal model of fatty liver disease. The drug also altered the splenic and hepatic distribution of various populations of T cells and NK cells, indicating that the drug also functions as an immunomodulator of NAFLD and in metabolic syndrome.

Thus, according to an aspect of the invention there is provided a method of treating a TNFα associated medical condition selected from the group consisting of obesity, metabolic syndrome, diabetes, hyperlipidemia and a liver disease or disorder, the method comprising enterally administering to a subject in need thereof a therapeutically effective amount of plant cells expressing a TNFα polypeptide inhibitor, thereby treating the TNFα associated medical condition.

Alternatively or additionally there is provided a use of plant cells expressing a TNFα polypeptide inhibitor for the treatment of a TNFα associated medical condition directly associated with obesity, metabolic syndrome, diabetes and a liver disease or disorder.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, e.g., human beings at any age which suffer from the pathology. According to a specific embodiment, this term encompasses individuals who are at risk to develop the pathology.

The present teachings are thus directed at treating or preventing medical conditions which are directly associated with obesity, metabolic syndrome, diabetes and a liver disease or disorder. According to some embodiments of some aspects of the present invention, the compositions of the present invention comprising plant cells expressing a recombinant TNFα polypeptide inhibitor can be used to prevent, treat and control diseases and conditions including obesity, metabolic syndrome and diabetes. In general, the terms 'prevent', 'control' and 'treat' encompass the prevention of the development of a disease or a symptom from a patient who may have a predisposition of the disease or the symptom but has yet been diagnosed to have the disease or the symptom; the inhibition of the symptoms of a disease, namely, inhibition or retardation of the progression thereof; and the alleviation of the symptoms of a disease, namely, regression of the disease or the symptoms, or inversion of the progression of the symptoms.

All types of obesity may be controlled or treated in accordance with the invention, including endogenous obesity, exogenous obesity, hyperinsulinar obesity, hyperplastic-hypertrophic obesity, hypertrophic obesity, hypothyroid obesity and morbid obesity. However, inflammation-mediated obesity may be treated particularly effectively in accordance with the invention. By 'prevent' or 'control' or 'treat' it is meant that body weight gain, specifically body fat gain, is slowed down, stopped or reversed, resulting in a maintenance or decrease in body weight. A decrease in weight or body fat may protect against cardiovascular disease by lowering blood pressure, total cholesterol, LDL cholesterol and triglycerides, and may alleviate symptoms associated with chronic conditions such as hypertension, coronary heart disease, type 2 diabetes, hyperlipidemia, osteoarthritis, sleep apnea and degenerative joint disease.

Metabolic syndrome, or Syndrome X, is a complex multifactorial condition accompanied by an assortment of abnormalities including hypertension, hypertriglyceridemia, hyperglycemia, low levels of HDL-C, and abdominal obesity. Individuals with these characteristics typically manifest a prothrombotic and pro-inflammatory state. Available data suggest that metabolic syndrome is truly a syndrome (a grouping of risk factors).

According to the World Health Organization (WHO) Guideline, metabolic syndrome is present if an individual manifests: a) hypertension (>140 mm Hg systolic or >90 mm Hg diastolic); (b) dyslipidemia, defined as elevated plasma triglycerides (150 mg/dL), and/or low high-density lipoprotein (HDL) cholesterol (<35 mg/dL in men, <39 mg/dL in women); 3) visceral obesity, defined as a high body mass index (BMI) (30 kg/m2) and/or a high waist-to-hip ratio (>0.90 in men, >0.85 in women); and 4) microalbuminuria (urinary albumin excretion rate of 20 g/min). See WHO-International Society of Hypertension Guidelines for the Management of Hypertension. Guidelines Subcommittee. J. Hypertens. 17:151-183, 1999.

According to the National Cholesterol Education Program (NCEP ATP III study) metabolic syndrome is diagnosed if three (3) or more of the following five (5) risk factors are present: (1) a waist circumference>102 cm (40 in) for men or >88 cm (37 in) for women; (2) a triglyceride level of 150 mg/dL; (3) an HDL cholesterol level<40 mg/dL for men or <50 mg/dL for women; (4) blood pressure>130/85 mm Hg; or (5) a fasting glucose>110 mg/dL. JAMA 285: 2486-2497, 2001.

Each of the disorders associated with metabolic syndrome are risk factors in their own right, and can promote atherosclerosis, cardiovascular disease, stroke, and other adverse health consequences. However, when present together, these factors are predictive of increased risk of cardiovascular disease and stroke.

By 'control' or 'treat' it is meant that the symptoms of the metabolic syndrome shown in an individual are reduced in severity and/or in number. Such symptoms may include elevated blood glucose, glucose intolerance, insulin resistance, elevated triglycerides, elevated LDL-cholesterol, low high-density lipoprotein (HDL) cholesterol, elevated blood pressure, abdominal obesity, pro-inflammatory states, and pro-thrombotic states. By 'prevent' or 'control' or 'treat' it is additionally or alternatively meant that the risk of developing associated diseases is reduced and/or the onset of such diseases is delayed. Such associated diseases include cardiovascular disease, coronary heart disease and other diseases related to plaquing of the artery walls and diabetic conditions.

Diabetic conditions include, for example, type 1 diabetes, type 2 diabetes, gestational diabetes, pre-diabetes, slow onset autoimmune diabetes type 1 (LADA), hyperglycemia, and metabolic syndrome. For the purposes of treatment, the diabetes may be overt, diagnosed diabetes, e.g., type 2 diabetes, or a pre-diabetic condition.

Diabetes mellitus (generally referred to herein as "diabetes") is a disease that is characterized by impaired glucose regulation. Diabetes is a chronic disease that occurs when the pancreas fails to produce enough insulin or when the body cannot effectively use the insulin that is produced, resulting in an increased concentration of glucose in the blood (hyperglycemia). Diabetes may be classified as type 1 diabetes (insulin-dependent, juvenile, or childhood-onset diabetes), type 2 diabetes (non-insulin-dependent or adult-onset diabetes), LADA diabetes (late autoimmune diabetes of adulthood) or gestational diabetes. Additionally, intermediate conditions such as impaired glucose tolerance and impaired fasting glycemia are recognized as conditions that indicate a high risk of progressing to type 2 diabetes.

In type 1 diabetes, insulin production is absent due to autoimmune destruction of pancreatic beta-cells. There are several markers of this autoimmune destruction, detectable in body fluids and tissues, including islet cell autoantibodies, insulin autoantibodies, glutamic acid decarboxylase autoantibodies, and tyrosine phosphatase ICA512/IA-2 autoantibodies. In type 2 diabetes, comprising 90% of diabetics worldwide, insulin secretion may be inadequate, but peripheral insulin resistance is believed to be the primary defect. Type 2 diabetes is commonly, although not always, associated with obesity, a cause of insulin resistance.

Type 2 diabetes is often preceded by pre-diabetes, in which blood glucose levels are higher than normal but not yet high enough to be diagnosed as diabetes. The term "pre-diabetes," as used herein, is interchangeable with the terms "Impaired Glucose Tolerance" or "Impaired Fasting Glucose," which are terms that refer to tests used to measure blood glucose levels.

Chronic hyperglycemia in diabetes is associated with multiple, primarily vascular complications affecting microvasculature and/or macrovasculature. These long-term complications include retinopathy (leading to focal blurring, retinal detachment, and partial or total loss of vision), nephropathy (leading to renal failure), neuropathy (leading to pain, numbness, and loss of sensation in limbs, and potentially resulting in foot ulceration and/or amputation), cardiomyopathy (leading to heart failure), and increased risk of infection. Type 2, or noninsulin-dependent diabetes mellitus (NIDDM), is associated with resistance of glucose-utilizing tissues like adipose tissue, muscle, and liver, to the physiological actions of insulin. Chronically elevated blood glucose associated with NIDDM can lead to debilitating complications including nephropathy, often necessitating dialysis or renal transplant; peripheral neuropathy; retinopathy leading to blindness; ulceration and necrosis of the lower limbs, leading to amputation; fatty liver disease, which may progress to cirrhosis; and susceptibility to coronary artery disease and myocardial infarction. By 'prevent' it is meant that the risk of developing of diabetes is reduced or the onset of the disease is delayed. By 'control' or 'treat' it is meant that the risk of developing associated complications is reduced and/or the onset of such complications is delayed.

Diabetic conditions that are subject to treatment with plant cells expressing a recombinant TNFα polypeptide inhibitor according to the methods of the present invention can be diagnosed or monitored using any of a number of assays known in the field. Examples of assays for diagnosing or categorizing an individual as diabetic or pre-diabetic or monitoring said individual include, but are not limited to, a glycosylated hemoglobin (HbA1c) test, a connecting peptide (C-peptide) test, a fasting plasma glucose (FPG) test, an oral glucose tolerance test (OGTT), and a casual plasma glucose test.

HbA1c is a biomarker that measures the amount of glycosylated hemoglobin in the blood. HbA1c designates a stable minor glycated sub fraction of hemoglobin. It is a reflection of the mean blood glucose levels during the last 6-8 weeks, and is expressed in percent (%) of total hemoglobin. Alternatively, diabetes or pre-diabetes can be diagnosed by measuring blood glucose levels using any of several known tests in the field, including a fasting plasma glucose test or an oral glucose tolerance test. Using the fasting plasma glucose (FPG) test, a patient is classified as diabetic and is subject to treatment according to the methods of the present invention if the patient has a threshold FPG greater than 125 mg/dl, and a patient is classified as pre-diabetic and is subject to treatment according to the methods of the present invention if the patient has a threshold FPG greater than 100 mg/dl but less than or equal to 125 mg/dl. Using the oral glucose tolerance test (OGTT), a patient is classified as diabetic and is subject to treatment according to the methods of the present invention if the patient has a threshold 2-hour OGTT glucose level greater than 200 mg/dl. A patient is classified as pre-diabetic and is subject to treatment according to the methods of the present invention if the patient has a threshold 2-hour OGTT glucose level greater than 140 mg/dl but less than 200 mg/dl.

C-peptide, produced from proinsulin molecules, is secreted from islet cells into the bloodstream in equimolar proportion as insulin, and is used a biomarker for beta-cell function and insulin secretion. A fasting C-peptide measurement greater than 2.0 ng/ml is indicative of high levels of insulin, while a fasting C-peptide measurement less than 0.5 ng/ml indicates insufficient insulin production.

A subject who has been classified as having a diabetic condition, and who is subject to treatment with plant cells expressing a recombinant TNFα polypeptide inhibitor according to the methods of the present invention, may be monitored for efficacy of treatment by measuring any of the biomarkers and/or blood glucose indicators described herein, including but not limited to, glycosylated hemoglobin levels, C-peptide levels, fasting plasma glucose levels, and oral glucose tolerance test (OGTT) levels. For the biomarkers and/or blood glucose indicators described herein, efficacy of treatment can determined by quantitating the level of a biomarker or blood glucose indicator in a sample from a subject and determining whether the level of the biomarker or blood glucose indicator has reached or is approaching a threshold level. In some embodiments, a threshold level may correspond to a level of biomarker or blood glucose indicator that is a "normal" (i.e., non-diabetic) value according to standards known in the art, or a threshold level may correspond to a level of biomarker or blood glucose indicator that is a pre-diabetic or diabetic value according to standards known in the art.

In some embodiments, efficacy of treatment is determined by taking a first measurement of one or more of the biomarkers and/or blood glucose indicators in a subject prior to the start of treatment, and comparing the first measurement with secondary measurements of the same biomarker and/or blood glucose indicator in the subject at one or more time points after the onset of treatment, wherein a second measurement that has reached or exceeded a threshold value (either above or below, depending on the biomarker being measured), or is closer to the threshold value than the first measurement is to the threshold value, indicates that the treatment is efficacious.

Alternatively or additionally, efficacy of treatment may be monitored by determining whether there has been an amelioration of the secondary conditions and symptoms that are associated with the diabetic condition. For example, a subject being treated by the methods of the present invention can be monitored for improvement or reduction in symptoms of retinopathy (e.g., improvement in vision), nephropathy (e.g., improvement in kidney structure or function), neuropathy (e.g., improvement in nerve function), and/or cardiovascular disease (e.g., decreased blood pressure or lower lipid levels).

Hyperlipidemia:

According to some embodiments of some aspects of the present invention, the compositions of the present invention comprising plant cells expressing a recombinant TNFα polypeptide inhibitor can be used to prevent, treat and control hyperlipidemia (also referred to as hyperlipoproteinemia, or hyperlipidaemia) which involves abnormally elevated levels of any or all lipids and/or lipoproteins in the blood.[1] It is the most common form of dyslipidemia (which includes any abnormal lipid levels). Hyperlipidemias are also classified according to which types of lipids are elevated, that is hypercholesterolemia, hypertriglyceridemia or both in combined hyperlipidemia. Elevated levels of Lipoprotein(a) are also classified as a form of hyperlipidemia. Under the terms include are also, hyperlipoproteinemia Type I, hyperlipoproteinemia Type II, hyperlipoproteinemia Type III, hyperlipoproteinemia Type IV and hyperlipoproteinemia Type V. As well as unclassified familial forms and acquired forms of hyperlipidemia.

Liver Disease:

According to some embodiments of some aspects of the present invention, the compositions of the present invention comprising plant cells expressing a recombinant TNFα polypeptide inhibitor can be used to prevent, treat and control liver diseases and disorders including hepatitis, cirrhosis, non-alcoholic steatohepatitis (NASH) (also known as non-alcoholic fatty liver disease-NAFLD), hepatotoxicity and chronic liver disease. In general, the terms 'prevent', 'control' and 'treat' encompass the prevention of the development of a disease or a symptom from a patient who may have a predisposition of the disease or the symptom but has yet been diagnosed to have the disease or the symptom; the inhibition of the symptoms of a disease, namely, inhibition or retardation of the progression thereof; and the alleviation of the symptoms of a disease, namely, regression of the disease or the symptoms, or inversion of the progression of the symptoms.

The term "liver disease" applies to many diseases and disorders that cause the liver to function improperly or to cease functioning, and this loss of liver function is indicative of liver disease. Thus, liver function tests are frequently used to diagnose liver disease. Examples of such tests include, but are not limited to, the following:

(1) Assays to determine the levels of serum enzymes such as lactate dehydrogenase (LDH), alkaline phosphatase (ALP), aspartate aminotransferase (AST), and alanine aminotransferase (ALT), where an increase in enzyme levels indicates liver disease. One of skill in the art will reasonably understand that these enzyme assays indicate only that the liver has been damaged. They do not assess the liver's ability to function. Other tests can be used to assay a liver's ability to function;

(2) Assays to determine serum bilirubin levels. Serum bilirubin levels are reported as total bilirubin and direct bilirubin. Normal values of total serum bilirubin are 0.1-1.0 mgdl (e.g., about 2-18 mmol/L). Normal values of direct bilirubin are 0.0-0.2 mg/dl (0-4 mmol/L). Increases in serum bilirubin are indicative of liver disease;

(3) Assays to determine serum protein levels, for example, albumin and the globulins (e.g., alpha, beta, gamma). Normal values for total serum proteins are 6.0-8.0 g/dl (60-80 g/L). A decrease in serum albumin is indicative of liver disease. An increase in globulin is indicative of liver disease.

Other tests include prothrombin time, international normalized ratio, activated clotting time (ACT), partial thromboplastin time (PTT), prothrombin consumption time (PCT), fibrinogen, coagulation factors; alpha-fetoprotein, and alpha-fetoprotein-L3 (percent).

One clinically important type of liver disease is hepatitis. Hepatitis is an inflammation of the liver that can be caused by viruses (e.g., hepatitis virus A, B and C (HAV, HBV, and HCV, respectively), chemicals, drugs, alcohol, inherited diseases, or the patient's own immune system (autoimmune hepatitis). This inflammation can be acute and resolve within a few weeks to months, or chronic, and persist over many years. Chronic hepatitis can persist for decades before causing significant symptoms, such as cirrhosis (scarring and loss of function), liver cancer, or death. Other important examples of the different diseases and disorders encompassed by the term "liver disease" and suitable for treatment or prevention or control using the compositions and methods of the present invention include, but are not limited to amebic liver abscess, biliary atresia, fibrosis, cirrhosis, coccidioidomycosis, delta agent, hepatocellular carcinoma (HCC), alcoholic liver disease, primary biliary cirrhosis, pyogenic liver abscess, Reye's syndrome, sclerosing cholangitis, and Wilson's disease. In some embodiments, the compositions and methods described herein are suitable for the treatment of liver disease characterized by the loss or damage of parenchymal liver cells. In some aspects, the etiology of this can be a local or systemic inflammatory response.

Liver failure occurs when large parts of the liver become damaged and the liver is no longer able to perform its normal physiological function. In some aspects, liver failure can be diagnosed using the above described assays of liver function or by a subject's symptoms. Symptoms that are associated with liver failure include, for example, one or more of the following, nausea, loss of appetite, fatigue, diarrhea, jaundice, abnormal/excessive bleeding (e.g., coagulopathy), swollen abdomen, mental disorientation or confusion (e.g., hepatic encephalopathy), sleepiness, and coma.

Chronic liver failure occurs over months to years and is most commonly caused by viruses (e.g., HBV and HCV), long-term/excessive alcohol consumption, cirrhosis, hemochromatosis, and malnutrition. Acute liver failure is the appearance of severe complications after the first signs of liver disease (e.g., jaundice) and includes a number of conditions, all of which involve severe hepatocyte injury or necrosis. In some embodiments, the compositions and methods described herein are particularly suitable for the treatment of hyperacute, acute, and subacute liver failure, fulminant hepatic failure and late onset fulminant hepatic failure, all of which are referred to herein as "acute liver failure." Common causes for acute liver failure include, for example, viral hepatitis, exposure to certain drugs and toxins (e.g., fluorinated hydrocarbons (e.g., trichloroethylene and tetrachloroethane), *amanita phalloides* (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

The term "hepatitis" is used to describe a liver condition which implies injury to the liver characterized by the presence of inflammatory cells in the tissue of the organ. The condition can be self-limiting, healing on its own, or can progress to scarring of the liver. Hepatitis is acute when it lasts less than six months and chronic when it persists longer than six months. A group of viruses known as the hepatitis viruses cause most cases of liver damage worldwide. Hepatitis can also be due to toxins (notably alcohol), other infections or from autoimmune process. Hepatitis includes hepatitis from viral infections, including Hepatitis A through E (A, B, C, D and E—more than 95% of viral cause), Herpes simplex, Cytomegalovirus, Epstein-Ban virus, yellow fever virus, adenoviruses; non-viral infections, including *toxo-*

*plasma*, Leptospira, Q fever, rocky mountain spotted fever, alcohol, toxins, including *amanita* toxin in mushrooms, carbon tetrachloride, asafetida, among others, drugs, including paracetamol, amoxycillin, antituberculosis medicines, minocycline and numerous others as described herein; ischemic hepatitis (circulatory insufficiency); pregnancy; autoimmune conditions, including Systemic Lupus Erythematosus (SLE); and non-alcoholic steatohepatitis.

"Sterile inflammation" is used to describe inflammation of the liver which is triggered by intracellular molecules released from dying cells that have lost integrity of their plasma membrane. This inflammation occurs in the absence of causative agents such as viruses or bacteria and alcohol. A number of intracellular molecules have been identified that can stimulate other cells to produce proinflammatory cytokines and chemokines. Such proinflammatory cellular molecules are thought to function by engaging receptors on cytokine-producing cells. If left untreated, sterile inflammation may progress to non-alcoholic fatty liver disease (NAFLD), non-alcoholic steatohepatitis (NASH) or cyrrhosis.

"Non-alcoholic steatohepatitis" or "NASH" is a condition of the liver in which inflammation is caused by a buildup of fat in the liver. NASH is part of a group of liver diseases, known as nonalcoholic fatty liver disease, in which fat builds up in the liver and sometimes causes liver damage that gets worse over time (progressive liver damage). "Non-alcoholic fatty liver disease" (NAFLD) is fatty inflammation of the liver which is not due to excessive alcohol use. It is related to insulin resistance and the metabolic syndrome, obesity, high cholesterol and triglycerides, and diabetes, and may respond to treatments originally developed for other insulin resistant states (e.g. diabetes mellitus type 2), such as weight loss, metformin and thiazolidinediones. Non-alcoholic steatohepatitis (NASH) is the most extreme form of NAFLD, which is regarded as a major cause of cirrhosis of the liver of unknown cause.

Other factors that have been known to contribute to NASH include: surgery that shorten the intestines, the stomach, or both, such as jejunal bypass operation or biliopancreatic diversion; prolonged use of feeding tube or other method of receiving nutrition; certain drugs, including amiodarone, glucocorticoids, synthetic estrogens, and tamoxifen.

NASH is a condition that may get worse over time (called a progressive condition) and can cause scarring (fibrosis) of the liver, which leads to cirrhosis. "Cirrhosis" describes a condition in which liver cells have been replaced by scar tissue. The term "cirrhosis of the liver" or "cirrhosis" is used to describe a chronic liver disease characterized by replacement of liver tissue by fibrous scar tissue as well as regenerative nodules, leading to progressive loss of liver function. Cirrhosis is most commonly caused by fatty liver disease, including NASH, as well as alcoholism and hepatitis B and C, but also may be of unknown cause. Potentially life-threatening complications of cirrhosis are hepatic encephalopathy (confusion and coma) and bleeding from esophageal varices. Cirrhosis has historically been thought to be generally irreversible once it occurs, and historical treatment focused on preventing progression and complications. In advanced stages of cirrhosis, the only option is a liver transplant. The plant cells expressing a recombinant TNFα polypeptide inhibitor and methods of the present invention may be used to limit, inhibit, reduce the likelihood or treat cirrhosis of the liver without regard to its etiology.

The plant cells expressing a recombinant TNFα polypeptide inhibitor and methods of the present invention can be used to treat, prevent or control chemical liver trauma and hepatotoxicity. "Chemical trauma" or "acute chemical trauma" refers to serious injury which occurs to a patient over a short duration as a consequence of chemical toxicity, including drug-induced toxicity or trauma. Drug-induced acute liver trauma, including acetaminophen-induced acute liver trauma, is acute liver injury which occurs as a result or consequence of exposure to a drug (e.g., drug overdose), especially acetaminophen toxicity. Compounds according to the present invention are useful for reducing the injury to the liver which occurs from physical and chemical trauma, especially including drug-induced (drug overdose) and acetaminophen-induced acute liver trauma.

Hepatotoxocity is chemical liver trauma resulting from a hepatotoxic agent, or hepatotoxicity-inducing bioactive agent. The terms "hepatotoxic agent" and "a hepatotoxicity inducing bioactive agent" are used synonymously in context to describe compounds which often produce hepatotoxicity in patients administered such agents. Examples of hepatoxicity agents include, for example, anaesthetic agents, antiviral agents, anti-retroviral agents (nucleoside reverse transcriptase inhibitors and non-nucleoside reverse transcriptase inhibitors), especially anti-HIV agents, anticancer agents, organ transplant drugs (cyclosporin, tacrolimus, OKT3), antimicrobial agents (anti-TB, anti-fungal, antibiotics), anti-diabetes drugs, vitamin A derivatives, steroidal agents, especially including oral contraceptives, anabolic steroids, androgens, non-steroidal anti-inflammatory agents, anti-depressants (especially tricyclic antidepressants) glucocorticoids, natural products and herbal and alternative remedies, especially including St. John's wort.

Hepatotoxicity may manifest as triglyceride accumulation which leads to either small droplet (microvesicular) or large droplet (macrovesicular) fatty liver. There is a separate type of steatosis where phospholipid accumulation leads to a pattern similar to the diseases with inherited phospholipid metabolism defects (e.g. Tay-Sachs disease).

According to a specific embodiment, the liver disease is a fatty liver disease (e.g., non-alcoholic). In this case and according to some embodiments, the TNFalpha inhibitor (e.g., orally administered plant cells expressing recombinant TNFR2:Fc) causes a reduction in serum enzymes (e.g., AST or ALT or both) and/or triglycerides and can alternatively or additionally alter the distribution of T cells and NK cells in the liver and spleen, as compared to that of an untreated subject in the same disease stage.

The plant cells expressing a recombinant TNFα polypeptide inhibitor and methods of the present invention can be used to treat, prevent or control chronic liver disease. Chronic liver disease is marked by the gradual destruction of liver tissue over time. Several liver diseases fall under this category, including cirrhosis and fibrosis, the latter of which is often the precursor to cirrhosis. Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functioning liver tissue resulting in a decreasing amount of blood flow to the liver leaving the liver incapable of fully processing nutrients, hormones, drugs, and poisons that are found in the bloodstream. More common causes of cirrhosis include alcoholism, hepatitis C viral infections, ingestion of toxins, and fatty liver, but many other possible causes also exist. Chronic hepatitis C virus (HCV) infection and non-alcoholic steatohepatitis (NASH) are the two major causes of chronic liver disease in the United States estimated to affect between 3-5 million people. A rising concern is the continuously increasing number of U.S. citizens, currently numbering over 30 million, with obesity and metabolic syndrome that have non-alcoholic fatty liver disease (NAFLD) with approximately 10% who will eventually develop NASH. Other bodily complications are a consequence of a loss of liver function. The most common complication of cirrhosis is a condition known as ascites, an accumulation of fluid in the peritoneal cavity, which can lead to an increased risk of spontaneous bacterial peritonitis possibly resulting in the premature death of the patient.

The plant cells expressing a recombinant TNFα polypeptide inhibitor and methods of the present invention may be used to limit, inhibit, reduce the likelihood or treat cancer of the liver. Risk factors for liver cancer include type 2 diabetes (exacerbated by obesity) and metabolic syndrome. The risk of liver cancer in type 2 diabetics is greater (about 3 to 7 times the non-diabetic risk) depending on the duration of diabetes and treatment protocol. Metabolic syndrome results in inflammation, steatosis, fibrosis, cirrhosis, apoptosis, altered gene expression and eventually even liver cancer. In addition, lipid metabolism abnormality, hypertension, hyperglycemia and metabolic syndrome, exacerbating hepatitis and the progress of hepatitis to cirrhosis, which can further lead to liver cancer, for example, by the activation of stellate cells.

Various methodologies can be used in the screening and diagnosis of liver cancer and are well known in the art. Indicators for liver cancer include tumor markers such as elevated alpha-fetoprotein (AFP) or des-gamma carboxyprothrombin (DCP). Scanning and imaging techniques are also helpful, including ultrasound, CT scans and MRI. Macroscopically, liver cancer may be nodular, or an infiltrative tumor which is diffuse and poorly circumscribed.

As used the term "TNFα" refers to Tumor necrosis factor-alpha (TNF, cachexin, or cachectin) that is a cytokine involved in systemic inflammation and a member of a group of cytokines that stimulate the acute phase reaction. TNFα is produced primarily by activated macrophages (M1), although it can be produced by many other cell types as CD4+ lymphocytes, NK cells and neurons. The protein is encoded by TNFA gene and has the Ref_seq number: NP_000585. The protein is known to stimulate an inflammatory response (pro-inflammatory cytokine).

A "TNFα polypeptide inhibitor" as used herein refers to a polypeptide that binds TNFα and inhibits and/or hinders TNFα activity as reflected in TNFα binding to a TNFα-receptor (TNFR) including any of the following: (a) TNFR, preferably endogenous (i.e., native to the individual or host), cell membrane bound TNFR; (b) the extracellular domain(s) of TNFR; and/or (c) the TNFα binding domains of TNFR (which may be a portion of the extracellular domain). According to a specific embodiment, inhibition of TNFα binding to the receptor is by at least 50%, e.g., 50-100%. 50-95%, 60-90% or even 70-90%.

TNFα inhibitors include, but are not limited to, TNFα receptors (or appropriate portions thereof, as described herein) and anti-TNFα antibodies.

As used herein, the "biological activity" of a TNFα inhibitor is to bind to TNFα and inhibit and/or hinder TNFα from binding to any of the following: (a) TNFR, preferably endogenous, cell membrane bound TNFR; (b) the extracellular domain(s) of TNFR; and (c) the TNFα binding domains of TNFR (which may be a portion of the extracellular domain). A TNFα inhibitor can be shown to exhibit biological activity using assays known in the art to measure TNFα activity and its inhibition, an example of which is provided herein.

As used herein, the terms "TNF receptor polypeptide" and "TNFR" refer to polypeptides derived from TNFR (from any species e.g., human) which are capable of binding TNFα. Two distinct cell-surface TNFRs have been described: Type II TNFR (or p75 TNFR or TNFRII) and Type I TNFR (or p55 TNFR or TNFRI). The mature full-length human p75 TNFR is a glycoprotein having a molecular weight of about 75-80 kilodaltons (kD). The mature full-length human p55 TNFR is a glycoprotein having a molecular weight of about 55-60 kD. The preferred TNFR polypeptides of this invention are derived from TNFR Type I and/or TNFR type II. Exemplary accession numbers are provided hereinbelow. According to a specific embodiment, the TNFR is capable of binding TNFα in a specific manner e.g., Kd below $10^{-5}$ M.

According to a specific embodiment, the TNFα inhibitor is a chimeric polypeptide.

A "chimeric polypeptide" or "fusion polypeptide" is a polypeptide comprising regions in a different position than occurs in nature. The regions may normally exist in separate proteins and are brought together in the chimeric or fusion polypeptide, or they may normally exist in the same protein but are placed in a new arrangement in the chimeric or fusion polypeptide. A chimeric or fusion polypeptide may also arise from polymeric forms, whether linear or branched, of TNFR polypeptide(s).

As used herein, an "extracellular domain" of TNFR refers to a portion of TNFR that is found between the amino-terminus of TNFR and the amino-terminal end of the TNFR transmembrane region. The extracellular domain of TNFR binds TNFα.

The terms "polypeptide", "peptide" and "protein" are used interchangeably herein to refer to polymers of amino acids of any length. The terms also encompass an amino acid polymer that has been modified; for example, disulfide bond formation, glycosylation, lipidation, or conjugation with a labeling component.

Specific examples of TNFα polypeptide inhibitors include, but are not limited to, infliximab (Remicade™) and adalimumab (Humira™), which consist of, chimeric human-mouse anti-TNFα monoclonal antibodies and fully human anti-TNF-alpha monoclonal antibodies, respectively. Another example of an anti-TNFα antibody which can be used in accordance with the present teachings include golimumab (Simponi™).

Also included under this definition are chimeric polypeptides which include the commercial etanercept (further described hereinbelow) and Lenercept (a chimeric polypeptide consisting of p55sTNF-RI-IgG1) under their scope. Such chimeric polypeptides are further described hereinbelow.

Thus, according to a specific embodiment the TNFα polypeptide inhibitor is a chimeric polypeptide comprising:
(i) a first domain which comprises a TNFα binding domain of a TNF receptor; and
(ii) a second domain which comprises an Fc domain of an immunoglobulin, wherein the first domain and the second domain are N-terminally to C-terminally respectively sequentially translationally fused and wherein the chimeric polypeptide specifically binds TNFα.

The first domain is thus composed of at least the TNF binding domain of a TNF receptor (TNFR). The first domain is a soluble protein. Thus according to a specific embodiment, the first domain and even the entire chimeric polypeptide are soluble proteins which are not membrane anchored.

Soluble forms of TNFRs may include monomers, fusion proteins (also called "chimeric proteins), dimers, trimers or higher order multimers. In certain embodiments of the invention, the soluble TNFR derivative is one that mimics the 75 kDa TNFR or the 55 kDa TNFR and that binds to TNFα. in vivo. The soluble TNFR mimics of the present invention may be derived from TNFRs p55 or p75 or fragments thereof. TNFRs other than p55 and p75 also are useful for deriving soluble TNFR for treating the various medical disorders described herein, such for example the TNFR that is described in WO 99/04001. Soluble TNFR molecules used to construct TNFR mimics include, for example, analogs or fragments of native TNFRs having at least 20 amino acids, that lack the transmembrane region of the native TNFR, and that are capable of binding TNFα. Such soluble forms of TNFR compete for TNFα with the receptors on the cell surface, thus inhibiting TNFα from binding to cells, thereby preventing it from manifesting its biological activities. Binding of soluble TNFRs to TNFα can be assayed using ELISA or any other convenient assay.

According to a specific embodiment, the first domain is derived from TNFR2. (e.g., AAA36755).

According to an embodiment of the invention, the first domain is 200-250 amino acids long.

According to a specific embodiment, the first domain comprises the amino acid sequence LCAP (SEQ ID NO: 11) and VFCT (SEQ ID NO: 12).

According to a specific embodiment, the first domain comprises the amino acid sequence LPAQVAFXPYAPEPGSTC (SEQ ID NO: 13) or LPAQVAFTPYAPEPGSTC (SEQ ID NO: 17)

According to a specific embodiment, the first domain is as set forth in SEQ ID NO: 2 (encoded by SEQ ID NO: 1).

As used herein "an Fc domain of an immunoglobulin" refers to a region of a heavy chain of an antibody, typically comprising at least 2 constant domains (e.g., CH2 and CH3 domains, as these terms are defined in the art) of the heavy chain. The Fc domain may be obtained, for example, in the form of a dimer, by digestion of an antibody by papain. A dimer of Fc domain polypeptides, connected by disulfide bonds, forms the "tail" region of an antibody. As is known in the art, Fc domains of some classes of antibodies may be in the form of multimers. Thus, the Fc domain is optionally monomeric, optionally dimeric and optionally multimeric. Optionally, the polypeptide described herein is in the form of a dimer, the polypeptide comprising an Fc dimer, or in the form of a multimer, the polypeptide comprising an Fc multimer.

The Fc domain may encompass modified forms of a native Fc domain (i.e., a domain which occurs naturally in an antibody), for example, polypeptides having at least 90% homology, optionally at least 95% homology, and optionally at least 98% homology, to a native Fc domain. Modified Fc domains are described, for example, in International Patent Applications WO 97/34631 and WO 96/32478.

Optionally, a native Fc is modified so as to remove sites which provide structural features or biological activity that are not required for embodiments of the present invention. Examples of such sites include residues that affect or are involved in disulfide bond formation, incompatibility with a selected host cell, N-terminal heterogeneity upon expression in a selected host cell, glycosylation, interaction with complement, binding to an Fc receptor (other than a neonatal Fc receptor), and/or antibody-dependent cellular cytotoxicity.

The polypeptide according to embodiments of the present invention may also comprise a fragment of an Fc domain. Optionally, the fragment comprises at least 20%, optionally at least 50%, and optionally at least 80% of an Fc domain, as defined hereinabove.

The Fc domain or fragment thereof optionally includes a binding site for a neonatal Fc receptor (FcRn). This is of particular significance when administering the chimeric polypeptide via an enteral route.

According to one embodiment, attachment of an Fc domain or a fragment thereof to the first domain results in a polypeptide having a longer half-life in vivo than the first domain per se. This may be due to the long serum half-life of the Fc domain (which may be due to salvage of the Fc via binding to FcRn) and/or due to the greater size of the polypeptide in comparison to the first domain per se, which reduces clearance from the bloodstream by glomerular filtration. According to another embodiment, the resulting polypeptides have reduced immunogenicity as compared to the first domain per se.

According to optional embodiments, the Fc domain or fragment thereof is a human Fc domain (e.g., derived from a human antibody) or fragment thereof.

According to exemplary embodiments, the Fc domain (or fragment thereof) is an IgG (e.g., IgG1) Fc domain (or fragment thereof).

According to a specific embodiment, the second domain is as set forth in SEQ ID NO: 9 (encoded by SEQ ID NO: 8).

Thus, the second domain of the chimeric polypeptide comprises at least a portion of a constant immunoglobulin domain, e.g. a constant heavy immunoglobulin domain or a constant light immunoglobulin domain. Preferably, the second domain comprises at least a portion of a constant heavy immunoglobulin domain. The constant heavy immunoglobulin domain is preferably an Fc fragment comprising the CH2 and CH3 domain and, optionally, at least a part of the hinge region. The immunoglobulin domain may be an IgG, IgM, IgD or IgE immunoglobulin domain or a modified immunoglobulin domain derived, therefrom. Preferably, the second domain comprises at least a portion of a constant IgG immunoglobulin domain. The IgG immunoglobulin domain may be selected from IgG1, IgG2, IgG3 of IgG4 domains or from modified domains such as are described in U.S. Pat. No. 5,925,734. The immunoglobulin domain may exhibit effector functions. In some embodiments, however, modified immunoglobulin domains having modified, e.g. at least partially deleted, effector functions may be used. Thus for example, the receptor.

According to an embodiment of the invention, the chimeric fusion of the first domain and the second domain forms Etanercept (Immunex) having SEQ ID NO: 10.

It will be appreciated that the species origin of the first domain and the second domain is selected according to the treated subject. Thus, according to a specific embodiment, the first domain and the second domain are of human origin or modified such that they don't incur immunogenic reaction when administered to human subjects.

As used herein "Etanercept" and "Enbrel" are interchangeably used to designate the commercially available TNFR2:Fc by Immunex Corporation. Etanercept is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1. Plant cells expressing TNFR2:Fc are also termed PRX-106.

According to another embodiment, the chimeric polypeptide comprises:
(i) a first domain which comprises a TNFα binding domain of a TNF receptor;
(ii) a second domain which comprises an Fc domain of an immunoglobulin; and
(iii) a third domain comprising an endoplasmic reticulum retention signal; wherein the first domain, second domain and third domain are N-terminally to C-terminally respectively sequentially translationally fused and wherein the chimeric polypeptide specifically binds TNFα.

Thus, according to this aspect of the invention, the chimeric protein is expressed such that it is retained in the endoplasmic reticulum. According to a specific embodiment, at least a portion of the TNFR2:Fc molecules (e.g., at least 20%) in the cell are retained in the ER.

As used herein, the term "endoplasmic reticulum retention signal peptide" refers to a peptide sequence which, when present at the N- or C-terminus of a polypeptide, causes the polypeptide to be retrieved from the Golgi apparatus, and retained in the endoplasmic reticulum (see Rayon et al. Journal of Experimental Botany, Vol. 49, No. 326, pp. 1463-1472, 1998; and Neumann, et al Annals of Botany, 2003; 92:167-180). In one embodiment, the endoplasmic reticulum retention signal peptide is HDEL (SEQ ID NO: 14), KDEL (SEQ ID NO: 15) or SEKDEL (SEQ ID NO: 16).

As mentioned, the first domain and second domain (and third domain when present) are N-terminally to C-terminally respectively sequentially translationally fused. This means that the first domain is located N-terminally to the second domain (the carboxy terminus of the first domain is translationally fused to the N-terminus of the second domain), and the second domain is located N-terminally of the third domain (the carboxy terminus of the second domain is translationally fused to the N-terminus of the third domain). Thus, the second domain is practically sandwitched by the first domain at the N-terminus and the third domain at the C-terminus. Schematic presentation is as follows: first domain>second domain (>third domain) are orderly oriented from the N-terminus to the C-terminus (see FIG. 1). The linkage between the domains may be direct or indirect by the use of linkers such as peptide linkers.

The molecule may further comprise an additional domain which encodes for an endoplasmic reticulum signal sequence which is oriented upstream (N-terminally) of the first domain and translationally fused thereto.

As used herein "an endoplasmic reticulum (ER) signal peptide" refers to a signal sequence, leader sequence or leader peptide that is a short (e.g., 5-30 amino acids long) peptide present at the N-terminus of the majority of newly synthesized proteins that are destined towards the secretory pathway.

According to a specific embodiment, the ER signal peptide is derived (taken, truncated) from a plant protein.

According to a specific embodiment, the endoplasmic reticulum signal peptide is from *N. plumbaginifolia* Calreticulin protein.

According to a further specific embodiment, the signal peptide from *N. plumbaginifolia* Calreticulin protein is as set forth in SEQ ID NO: 4 and encoded by the nucleic acid sequence of SEQ ID NO: 3.

As used herein the term "translationally fused at the N-terminal" or "translationally fused at the C-terminal" refers to covalent attachment of the indicated peptide via a peptide bond to the N-terminal or C-terminal amino acid of the respective domain typically as a result of recombinant expression.

According to a specific embodiment, the chimeric polypeptide is as set forth in SEQ ID NO: 6.

According to a specific embodiment, the chimeric polypeptide is as set forth in SEQ ID NO: 7, 204 or 205.

As mentioned the recombinant chimeric proteins of the invention are produced in plant cells.

In order to express the polypeptide, an isolated polynucleotide comprising a nucleic acid sequence encoding the chimeric polypeptide as described herein is ligated into a "plant nucleic acid expression construct".

As used herein the term "plant nucleic acid expression construct" refers to a nucleic acid construct which includes the nucleic acid of some embodiments of the invention and at least one promoter for directing transcription of nucleic acid in a host plant cell. Further details of suitable transformation approaches are provided hereinbelow.

According to some embodiments of the invention, there is provided a nucleic acid expression construct comprising the nucleic acid sequence of the invention, and a promoter for directing transcription of the nucleic acid sequence in a plant host cell.

As used herein the term "nucleic acid sequence" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments of the present invention, the nucleic acid sequences encoding the polypeptides of the present invention are optimized for expression in plants. Examples of such sequence modifications include, but are not limited to, an altered G/C content to more closely approach that typically found in the plant species of interest, and the removal of codons atypically found in the plant species commonly referred to as codon optimization. In one embodiment, the codon usage of the nucleic acid sequence encoding the chimeric polypeptide is optimized for *Nicotiana tabacuum* or *Nicotiana benthamiana*.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants has been compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage table having been statistically determined based on the data present in Genbank.

By using such codon optimization tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

The desired encoding nucleotide sequence may already, in advance of any modification, contain a number of codons that correspond to a statistically-favored codon in a particular plant species. Therefore, codon optimization of the native nucleotide sequence may comprise determining which codons, within the desired nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus according to a specific embodiment, there is provided a *Nicotinia tobaccum* optimized sequence as set forth in SEQ ID NO: 5.

According to some embodiments of the invention, the nucleic acid sequence coding for the cimeric polypeptide is operably linked to a cis-acting regulatory sequence active in plant cells, such as a plant promoter sequence.

A coding nucleic acid sequence is "operably linked" to a regulatory sequence (e.g., promoter) if the regulatory sequence is capable of exerting a regulatory effect on (e.g. effect on the expression of) the coding sequence linked thereto.

Any suitable promoter sequence can be used by the nucleic acid construct of the present invention. Preferably the promoter is a constitutive promoter, a tissue-specific, or an inducible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Such a promoter can be constitutive, i.e., capable of directing high level of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

Examples of preferred promoters useful for the methods of some embodiments of the invention are presented in Table I, II, III and IV.

TABLE I

Exemplary constitutive promoters for use in the performance of some embodiments of the invention

| Gene Source | Expression Pattern | Reference |
|---|---|---|
| Actin | constitutive | McElroy etal, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107-121, 1996 |

TABLE II

Exemplary seed-preferred promoters for use in the performance of some embodiments of the invention

| Gene Source | Expression Pattern | Reference |
| --- | --- | --- |
| Seed specific genes | seed | Simon, et al., Plant Mol. Biol. 5. 191, 1985; Scofield, etal., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltr1 promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al, Plant Cell Physiology 398) 885-889, 1998 |
| rice OSH1 | embryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| *sorghum* gamma-kafirin | endosperm | PMB 32: 1029-35, 1996 |
| KNOX | embryo | Postma-Haarsma of al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, etal., Plant Mol. Biol. 19: 873-876, 1992 |

TABLE III

Exemplary flower-specific promoters for use in the performance of the invention

| Gene Source | Expression Pattern | Reference |
| --- | --- | --- |
| AtPRP4 | flowers | wwwdotsalusdotmediumdotedu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |

TABLE IV

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 | strong root |
| PR00111 | uclacyanin 3-like protein | weak discrimination center/ shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/b-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |

TABLE IV-continued

Alternative rice promoters for use in the performance of the invention

| PRO # | gene | expression |
|---|---|---|
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2_short (barley) | |
| PRO0228 | BLZ-2_long (barley) | |

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of some embodiments of the invention can be utilized to stably or transiently transform plant cells. In stable transformation, the nucleic acid is integrated into the plant genome and as such it represents a stable and inherited trait. In transient transformation, the exogenous polynucleotide is expressed by the cell transformed but it is not integrated into the genome and as such it represents a transient trait.

Thus, according to some aspects of the present invention, there is provided an isolated cell comprising the nucleic acid construct of the invention.

As used herein, the term "isolated cell" refers to a cell at least partially separated from the natural environment e.g., from a plant. In some embodiments, the isolated cell is a plant cell of a whole plant. In some embodiments, the isolated cell is a plant cell, for example, a plant cell in culture.

The term "'plant" as used herein encompasses whole plants, ancestors and progeny of the plants and plant parts, including seeds, shoots, stems, roots (including tubers), and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalypfus* spp., *Euclea schimperi, Eulalia vi/losa, Pagopyrum* spp., *Feijoa sellowlana, Fragaria* spp., *Flemingia* spp, *Freycinetia banksli, Geranium thunbergii, GinAgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp., *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays,* amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, *eucalyptus,* a tree, an ornamental plant, a perennial grass and a forage crop. Alternatively algae and other non-Viridiplantae can be used for the methods of the present invention.

According to some embodiments of the invention, the plant or plant cell is a duckweed plant, cell or nodule. Duckweed (members of the monocotyledonous family Lemnaceae, or Lemna) plant or duckweed nodule cultures can be efficiently transformed with an expression cassette containing a nucleotide sequence of interest by any one of a number of methods including *Agrobacterium*-mediated gene transfer, ballistic bombardment, or electroporation. Methods for molecular engineering of duckweed cells and detailed description of duckweed expression systems useful for commercial production of polypeptides are known in the art (see, for example, U.S. Pat. Nos. 6,040,498 and 6,815,184 to Stomp, et al, and U.S. Pat. No. 8,022,270 to Dickey et al, all of which are incorporated fully by reference herein).

According to some embodiments of the invention, the plant or plant cell used by the method of the invention is a crop plant or cell of a crop plant such as rice, maize, wheat, barley, peanut, potato, sesame, olive tree, palm oil, banana, soybean, sunflower, canola, sugarcane, alfalfa, millet, leguminosae (bean, pea), flax, *lupinus*, rapeseed, tobacco, poplar and cotton.

According to further embodiments the plant cells includes tobacco cells, *Agrobacterium rhizogenes* transformed root cell, celery cell, ginger cell, horseradish cell and carrot cells. In one embodiment the tobacco cells are from a tobacco cell line, such as, but not limited to *Nicotiana tabacum* L. cv Bright Yellow (BY-2) cells. The plant cells may be grown according to any type of suitable culturing method, including but not limited to, culture on a solid surface (such as a plastic culturing vessel or plate for example) or in suspension. It will be noted that some cells, such as the BY-2 and carrot cells can be cultured and grown in suspension. Suitable devices and methods for culturing plant cells in suspension are known in the art, for example, as described in International Patent Application PCT IL2008/000614. In yet another embodiment the cells are cells of whole tobacco plants or plant tissues, including, but not limited to *Nicotiana benthamiana*. According to yet another embodiment, the plant cells are carrot cells.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the nucleic acid sequence includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

According to some embodiments of the invention, the method further comprises growing the plant cell expressing the nucleic acid. The plant cells can be any plant cells desired. The plant cells can be cultured cells, cells in cultured tissue or cultured organs, or cells in a plant. In some embodiments, the plant cells are cultured cells, or cells in cultured tissue or cultured organs. In yet further embodiments, the plant cells are any type of plant that is used in gene transference. The plant cell can be grown as part of a whole plant, or, alternatively, in plant cell culture.

According to some aspects of the invention, the plant cells are grown in a plant cell suspension culture. As used herein, the term "suspension culture" refers to the growth of cells separate from the organism. Suspension culture can be facilitated via use of a liquid medium (a "suspension medium"). Suspension culture can refer to the growth of cells in liquid nutrient media. Methods and devices suitable for growing plant cells of the invention in plant cell suspension culture are described in detail in, for example, PCT WO2008/135991, U.S. Pat. No. 6,391,683, U.S. patent application Ser. No. 10/784,295; International Patent Publications PCT Nos. WO2004/091475, WO2005/080544 and WO 2006/040761, all of which are hereby incorporated by reference as if fully set forth herein.

Thus, the invention encompasses plants or plant cultures expressing the nucleic acid sequences, so as to produce the TNFα polypeptide inhibitor of the invention. Once expressed within the plant cell or the entire plant, the level of the TNFα inhibitor encoded by the nucleic acid sequence can be determined by methods well known in the art such as, activity assays, Western blots using antibodies capable of specifically binding the TNFα inhibitor e.g., chimeric polypeptide (anti TNFR2, and anti Fc, See Examples section which follows), Enzyme-Linked Immuno Sorbent Assay (ELISA), radio-immuno-assays (RIA), immunohistochemistry, immunocytochemistry, immunofluorescence and the like.

Methods of determining the level in the plant of the RNA transcribed from the nucleic acid sequence are well known in the art and include, for example, Northern blot analysis, reverse transcription polymerase chain reaction (RT-PCR) analysis (including quantitative, semi-quantitative or real-time RT-PCR) and RNA-in situ hybridization.

According to some embodiments of the invention, the expressed recombinant chimeric polypeptide of the present invention is glycosylated in the plant cell, resulting in a chimeric polypeptide having one, or two or three or more glycan structures having plant specific glycan residues. Thus, according to some embodiments of the invention, the cells expressing the expression vector of the invention produce a chimeric polypeptide having various amounts of glycan structures arranged in one, two, three or more antennae. All structures may contain a core structure of two GlcNAcs and one mannose, and variations of different amounts of mannose, in addition to core alpha (1,3) fucose, beta (1,2) xylose, and/or GlcNAc residues. Structures can be of the high mannose type, having at least one, optionally at least two, optionally at least three or optionally at least four or more mannose residues in addition to the core structure; or complex type having both mannose and other glycan types on each glycan, or of the hybrid type having both high mannose and complex antennae. In other embodiments the cells expressing the expression vector of the invention produce a TNFα inhibitor having at least one, optionally at least two, optionally at least three or optionally at least four or more core xylose residues. In yet other embodiments the cells expressing the expression vector of the invention produce a TNFα inhibitor having at least one, optionally at least two, optionally at least three or optionally at least four or more core α-(1,3) fucose residues. In one embodiment the cells expressing the expression vector of the invention produce a TNFα inhibitor protein having at least one exposed mannose residue, at least one core xylose residue and at least one α-(1,3) fucose residue. In yet further embodiments, the cells expressing the expression vector of the invention produce a TNFα inhibitor having at least one, at least two, at least 3 or more terminal N-acetyl glucosamine substitutions on the outer mannose sugars.

According to a specific embodiment the TNFα inhibitor e.g., chimeric polypeptide, lacks sialic acid residues. Yet further according to a specific embodiment, the TNFα inhibitor e.g., chimeric polypeptide, comprises at least 40%, 45%, 50%, 55%, 60%, 65%, 70% or more complex glycans. According to a specific embodiment, the chimeric polypeptide comprises 40-70% complex glycans.

Plant cells expressing the TNFα polypeptide inhibitor of the invention is utilized for the treatment of TNFα-associated medical conditions.

It has been shown in Example 2 of the Examples section that plant cells expressing TNFα polypeptide inhibitor (e.g., chimeric polypeptide) can be used as an effective systemic delivery system, when provided for enteral administration to the subject (see WO2007/010533). Thus, in some embodiments, the TNFα polypeptide inhibitor can be formulated in a pharmaceutical composition for oral or enteral delivery comprising transformed plant cell expressing the chimeric polypeptide and a pharmaceutically acceptable carrier. In some embodiments, the transformed plant cells of the pharmaceutical composition are lyophilized plant cells, although the use of fresh (non-lyophilized cells), plant tissues, plant parts or whole plants is also contemplated herein.

Prior to lyophilization the cells may be washed to remove any cell debris that may be present in the growth medium.

As the cells are being prepared for lyophilization, it is sometimes desirable to incubate the cells in a maintenance medium to reduce the metabolic processes of the cells.

Pretreatment (although not necessary) can be performed at room temperature or at temperatures in which the plant cells are typically cultured. Pretreatment is performed at about room temperature (20° C.) for ease of handling and as most plant cells are fairly stable at room temperature. Stabilizers can be added directly to the medium and replenished as necessary during the pretreatment process.

Pretreatments may also involve incubating cells in the presence of one or more osmotic agents. Examples of useful osmotic agents include sugars such as saccharides and saccharide derivatives, amino or imino acids such as proline and proline derivatives, or combinations of these agents. Some of the more useful sugars and sugar derivatives are fructose, glucose, maltose, mannitol, sorbitol, sucrose and trehalose. Osmotic agents are utilized at a concentration that prepares cells for subsequent lyophilization.

Lyophilization is directed at reducing the water content of the cells by vacuum evaporation. Vacuum evaporation involves placing the cells in an environment with reduced air pressure. Depending on the rate of water removal desired, the reduced ambient pressure operating at temperatures of between about −30° C. to −50° C. may be at 100 torr, 1 torr, 0.01 torr or less. According to a specific embodiment, the cells are lyophilized by freezing to −40° C. and then applying a vacuum to a pressure of 0.1 mbar for overnight. The cells are then heated to −10° C. so all the ice content will be sublimated and evaporated. Under conditions of reduced pressure, the rate of water evaporation is increased such that up to 60-95% of the water in a cell can be removed.

According to a specific embodiment, lyophilization removes over 60%, 70%, 80% or specifically over 90%, 91%, 92%, 93%, 94%, 95% or 98% of the water from the cells. According to a specific embodiment, the final water content is about 5-10%, 5-8% or 6-7%.

As used herein the phrase "enteral administration" refers to administration through any part of the gastro-intestinal tract, such as rectal administration, colonic administration, intestinal administration (proximal or distal) and gastric administration. In some embodiments, enteral administration refers to oral administration. It will be appreciated that the present teachings also aim at mucosal administration.

The cells may be formulated as a solid, formulated as a liquid or formulated as a powder. In some embodiments, the cells are resuspended, lyophilized cells.

Thus, the oral dosage form may be provided as an oral nutritional form (e.g., as long as the protein is not exposed to denaturing conditions which include heating above 37° C. and compression), as a complete meal, as a powder for dissolution, e.g. health drinks, as a solution, as a ready-made drink, optionally low calorie, such as a soft drink, including juices, milk-shake, yoghurt drink, smoothie or soy-based drink, in a bar, or dispersed in foods of any sort, such as baked products, cereal bars, dairy bars, snack-foods, breakfast cereals, muesli, candies, tabs, cookies, biscuits, crackers (such as a rice crackers), chocolate, and dairy products.

The cells can be administered to the subject per se, or alternatively, the cells of the present invention can be administered to the subject in a pharmaceutical composition where they are mixed with suitable carriers or excipients.

As used herein, a "pharmaceutical composition" refers to a preparation of cells expressing TNFalpha inhibitor with other chemical components such as physiologically suitable carriers and excipients. The purpose of a pharmaceutical composition is to facilitate administration of a compound to an organism.

As used herein, the term "active ingredient" refers to the cells expressing TNFalpha inhibitor accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases. Preferably the carrier used is a non-immunogenic carrier and further preferably does not stimulate the gut associated lymphatic tissue.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added.

The dosage forms may include additives such as one or more of calcium, magnesium, iron, zinc, phosphorus, vitamin D and vitamin K. A suitable daily amount is 0.1 mg to 3.6 g calcium, preferably 320 to 530 mg. In general, the daily dosage of vitamins and minerals in the nutritional formulation or medicament of the invention is 25-100% by weight of the dosages recommended by the health authorities. Dietary fiber may also be a component of the compositions of the invention. Further components of the supplement may include any bioactive compounds or extracts which are known to have health benefits, especially for improving physical performance.

Generally the unit dosage form may further comprise an antioxidant (exemplary embodiments are provided above. In another embodiment, the antioxidant is a pharmaceutically acceptable antioxidant. In another embodiment, the antioxidant is selected from the group consisting of vitamin E, superoxide dismutase (SOD), omega-3, and beta-carotene.

In another embodiment, the unit dosage form further comprises an enhancer of the biologically active protein or peptide. In another embodiment, the unit dosage form further comprises a cofactor of the biologically active protein or peptide.

In another embodiment, a unit dosage form of the present invention further comprises pharmaceutical-grade surfactant. Surfactants are well known in the art, and are described, inter alia, in the Handbook of Pharmaceutical Excipients (eds. Raymond C Rowe, Paul J Sheskey, and Sian C Owen, copyright Pharmaceutical Press, 2005). In another embodiment, the surfactant is any other surfactant known in the art.

In another embodiment, a unit dosage form of the present invention further comprises pharmaceutical-grade emulsifier or emulgator (emollient). Emulsifiers and emulgators are well known in the art, and are described, inter alia, in the Handbook of Pharmaceutical Excipients (ibid). Non-limiting examples of emulsifiers and emulgators are eumulgin, Eumulgin B1 PH, Eumulgin B2 PH, hydrogenated castor oil cetostearyl alcohol, and cetyl alcohol. In another embodiment, the emulsifier or emulgator is any other emulsifier or emulgator known in the art.

In another embodiment, a unit dosage form of the present invention further comprises pharmaceutical-grade stabilizer. Stabilizers are well known in the art, and are described, inter alia, in the Handbook of Pharmaceutical Excipients (ibid). In another embodiment, the stabilizer is any other stabilizer known in the art.

In another embodiment, a unit dosage form of the present invention further comprises an amino acid selected from the group consisting of arginine, lysine, aspartate, glutamate, and histidine. In another embodiment, analogues and modified versions of arginine, lysine, aspartate, glutamate and histidine are included in the terms "arginine," "lysine," "aspartate", "glutamate" and "histidine," respectively. In another embodiment, the amino acid provides additional protection of ribonuclease or other active molecules. In another embodiment, the amino acid promotes interaction of biologically active protein or peptide with a target cell. In another embodiment, the amino acid is contained in an oil component of the unit dosage form.

In another embodiment, a unit dosage form of the present invention further comprises one or more pharmaceutically acceptable excipients, into which the matrix carrier unit dosage form is mixed. In another embodiment, the excipients include one or more additional polysaccharides. In another embodiment, the excipients include one or more waxes. In another embodiment, the excipients provide a desired taste to the unit dosage form. In another embodiment, the excipients influence the drug consistency, and the final dosage form such as a gel capsule or a hard gelatin capsule.

Non limiting examples of excipients include: Antifoaming agents (dimethicone, simethicone); Antimicrobial preservatives (benzalkonium chloride, benzelthonium chloride, butylparaben, cetylpyridinium chloride, chlorobutanol, chlorocresol, cresol, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Chelating agents (edetate disodium, ethylenediaminetetraacetic acid and salts, edetic acid); Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (*acacia*, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Polymers (e.g., cellulose acetate, alkyl celluloses, hydroxyalkylcelluloses, acrylic polymers and copolymers); Suspending and/or viscosity-increasing agents (*acacia*, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); This list is not meant to be exclusive, but instead merely representative of the classes of excipients and the particular excipients which may be used in oral dosage unit dosage forms of the present invention.

Conventional additives may be included in the compositions of the invention, including any of those selected from preservatives, chelating agents, effervescing agents, natural or artificial sweeteners, flavoring agents, coloring agents, taste masking agents, acidulants, emulsifiers, thickening agents, suspending agents, dispersing or wetting agents, antioxidants, and the like. Flavoring agents can be added to the compositions of the invention to aid in compliance with a dosing regimen. Typical flavoring agents include, but are not limited to natural or synthetic essences, oils and/or extracts of pineapple, orange, lemon, mint, berry, chocolate, vanilla and melon.

The amount of a composition to be administered will, of course, be dependent on the subject being treated, the severity of the affliction, the manner of administration, the judgment of the prescribing physician, etc.

In another embodiment the effective chimeric polypeptide amount per adult dose range is about 0.0002 mg/kg to 2 mg/kg, about 0.002-2 mg/kg, about 0.02-2 mg/kg, about 0.2-2 mg/kg, about 0.002-0.2 mg/kg, about 0.0002-1 mg/kg, about 0.002-0.1 mg/kg, about 0.002-0.02 mg/kg, about 0.002-0.01 mg/kg, about 0.002-0.008 mg/kg, about 0.02-0.1 mg/kg, about 0.001-0.05 mg/kg, about 0.001-0.01 mg/kg, about 0.01-1 mg/kg, about 0.01-15 mg/kg, about 0.005-1 mg/kg, about 0.01-5 mg/kg, about 0.005-0.01 mg/kg or about 0.05-0.1 mg/kg. According to a specific embodiment, the effective chimeric polypeptide amount per adult dose ranges about 0.002-0.2 mg/kg.

According to a specific embodiment, a flat dose of 0.01-100 mg, 0.1-100 mg, 0.1-50 mg, 0.1-20 mg, 0.1-10 mg, 0.1-5 mg is administered.

According to a specific embodiment the flat dose is about 0.1-10 mg.

According to a specific embodiment, the oral dose is administered daily. The dose may be divided for a number of administrations during the day (say 2-4 times a day). The dose can also be administered every two days, two times a week, three times a week, biweekly, weekly doses, or separated by several weeks (for example 2 to 8).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology"

Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1, 2, 317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Experimental Procedures

Expression Constructs and Expression cDNA encoding prh TNFR2:Fc was optimized and synthesized by GENEART AG (Regensburg, Germany). The codon usage was adapted to the codon bias of *Nicotiana tabacum* genes. The IgG1 portion was cloned from Fc IgG1 heavy chain constant region [*Homo sapiens*] ACCESSION AEV43323.

During the optimization process the following cis-acting sequence motifs were avoided: Internal TATA-boxes, chi-sites and ribosomal entry sites, AT-rich or GC-rich sequence stretches, RNA instability elements ("Killer motifs"), Repeat sequences and RNA secondary structures, splice donor (cryptic) and acceptor sites, branch points. In addition, regions of very high (>80%) or very low (<30%) GC content were avoided. The resultant DNA sequence is as set forth in SEQ ID NO: 1. The encoded polypeptide is as set forth in SEQ ID NO: 2. To the native cDNA sequence, a signal peptide (e.g. endoplasmic reticulum target signal peptide) from *N. plumbaginifolia* Calreticulin protein was added to the N' terminus of the gene, allowing efficient targeting of Prh TNFR2:Fc to the secretory pathway and is then cleaved from the polypeptide, by signal peptidase, once the protein has been translocated into the endoplasmic reticulum (SEQ ID NO: 3, SEQ ID NO: 4, representing the DNA and peptide sequences of the ER signal peptide, respectively). Additionally, an ER retention signal SEKDEL was added to the C' terminus of the gene. This signal allows protein retrieval from the Golgi apparatus to the ER, and localization in the ER. The entire coding sequence (signal peptide-prh TNFR2:Fc-SEKDEL) is encoded by SEQ ID NO: 5 and the encoded polypeptide is as set forth in SEQ ID NO: 6. The resultant protein following cleavage of the N-terminal signal peptide is as set forth in SEQ ID NO: 7, 204 or 205 (prh TNFR2:Fc-SEKDEL).

Stable Expression in *N. tabacum* BY2 Cells

*Agrobacterium* mediated transformation is widely used to introduce foreign genes into a plant cell genome. Using this approach, a T-DNA molecule consisting of a foreign gene and its regulatory elements is randomly introduced into the plant genome. Since the site of integration, as well as the copy number of the gene insertions cannot be controlled, the transformation process results in a highly heterogeneous transgenic ‘pool’ composed of cells with various levels of transgene expression. The transgenic ‘pool’ is subsequently used for clone isolation. The transformation process, results in establishment of numerous single cell lines, each representing an individual transformation event, from which the clone with the highest expression level of the foreign gene is selected. For prh TNFR2:Fc (PRH TNFR2:FC) the transformation was conducted with a plasmid carrying the prh TNFR2:Fc cassette (FIG. 1 SEQ ID NOs: 7 and 8). As a result, the recombinant protein is targeted to the Endoplasmic reticulum (ER) of the cells. The transformations of the BY2 cells with the PRH TNFR2:FC-ER expression vector were performed by the *Agrobacterium tumefaciens* mediated plant transformation procedure as follow: BY2 (Bright Yellow 2) suspension culture was co-cultivated, for 48 hours, with the *Agrobacterium tumefaciens* strain carrying the vector harboring the prhTNFR2:FC-gene and the neomycin phosphotransferase (NPTII) selection gene. Subsequently, cells were kept in media supplemented with 50 mg/L of Kanamaycin and 250 mg/L Cefotaxime. The NPTII gene confers resistance to Kanamycin, thus only NPTII positive BY2 cells survive in this selection media. The Cefotaxime was used to selectively kill the *agrobacterium*, the plant cells being resistant to this antibiotic.

Screening for the Optimal Expressing Clone

In order to select individual cell lines, aliquots of highly diluted cell suspension were spread on solid BY-2 medium (Toshiyuki Nagata & Fumi Kumagai *Methods in Cell Science* 21: 123-127, 1999). The cells were then grown until small calli developed. Each callus was then re-suspended in liquid culture. Cells were then sampled and evaluated for PRH TNFR2:FC. About 500 cell line were screened by Western blot under denaturing conditions (FIG. 4). The lines with high expression levels were further re-analyzed by the same method to select the highest expressing clone of prh TNFR2:FC producing clone.

Gel Electrophoresis:

Sodium Dodecyl Sulfate-Polyacrylamide Gel Electrophoresis (SDS-PAGE) separates proteins on an electrical field according to their size. Proteins in the presence of the detergent SDS migrate as a linear function of the logarithm of their molecular weight. Migration pattern and identification of PRH TNFR2:FC on SDS-PAGE was compared to commercial molecular weight standard proteins (New England BioLabs; cat No. P7708S) and to the commercially available, mammalian-cell derived Enbrel® expressed in CHO cells (Entanercept; Wyeth). PRH TNFR2:FC was extracted from cells either by reducing sample buffer containing β-mercaptoethanol or by native extraction buffer. The native extraction supernatant was mixed with non-reducing sample buffer prior to analysis. Electrophoresis was performed using Criterion™ cell vertical electrophoresis apparatus (Bio-Rad Lab.) with premixed electrophoresis Tris-Glycine-SDS running buffer (Bio-Rad Laboratories). Following electrophoresis, the proteins were transferred from the Polyacrylamide gel to a protein binding nitrocellulose membrane (iBlot™). Membranes were blocked for 1 hr at RT with 5% milk buffer containing 0.1% Tween 20. For identification of the Fc portion of the molecule, Goat anti human IgG conjugated to HRP (cat #109-035-098, Jackson.)

was used. For TNFR2 detection, a Rabbit Anti-TNFRII (ID: ab109853, Abcam) followed by Goat anti Rabbit HRP (cat #111-035-003, Jackson) were employed. Detection was carried out with ECL detection kit (Pierce). The immunoreactivity of PRH TNFR2:FC was compared to that of commercial Enbrel® (Entanercept; Wyeth). Bands were detected using the Molecular Imager Gel Doc XR System (Bio-Rad Laboratories).

Amino Acid Sequencing by Mass-Spectrometry prhTNFR2:FC is sent for sequencing analysis at the Smoler Proteomics Center at the Technion—Israel Institute of Technology (Haifa, Israel). The protein is extracted from the gel, reduced with 2.8 mM DTT (60° C. for 30 min), modified with 8.8 mM iodoacetamide in 100 mM ammonium bicarbonate (in the dark, room temperature for 30 min) and digested in 10% ACN and 10 mM ammonium bicarbonate with modified Trypsin (Promega) or with ChymoTrypsin overnight at 37° C. in a 1:50 enzyme-to-substrate ratio. 3% of the resulting peptides are resolved by reverse-phase chromatography on 0.075×200-mm fused silica capillaries (J&W) packed with Reprosil reversed phase material (Dr Maisch GmbH, Germany). The peptides are eluted with linear 60 minutes gradients of 5 to 45% and 15 minutes at 95% acetonitrile with 0.1% formic acid in water at flow rates of 0.25 μl/min. On line mass spectrometry is performed by an ion-trap mass spectrometer (Orbitrap, Thermo) in a positive mode using repetitively full MS scan followed by collision induces dissociation (CID) of the 7 most dominant ion selected from the first MS scan.

The mass spectrometry data is analyzed using the Sequest 3.31 software (J. Eng and J. Yates, University of Washington and Finnigan, San Jose) vs a specific sequence.

Glycosylation Analysis

The major difference between glycoproteins produced in Chinese Hamster Ovary (CHO) cell and plant cell systems is the glycosylation profile and glycan structure. Preliminary analysis has been performed to characterize the various N-linked glycan structures attached to the protein. These results are compared to results of the N-glycosylation profile found in commercial Enbrel®. The presence of O-linked glycans, and glycan site analysis is determined.

Samples of PRH TNFR2:FC and commercial Enbrel are reduced, alkylated and separated on SDS-PAGE. The protein bands at ~75 KDa (a total of about 200 μg protein) are taken for glycan analysis using trypsin digestion followed by either PNGase A or PNGase F digestion (~80% and ~20% of the total protein, respectively) for PRH TNFR2:FC and PNGase F digestion only for commercial Enbrel. Digestion with Trypsin, followed by PNGase A releases all the N-linked glycans and digestion with PNGase F releases all glycans except those containing alpha 1-3 core fucose (found in plants). The released glycans are extracted, cleaned and then labeled with the fluorescent reagent anthranilamide (2-aminobenzamide, 2AB) followed by removal of excess 2AB. The analytical method includes separation of the glycans on a Waters HPLC system with a normal phase amide-based column (Tosoh TSK Amide-80 column), coupled with a fluorescence detector (330 nm excitation, 420 nm emission). Sequencing of the labeled glycan pool is achieved by sequential digestion with various exoglycosidases followed by additional HPLC analysis. Using sequential digestion with various exoglycosidases provides additional information on the profile of the glycans structures and their relative amounts. The exoglycosidase digestions that are carried out for the glycans released from PRH TNFR2:FC are with JBH (Jack bean beta-N-Acetylhexosaminidase) that removes beta 1-2, 3, 4 and 6 N-acetyl-glucosamine (GlcNAc), with JBM (Jack bean mannosidase) that removes mannose alpha 1-2, 6>3 mannose and with BKF (Bovine testis fucosidase) that removes alpha 1-6 and alpha 1-3 core fucose. The fluorescence labeling enables a semi-quantitative analysis of the distribution of the various glycan structures in the total digested glycan pool. The glycans are then separated according to unique glycan linkages and in order of increasing size using a gradient solvent flow consisting of ammonium formate and acetonitrile. Retention time of individual glycans is compared to the retention times of a standard mix of partially hydrolysed dextran fragments, giving a ladder of glucose units (GU). The glycans are assigned to peaks according to their GU values, based on standards and a comparison to an external data base (glycobase website 8080). The final assignment and relative peak areas are calculated from the chromatogram of the PNGase A digestion.

Enzyme-Linked Immunosorbent Assay (ELISA)

Binding ELISA:

TNFα binding ELISA is a combination of a commercial TNFα detection ELISA kit (Human TNF-α; Hycult Biotech Inc. #HK307) and a commercial anti human IgG antibody (Goat anti human IgG FC specific HRP; Sigma). The assay is a quantitative non radioactive assay for prhTNFR2:FC binding activity. This binding ELISA enables to detect functional (capable of binding TNFα) molecules comprising both the TNFR and IgG domains.

An ELISA plate pre-coated with antibodies against TNFα was incubated with TNFα (60 ng/ml, Sigma) for 1 hour at room temperature. Between each ELISA step the plate was washed three times with commercial wash buffer. Commercial Enbrel and supernatant from BY2 cells expressing PRH TNFR2:FC (serial dilutions) were incubated on ELISA plate for 2 hr at RT. Goat anti human IgG Fc HRP was diluted 1:10,000 and incubated on plate for 1 hr at RT. TMB was used as substrate for HRP. The colorimetric reaction was stopped with 10% HCL and absorbance determined at 450 nm.

Prevention of TNF α Induced Apoptosis in A375 Cells

A375 cells (human melanoma cells) were grown in suspension in culture medium (ATCC, #30-2002, supplemented with 10% FBS). $10^4$/well cells were plated in 96-well assay plates and incubated overnight in assay medium (ATCC, #30-2002, supplemented with 5% FBS). Recombinant TNFα (2 ng/ml, ProSpec, Rehovot, Israel) was incubated for 2 hr at 37° C. in the presence of different concentrations (1.562-100 ng/ml) of prhTNFR2:FC or commercial Enbrel (Entanercept; Wyeth). Following incubation, the mixed solution was added to A375 cells in the presence of actinomycin-D (0.8 μg/ml), incubated for further 24 hr at 37° C., 5% $CO_2$ in a humidified incubator and quantification of apoptosis was determined by MTT assay (Sigma Cat. No. M5655). The plate was read at 570-650 nm and the inhibition of TNF-α induced cytotoxicity (%) was calculated.

Example 2

Protein Analysis prhTNFR2:FC was analyzed under reducing (FIG. 2A) and non-reducing conditions (native extraction in the FIG. 2B). prhTNFR2:FC (Lane 1) and commercial Enbrel (lane 2) were detected using anti Fc antibody (upper panel) and anti TNFR2 antibody (lower panel). The two proteins demonstrate a slight difference in migration characteristics, presumably due to differences in glycosylation patterns between the plant and mammalian cell-expressed enzymes.

TNFα binding by both commercial Enbrel and prh TNFR2:FC was examined by comparing serial dilutions of BY2 cells expressing prh TNFR2:Fc (PRX-106) lysates to commercial Enbrel. prh TNFR2:FC serial dilutions demonstrate a dose response binding pattern similar to the commercial protein (see FIG. 3). The selection of transgenic cell lines according to protein expression was done by Western blotting. Thus, to allow for the selection of individual cell lines, aliquots of highly diluted cell suspension were spread on solid BY-2 medium. The cells were then grown until small calli developed. Each callus was then re-suspended in liquid culture. Cells were then sampled and evaluated for prh TNFR2:Fc expression levels by extraction under reducing conditions followed by Western Blot identification (anti FC antibody) of the produced target protein (FIG. 4). The functionality of the expressed protein was established by its ability to prevent TNFα induced apoptosis. Specifically, TNFα activity can be measured by its ability to induce cell death of certain cell lines in the presence of the transcriptional inhibitor, actinomycin D. Pre-incubation with a neutralizing protein of TNFα prevents binding to the receptors (TNF-R1 and TNF-R2), thereby inhibiting the cytokine effect and preventing TNFα induced cell death. Quantification of cell viability by MTT assay provides an in-cell activity assay for TNFα cytotoxicity. The results are shown in FIGS. 5A-G on melanoma cells A375 and in FIGS. 6A-G on L929 fibroblasts.

Example 3

Oral Administration of Plant Cells Expressing Recombinant TNFR2:Fc Effectively Reduces Hepatotoxicity in the Con A Immune-Mediated Hepatatis Model The Concanavalin A (Con A) model is well established animal model for investigating T-cell, Natural killer (NK) T cells (NKT) and macrophage dependent liver injury, which closely mimics the pathogenesis and pathological changes characteristic to Immune-Mediated Hepatitis. Amelioration of hepatotoxicity by oral administration of plant cells expressing recombinant TNFR2:Fc in this model of immune-mediated hepatitis provides evidence for effective anti-inflammatory capabilities of the plant cells expressing a recombinant TNFR2:Fc.

Materials and Methods

Animals:

Male, C57Bl/6 mice, 11-12 weeks old were used in all experiments. Each experimental group included 5 to 8 mice.

Con A Model:

Concanavalin A (MP Biomedicals, OH, USA), dissolved in 50 mM Tris (pH 7), 150 mM sodium chloride, 4 mM $CaCl_2$ was administered intravenously into the tail vein at a dose of 20 mg/Kg body weight. Mice were sacrificed 14 hours after Con A administration and blood samples were collected by cardiac puncture, allowed to coagulate and serum removed for determination of serum liver enzymes (alanine aminotranferase, ALT and aspartate aminotransferase, AST) and cytokine (IFN-gamma) levels. Livers were excised and prepared for histopathological evaluation (see below).

Oral Administration of Recombinant Plant Cells:

Oral administration of plant cells expressing recombinant TNFR2:Fc was initiated 6 hours before administration of Con A. Mice received plant cells expressing recombinant TNFR2:Fc, equivalent to 0.5 μg (X1) or 5 μg (X10) TNFR2: Fc protein, freshly prepared by emulsification in saline. Negative controls received the same orally administered volumes of host BY2(-) plant cells, in place of the plant cells expressing recombinant TNFR:Fc. Oral administration was performed by gavage in a volume of 350 μl.

Steroid Controls:

Steroid treatment was provided by oral administration of 035 mg Dexamethasone (Teva, Israel) per mouse, 6 hours prior to the administration of Con A.

Hepatotoxicity:

Liver enzymes (alanine aminotranferase, ALT and aspartate aminotransferase, AST), markers of damage to the liver parenchyma, were evaluated in serum using a Reflovet Plus clinical chemistry analyzer (Roche Diagnostics, Mannheim Germany). Cytokine (IFN-gamma) levels were evaluated in the serum of the treated and control mice by ELISA, using the Quantikine Colorimetric Sandwich ELISA kit (R&D Systems, Minneapolis Minn., USA).

Pathology:

Histopathology was determined in individual livers after fixation of the tissue in 10% formaldehyde and storage at room temperature, embedding in paraffin, sectioning and staining with hematoxylin and eosin (H&E) for morphological and histological examination by light microscopy.

Results:

In three separate series of experiments, oral administration of plant cells expressing recombinant TNFR2:Fc, at both low doses (equivalent to 0.5 μg TNFR2:Fc protein "X1") and higher doses (equivalent to 5 μg TNFR2:Fc protein "X10") significantly reduced the hepatotoxic effects of Con A. Elevation of serum enzyme markers of liver damage (AST, ALT) was largely prevented in all three experiments (see FIGS. 7A, 7B and 7C), with efficacy approaching that of oral steroid treatment (FIGS. 8A, 8B and 8C, Dex.).

Determination of the cytokine IFN-gamma in serum of the mice 14 hours after Con A administration (see FIGS. 8A, 8B and 8C) also revealed a significant reduction in serum IFN-gamma in the groups receiving oral administration of plant cells expressing recombinant TNFR2:Fc, at both low doses (equivalent to 0.5 μg TNFR2:Fc protein "X1") and higher doses (equivalent to 5 μg TNFR2:Fc protein "X10").

Histopathological evaluation (hematoxylin and eosin) of the livers of treated and control mice (FIGS. 9A, 9B and 9C) revealed severe hepatic necrosis in the control livers (FIG. 9A), but preservation of liver architecture and normal liver histology in the livers of the mice treated with plant cells expressing recombinant TNFR2:Fc (FIG. 9B).

Oral administration of plant cells expressing recombinant TNFR2:Fc (low dose, equivalent to 0.5 μg TNFR2:Fc protein) and intraperitoneal administration of 100 μg of the commercial mammalian cell expressed TNFR2:Fc Etanercept (ENBREL®, Wyeth) were compared for their effect on hepatotoxicity in the Con A immune-mediated hepatitis model. Comparing levels of serum liver damage markers AST and ALT in the treated mice, relative to untreated controls revealed that even a low dose of the plant cells expressing recombinant TNFR2:Fc, orally administered, was as effective (87-85%, FIGS. 10A and 10B) as 100 μg of Etanercept administered intraperitoneally in preventing elevation of liver damage markers in response to Con A-induced immune-mediated hepatitis.

Example 4

Oral Administration of Plant Cells Expressing Recombinant TNFR2:Fc Effectively Ameliorates Immuno-Pathogenesis in Fatty Liver Disease Modeled by High Fat Diet (HFD)

A well accepted animal model of fatty liver disease is induced by High Fat Diet (HFD). Mice with diet-induced obesity are characterized by elevated serum lipid profile, increased hepatic triglycerides and immune system alterations.

The effect of orally administered plant cells expressing recombinant TNFR2:Fc on mice fed with HFD was determined. Analysis included the effect of the treatment on clinical manifestations of the disease and as an immunomodulator.

Materials and Methods

Animals:

Male C57bl/6 mice, 6-7 weeks old were used in all experiments. Each experimental group included 10 mice. The mice were purchased from Harlan Laboratories, Jerusalem, Israel. All mice were fed with HFD (Harlan, TD88137 in which 42% of calories are from fat) from day 0 until their sacrifice, after 24 weeks.

TABLE 1

(Experimental design):

| Group | N | High fat diet | Treatment |
|---|---|---|---|
| A | 10 | + | PO 35 µl Saline 3 days a week |
| B | 10 | + | PO, 28.8 mg BY– (mock cells), 3 days a week |
| C | 10 | + | PO, 2.88 mg (0.5 µg TNF) BY+ 3 days a week |
| D | 10 | + | PO, 2.88 mg (10 µg anti TNF) BY+ 3 days a week |

Oral Administration of Recombinant Plant Cells:

Oral administration of plant cells expressing recombinant TNFR:Fc (batch Ly013+) was initiated 3 times a week. Negative controls received the same orally administered dose of mock cells (BY–). All oral administrations to mice were in a total volume of 35 µl. Fresh preparations were made before each administration.

Endpoint Measured on a Weekly Basis:
1. Body weight

Endpoints Measured on a Once-a Month Basis:
1. Fasting blood glucose levels
2. Serum ALT, AST levels*
3. Serum triglycerides levels*

Monitoring of serum liver enzymes and triglycerides was by measuring the Reflovet Plus clinical chemistry analyzer (Roche Diagnostics, GmbH, Mannheim, Germany).

Additional Endpoints:
1. Fasting serum Insulin levels on day 1 and on week 24 (ELISA).
2. Glucose tolerance test (GTT) on week 8 and on week 24.
3. Liver fat content (triglycerides); after sacrifice
4. Liver histology, after sacrifice
5. Serum cytokine levels (TNF-α), after sacrifice (ELISA).
6. Flow cytometry (FACS) for subsets of T cells and Tregs (spleen and liver).
7. CD8-APC/CD4-FITC/CD25-PE/Foxp3-PE-Cy7
8. CD3-FITC/NK 1.1-APC Following Sacrifice of the Mice (at Week 24):

Cytokine Secretion:

Cytokine (TNF-α) levels were measured in the serum of treated and control mice by ELISA, using the Quantikine Sandwich ELISA Kit (R&D Systems, Minneapolis, Minn., USA).

Histopathology:

Livers were excised and then fixed in 10% formaldehyde, embedded in paraffin, sectioned and stained with H&E and with Mason trichome (for fibrosis). H&E tissues were examined and scored by light microscopy for morphological and histo-pathological changes characteristic for NASH by a blinded pathologist.

Triglyceride Determination:

Accumulation of intracellular triglycerides (TG) within the liver was quantified using a modification of the Folch method. TG were extracted from aliquots of snap-frozen livers and then assayed spectrophotometrically using the GPO-Trinder kit (Sigma, Rehovot, Israel) and normalized to the protein content in the homogenate.

FACS analysis was performed for subsets of T cells and Tregs taken from spleen.

Results

The effect of orally administered plant cells expressing recombinant TNFR2:Fc on serum enzymes was tested. As can be seen in FIG. 11, oral administration of the cells expressing the inhibitor, caused a decrease in AST levels in the treated mice, as measured on sacrifice day (week 24). A trend of decrease in ALT levels was also evident (data not shown).

The effect of orally administered plant cells expressing recombinant TNFR2:Fc on serum triglycerides (TG) was tested. As can be seen in FIGS. 12A-B, oral administration of the cells expressing the inhibitor, caused a significant decrease in TG levels in the treated mice, on sacrifice day (week 24). Importantly, the results obtained support therapeutic efficacy of the TNFR2:Fc, since the effect on serum enzymes and TGs was evident despite persistant gain weight in all groups tested (FIG. 13).

Next the distribution of T cell subpopulation in the liver and spleen of the model mice was tested by histopathology and FACS. FIG. 14 shows the results of hepatic Tregs. As can be seen, intra hepatic Tregs significantly decreased in the high dose treated mice.

FIG. 15 shows the results of hepatic NK cells. As can be seen, intra hepatic NK cells significantly increased in the high dose treated mice.

FIG. 16 shows the results of the effect of oral administration of plant cells expressing recombinant TNFR2:Fc on splenic/hepatic CD4+CD25+FOXP3+ ratio. As can be seen, an increase in the ratio of spleen to liver for Tregs (CD4+ CD25+FOXP3+) was noted. 0.5 µg of PRX-106 increased this ratio by 10% and 10 µg of PRX-106 increased this ratio by 22%, compared to saline-treated mice.

FIG. 17 shows the results of the effect of oral administration of recombinant TNFR2:Fc in plant cells on splenic/ hepatic CD8+CD25+FOXP3+ ratio. As can be seen, a considerable increase in the ratio of spleen to liver was noted for another subset of cells: CD8+CD25+FOXP3+ cells. Low dose of 0.5 µg of the drug increased this ratio by 74% compared to saline-treated mice.

These results suggest that oral administration of recombinant TNFR2:Fc in plant cells alters the T cells distribution affecting the intrahepatic to periphery (splenic) T cell functions in HFD mice modeling a fatty liver disease.

Example 5

Toxicology Studies in Mice

Methods

Animals

Male and female SD Rats (Harlan Laboratories, Israel) 8 weeks at study initiation were housed under standard laboratory conditions. Mean weight at study initiation was approximately 6.8 gr for males and 6.3 gr for females. Animals were fed with commercial rodent diet (Teklad Certified Global 18% Protein Diet cat #: 2018SC) and had free access to autoclaved and acidified drinking water (pH between 2.5 and 3.5).

Study Design

Four groups, 3 dosing groups comprising 12 rats per group (6 males and 6 females) and a control group comprising 6 rats per group (3 males and 3 females), were assigned. In each gender, the control group received dilution buffer (0.2 M mannitol) and three treated groups received cells expressing TNFR2:Fc at dose levels of 0.1, 0.5 and 1 mg TNFR2:Fc/Kg body weight. Cells were alliquoted in accordance with requested expressed protein amount. Each aliquot was mixed with 30 grams powder of commercial rodent diet and dilution buffer, to create a pellet. The control pellet was made with dilution buffer and commercial rodent diet powder alone. All animals were daily orally fed with the pellets for 14 days. During the study, mortality and general clinical observation were performed, bodyweight was monitored daily. At study termination (Day 15) after light anesthesia with carbon dioxide inhalation, three blood samples were drawn from all animals from the retro orbital sinus gross, after which, animals were sacrificed, pathology was executed and selected organs were harvested.

Results

No adverse clinical symptoms were recorded throughout the 14-day safety study. All blood parameters were within the normal range with no significant deviations. Body weight gain was persistent and normal with no significant difference between the groups (treated or Control). Cells expressing were found to be safe and well tolerated with no adverse effects. No effect on biochemical parameters or clinical symptoms was found. Gross necropsy observation did not reveal pathological findings. No animal was found in a moribund state or under severe distress conditions. There were no observations of animals presenting severe pain or decreased body weight.

Example 6

Sequencing of PRX-106

N Terminus Sequencing by Edman Degradation

Analysis was performed at Alphalyse (Denmark) uainf, an ABI Procise 494 sequencer. The procedure determines the N-terminal amino acid sequence of proteins and peptides by the Edman degradation chemistry. The Edman degradation is a cyclic procedure where amino acid residues are cleaved off one at a time and identified by chromatography. Here are 3 steps in the cyclic procedure. In step 1, the PITC reagent is coupled to the N-terminal amino group under alkaline conditions. In step 2, the N-terminal residue is cleaved in acidic media. In step 3, the PITC coupled residue is transferred to a flask, converted to a PTH-residue and identified by HPLC chromatography. The next cycle is then started for identification of the next N-terminal residue.

Results:

The sequence was determined to be LPAQV (SEQ ID NO: 18).

Amino Acid Sequence Verification by Reverse Phase HPLC Coupled to a Mass Spectrometry Detector.

Sequencing was performed at the Smoler Proteomics Center (Technion—Israel Institute of Technology, Haifa, Israel). Analyses were carried out using reverse-phase HPLC coupled to a mass spectrometry detector.

Method

Proteolysis

The analyzed samples were resuspended in 8 M Urea, 100 mM ammonium bicabonate (ABC) followed by reduction with 2.8 mM DTT (60° C. for 30 min) and modified with 8.8 mM iodoacetamide in 100 mM ABC in the dark, at ambient temperature for an additional 30 min. The proteins were digested overnight at 37° C. using modified trypsin (Promega) at a 1:50 enzyme-to-substrate ratio in 2 M Urea, 25 mM ABC.

Mass Spectrometry Analysis

The tryptic or chymotryptic peptides were desalted using stage tips (home-made C18), the residual buffer was evaporated and the pellet was resuspended in 0.1% (v/v) formic acid. Twenty nanogram of the resulting peptides were resolved by reversed-phase liquid chromatography on a 0.075×200-mm fused silica capillaries (J and W) packed with Reprosil reversed phase material (Dr Maisch GmbH, Germany). Peptides were eluted with a linear 60 minutes gradient of 5 to 45% followed by 15 minutes at 95% acetonitrile with 0.1% formic acid in water at flow rates of 0.25 μL/min. On-line mass spectrometry was performed on an ion-trap mass spectrometer (Orbitrap, Thermo) in a positive mode using repetitively full MS scan followed by collision induced dissociation (CID) of the 7 most dominant ions selected from the first MS scan. The mass spectrometry data was analyzed using the Discoverer software version 1.3 software using a specific protein derived database.

Results

The sequence was compared to the peptide sequence of the Etanercept sequence. The identified sequences are presented in Table V, below.

TABLE V

Peptides Identified Following Digestion with Trypsin (SEQ ID NO: 19-203, ordered)

WQQGnVFScSVMHEALHnHYTQK

WQQGNVFScSVMHEALHNHYTqK

GFYPSDIAVEWESNGqPENnYKT qYNSTYRVVSVLTVLHqDWLNGK

WQqGNVFScSVMHEALHNHYTqKS

VVSVLTVLHQDWLNGKEYKc

VVSVLTVLHqDWLnGKEYK

SqHTqPTPEPSTAPSTSFLLPmGPSPPAEGSTGDEPK

WQQGnVFScSVMHEALHNHY

ScDKTHTcPPcPAPELLGGPSVFLFPPKPKD

GQPREPqVYTLPPSREEMTK

GFYPSDIAVEWESNGQPEnNYKT

LPAqVAFTPYAPEPGSTcR

EALHnHYTqK qNRIcTcRPGWYcALSKQEGcR

WQQGNVFScSVmHEALHnHYTQK

SqHTQPTPEPSTAPSTSFLLPMGPSPPAEGSTGDEPK

GQPREPqVYTLPPSREEmTK

TABLE V-continued

Peptides Identified Following Digestion with Trypsin (SEQ ID NO: 19-203, ordered)

GFYPSDIAVEWESnGQPENNYK

SqHTQPTPEPSTAPSTSFLLPmGPSPPAEGSTGDEPK

VVSVLTVLHQDWLnGK

TYTqLWNWVPEcLScGSRcSSDqVETQAcTR

WQQGNVFScSVMHEALHNHYTQK

GFYPSDIAVEWESnGQPEnnYKT

VVVDVSHEDPEVK

PSTSFLLPMGPSPPAEGSTGDEPK

LPAQVAFTPYAPEPGSTcR

TTPPVLDSDGSFFL

LSLSPGK

EPQVYTLPPSREEMTKN

SmAPGAVHLPQ

TTPPVLDSDGSFFLYSK

WQQGNVFScSVmHEALHNHYTQK

SMAPGAVH

SVmHEALHNHYTQK

VVSVLTVLH

SQHTQPTPEPSTAPSTSFLLPMGPSPPAEGSTGDEPK

GQPREPQVY

AQVAFTPYAPEPGSTcR cAPLRK

EPQVYTLPPSREEmTKnQVSLTcLVK

SmAPGAVH

VVSVLTVLHQD

LFPPKPK

GSFFLYSK

IcTcRPGWY

SQHTQPTPEPS

SVLTVLHQDWLnGKEYK

QVETQAcTR

SLSLSPGK

SDGSFFLYSK

KALPAPIEK

ALPAPIEK

AVcTSTSPTR

SQHTQPTPEPSTAPSTSF

QVSLTcLVK

LREYYDQTAqmccSKcSPGQHAK

WQQGNVFScSVMHEALH

DTLmISR

PmGPSPPAEGSTGDEPK

THTcPPcPAPELLGGPSVF

DTLMISR

SDQVETQAcTR

KcRPGFGVAR

WYVDGVEVHNAK

YVDGVEVHNAK

TTPPVLDSDGSFF

THTcPPcPAPELLGGPSVFLFPPKPK

PSPPAEGSTGDEPK

SLSLSPGKSEKD

MAPGAVHLPQPVSTR

VDGVEVHNAK

ScDKTHTcPPcPAPELLGGPSVF

VVSVLTVLHQDWLNGK

SLSLSPGKSEK

PPcPAPELLGGPSVFLFPPKPK

SFFLYSK

FNWYVDGVEVHNAK

FLLPMGPSPPAEGSTGDEPK

DAVcTSTSPTR

NQVSLIcLVK

NqVSLTcLVKG

SLSPGKSEK

TPEVTcVVVDVSHEDPEVK

LREYYDQTAQM

GFYPSDIAVEWESNGQPENNYK

FNWYVDGVEVHN

VVSVLTVLHQDWLN

SQHTQPTPEPSTAPST

RTPEVTcVVVDVSHEDPEVK

SLSLSPGKS

LSPGKSEKDEL

LPQPVSTR

TTPPVLDSDGSFFLY

TSDTVcDScEDSTYTQLWN

TABLE V-continued

Peptides Identified Following Digestion with Trypsin (SEQ ID NO: 19-203, ordered)

ALPAQVAFTPYAPEPGSTcR

EEQYNSTYR

ScDKTHTcPPcPAPELLGGPSVFLFPPKPK cSPGQHAKVFcTK

TPEVTcVVVDVSHED

SMAPGAVHLPQPV

TcRPGWYcALSK

TcPPcPAPELLGGPSVFLFPPKPK

TSDTVcDScEDSTYTQLWNWVPEcLScGSR

LcAPLRK

SPPAEGSTGDEPK

WVPEcLScGSR

GPSPPAEGSTGDEPK

SSDQVETQAcTR

EEQYnSTYR

VAFTPYAPEPGSTcR

PGWYcALSK cRPGFGVAR

ScSVmHEALHnHYTqK

VVSVLTVLHQDWLNGKEYK

LcAPLR

EPQVYTLPPSREEMTKnQVSLTcLVK

LLPMGPSPPAEGSTGDEPK

SQHTQPTPEPSTAPSTSFLLPmGPSPPAEGSTGDEPK

SLSLSPGKSE

EEMTKNqV

SVMHEALHNHYTQK

SQHTQPTPEPSTAPSTSFLLPMGPSPPAEGSTGDEPKScDK

EEmTKnQVSLTcLVKG

LREYYDQTAQmccSK cSSDqVETQAcTR

EPQVYTLPPSREEMTK

NQVSLTcLVKG cSSDQVETQAcTR nQVSLTcLVK

TKPREEQYNSTYR

PAQVAFTPYAPEPGSTcR

SLSLSPGKSEKDEL

AFTPYAPEPGSTcR

APGAVHLPQPVSTR

SDGSFFLYSKLTVDK

THTcPPcPAPELLG

VVSVLTVLHQDWLn

EPQVYTLPPSR

SmAPGAVHLPQPVSTR

GQPREPQVYTLPPSREEmTK

TPYAPEPGSTcR

EVTcVVVDVSHEDPEVK

TKPREEQYnSTYR

VSnKALPAPIEK

LREYYDQTAQMccSK

FTPYAPEPGSTcR

SMAPGAVHLPQPVSTR

GPSVFLFPPKPK

VVSVLTVLHQDWLnGKEYK

SQHTQPTPEPSTAPS

SMAPGAVHLPQPVS

AVHLPQPVSTR

GQPREPQVYTLPPSR

PGAVHLPQPVSTR

TLMISR

KNqVSLTcLVKGFYPSDIAVEWESNGqPENnYK

LREYYDQTAQMc

SmAPGAVHLPQPV

LPAPIEK

EYYDQTAQMccSK

NWVPEcLScGSR

SLSPGKSEKDEL

IcTcRPGWYcALSK

SMAPGAVHLPQPVST

EYYDQTAQmccSK

ASMDAVcTSTSPTR

SQHTQPTPEPSTAPSTS

TLPPSREEMTK

SQHTQPTPEPSTAPSTSFL

TLmISR

EPQVYTLPPSREEmTK

TABLE V-continued

Peptides Identified Following Digestion with
Trypsin (SEQ ID NO: 19-203, ordered)

GQPREPQVYTLPPSREEMTK

TPEVTcVVVDVSHEDPEVKFN

ScDKTHTcPPcPAPELLG

GFYPSDIAVEWESNGqPENnYK

AKGQPREPQVYTLPPSR

LREYYDQTAQMcc

LPmGPSPPAEGSTGDEPK

ScSVMHEALHNHYTQK

FNWYVDGVEVHnAK

PMGPSPPAEGSTGDEPK

SMAPGAVHLPQPVSTR

SMAPGAVHLPQ

LPMGPSPPAEGSTGDEPK

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a TNFα associated liver disease or disorder, the method comprising enterally administering to a subject in need thereof a therapeutically effective amount of plant cells expressing a TNFα polypeptide inhibitor, wherein said TNFα polypeptide inhibitor is a chimeric polypeptide comprising:
 (i) a first domain comprising a TNFα binding domain of TNFR2; and
 (ii) a second domain comprising an Fc domain of an immunoglobulin,
 wherein the chimeric polypeptide is TNFR2:Fc,
 thereby treating the TNFα associated liver disease or disorder.

2. The method of claim 1, wherein said enteral is oral administration.

3. The method of claim 1, wherein
 the carboxy terminus of said first domain is translationally fused to the N-terminus of the second domain and wherein the chimeric polypeptide specifically binds TNFα.

4. The method of claim 3, wherein said chimeric polypeptide further comprises a third domain which comprises an endoplasmic reticulum retention signal, wherein the carboxy terminus of the second domain is translationally fused to the N-terminus of the third domain.

5. The method of claim 3, comprising an additional domain encoding an endoplasmic reticulum signal peptide, wherein the carboxy terminus of the endoplasmic reticulum signal peptide is translationally fused to the N-terminus of said first domain.

6. The method of claim 5, wherein said signal peptide is a plant signal peptide.

7. The method of claim 6, wherein said plant signal peptide is set forth in the amino acid sequence of SEQ ID NO: 4.

8. The method of claim 3, wherein said first domain is 200-250 amino acids long.

9. The method of claim 8, wherein said first domain comprises the amino acid sequence LCAP (SEQ ID NO: 11) and VFCT (SEQ ID NO: 12).

10. The method of claim 9, wherein said first domain further comprises the amino acid sequence LPAQVAFX-PYAPEPGSTC (SEQ ID NO: 13).

11. The method of claim 10, wherein said first domain is set forth in the amino acid sequence of SEQ ID NO: 2.

12. The method of claim 3, wherein said second domain is set forth in the amino acid sequence of SEQ ID NO: 9.

13. The method of claim 3, wherein said chimeric polypeptide is set forth in the amino acid sequence of SEQ ID NO: 6.

14. The method of claim 4, wherein said chimeric polypeptide is set forth in the amino acid sequence of any one of SEQ ID NO: 7, 204 or 205.

15. The method of claim 3, wherein said chimeric polypeptide is capable of inhibiting TNFα-induced apoptosis.

16. The method of claim 1, wherein said TNFα polypeptide inhibitor comprises a plant-specific glycan.

17. The method of claim 1, wherein said plant cells are *Nicotiana tabacum* plant cells.

18. The method of claim 17, wherein said *Nicotiana tabacum* plant cell is a Bright Yellow (BY-2) cell.

19. The method of claim 1, wherein said plant cells are lyophilized.

20. The method of claim 1, wherein said plant cells are grown in suspension.

21. The method of claim 1, wherein said liver disease or disorder is selected from the group consisting of hepatitis, liver cirrhosis, liver cancer, hepatotoxicity, chronic liver disease, fatty liver disease and non-alcoholic steatohepatitis (NASH).

22. The method of claim 1, wherein said plant cells are provided in an oral nutritional form.

23. The method of claim 1, wherein said TNFα polypeptide inhibitor reduces a serum enzyme or a metabolite.

24. The method of claim 4, wherein said chimeric polypeptide is set forth in the amino acid sequence of SEQ ID NO: 7.

* * * * *

SEQUENCE LISTING

<160> NUMBER OF SEQ ID NOS: 205

<210> SEQ ID NO 1
<211> LENGTH: 705
<212> TYPE: DNA
<213> ORGANISM: Artificial sequence
<220> FEATURE:
<223> OTHER INFORMATION: DNA encoding a TNFR2 derived sequence

<400> SEQUENCE: 1

```
cttccagctc aggttgcttt tactccatat gctccggagc caggatctac ttgtaggctt      60
agggaatact acgatcagac tgctcaaatg tgctgctcta agtgctctcc aggacagcac     120
gctaaggttt tctgcactaa gacttcagat actgtttgcg attcttgcga ggattctact     180
tacactcagc tttggaattg ggttccagag tgtctttctt gtggatctag gtgctcttct     240
gatcaggttg agactcaggc ttgtactagg gagcagaata ggatttgtac ttgcaggcca     300
ggatggtatt gtgctctttc taagcaagag ggatgtaggc tttgtgctcc acttagaaag     360
tgcaggcctg gttttggagt tgctagacca ggaactgaga cttctgacgt tgtttgcaag     420
ccatgtgctc caggaacttt ctctaatact acttcttcta ctgatatttg caggccacat     480
caaatttgca atgttgttgc tattccaggt aatgcttcta tggatgctgt ttgcacttct     540
acttctccaa ctaggtctat ggctccagga gctgttcatc ttccacaacc agtttctact     600
aggtcacaac atactcagcc aactccagaa ccatctactg ctccatctac ttcattcctt     660
ttgccaatgg gaccatctcc accagctgaa ggatctactg gagat                     705
```

<210> SEQ ID NO 2
<211> LENGTH: 235
<212> TYPE: PRT
<213> ORGANISM: Artificial sequence
<220> FEATURE:
<223> OTHER INFORMATION: TNFR2 derived sequence

<400> SEQUENCE: 2

```
Leu Pro Ala Gln Val Ala Phe Thr Pro Tyr Ala Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
                35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235

<210> SEQ ID NO 3
<211> LENGTH: 81
<212> TYPE: DNA
<213> ORGANISM: Artificial sequence
<220> FEATURE:
<223> OTHER INFORMATION: N. plumbaginifolia Calreticulin protein
      derived signal peptide encoding sequence

<400> SEQUENCE: 3
atggctactc aaaggagggc taatccatct tctcttcatc ttattactgt tttctctctt      60
cttgttgctg ttgtttctgc a                                               81

<210> SEQ ID NO 4
<211> LENGTH: 27
<212> TYPE: PRT
<213> ORGANISM: Artificial sequence
<220> FEATURE:
<223> OTHER INFORMATION: N. plumbaginifolia Calreticulin protein
      derived signal peptide

<400> SEQUENCE: 4

Met Ala Thr Gln Arg Arg Ala Asn Pro Ser Ser Leu His Leu Ile Thr
1               5                   10                  15

Val Phe Ser Leu Leu Val Ala Val Val Ser Ala
            20                  25

<210> SEQ ID NO 5
```

<211> LENGTH: 1506
<212> TYPE: DNA
<213> ORGANISM: Artificial sequence
<220> FEATURE:
<223> OTHER INFORMATION: prh TNFR2:Fc (PRX106) encoding sequence

<400> SEQUENCE: 5

```
atggctactc aaaggagggc taatccatct tctcttcatc ttattactgt tttctctctt      60
cttgttgctg ttgtttctgc acttccagct caggttgctt ttactccata tgctccggag     120
ccaggatcta cttgtaggct tagggaatac tacgatcaga ctgctcaaat gtgctgctct     180
aagtgctctc caggacagca cgctaaggtt ttctgcacta agacttcaga tactgtttgc     240
gattcttgcg aggattctac ttacactcag cttcggaatt gggttccaga gtgtctttct     300
tgtggatcta ggtgctcttc tgatcaggtt gagactcagg cttgtactag ggagcagaat     360
aggatttgta cttgcaggcc aggatggtat tgtgctcttt ctaagcaaga gggatgtagg     420
ctttgtgctc cacttagaaa gtgcaggcct ggttttggag ttgctagacc aggaactgag     480
acttctgacg ttgtttgcaa gccatgtgct ccaggaactt ctctaatac tacttcttct     540
actgatattt gcaggccaca tcaaatttgc aatgttgttg ctattccagg taatgcttct     600
atggatgctg tttgcacttc tacttctcca actaggtcta tggctccagg agctgttcat     660
cttccacaac cagtttctac taggtcacaa catactcagc caactccaga accatctact     720
gctccatcta cttcattcct tttgccaatg ggaccatctc caccagctga aggatctact     780
ggagatgagc caaagtcttg cgataagact catacttgtc caccatgtcc agctccagaa     840
cttcttggag gaccatctgt tttccttttc ccaccaaagc caaggatac tcttatgatt     900
tctaggactc cagaggttac ttgcgttgtt gttgatgttt cacatgaaga tccagaggtg     960
aagttcaatt ggtacgttga tggagttgag gttcataatg ctaagactaa gccaagggag    1020
gagcaataca attcaacata cagggttgtt tctgttctta ctgttcttca tcaagattgg    1080
cttaatggaa aggaatacaa gtgcaaggtt tctaataagg ctttgccagc accaattgaa    1140
aagactattt ctaaggctaa gggacaacca agagagccac aagtttacac tcttccacca    1200
tctagggagg agatgactaa gaatcaagtt ctctcttactt gccttgttaa gggattctac    1260
ccatctgata ttgctgttga gtgggagtct aacggacagc ctgagaataa ttacaagact    1320
actccaccag ttcttgattc tgatggatct tccttccttt actctaagtt gactgttgat    1380
aagtctaggt ggcaacaggg aaatgttttc tcttgctctg ttatgcatga ggctcttcat    1440
aatcattaca ctcagaaatc actttctctt tctccaggta agagtgagaa ggacgagctc    1500
tgatga                                                               1506
```

<210> SEQ ID NO 6
<211> LENGTH: 500
<212> TYPE: PRT
<213> ORGANISM: Artificial sequence
<220> FEATURE:
<223> OTHER INFORMATION: prh TNFR2:Fc (PRX106) polypeptide

<400> SEQUENCE: 6

Met Ala Thr Gln Arg Arg Ala Asn Pro Ser Ser Leu His Leu Ile Thr
1               5                   10                  15

Val Phe Ser Leu Leu Val Ala Val Ser Ala Leu Pro Ala Gln Val
                20                  25                  30

Ala Phe Thr Pro Tyr Ala Pro Glu Pro Gly Ser Thr Cys Arg Leu Arg
                35                  40                  45

-continued

```
Glu Tyr Tyr Asp Gln Thr Ala Gln Met Cys Cys Ser Lys Cys Ser Pro
    50                  55                  60

Gly Gln His Ala Lys Val Phe Cys Thr Lys Thr Ser Asp Thr Val Cys
65                  70                  75                  80

Asp Ser Cys Glu Asp Ser Thr Tyr Thr Gln Leu Trp Asn Trp Val Pro
                85                  90                  95

Glu Cys Leu Ser Cys Gly Ser Arg Cys Ser Ser Asp Gln Val Glu Thr
            100                 105                 110

Gln Ala Cys Thr Arg Glu Gln Asn Arg Ile Cys Thr Cys Arg Pro Gly
        115                 120                 125

Trp Tyr Cys Ala Leu Ser Lys Gln Glu Gly Cys Arg Leu Cys Ala Pro
    130                 135                 140

Leu Arg Lys Cys Arg Pro Gly Phe Gly Val Ala Arg Pro Gly Thr Glu
145                 150                 155                 160

Thr Ser Asp Val Val Cys Lys Pro Cys Ala Pro Gly Thr Phe Ser Asn
                165                 170                 175

Thr Thr Ser Ser Thr Asp Ile Cys Arg Pro His Gln Ile Cys Asn Val
            180                 185                 190

Val Ala Ile Pro Gly Asn Ala Ser Met Asp Ala Val Cys Thr Ser Thr
        195                 200                 205

Ser Pro Thr Arg Ser Met Ala Pro Gly Ala Val His Leu Pro Gln Pro
    210                 215                 220

Val Ser Thr Arg Ser Gln His Thr Gln Pro Thr Pro Glu Pro Ser Thr
225                 230                 235                 240

Ala Pro Ser Thr Ser Phe Leu Leu Pro Met Gly Pro Ser Pro Pro Ala
                245                 250                 255

Glu Gly Ser Thr Gly Asp Glu Pro Lys Ser Cys Asp Lys Thr His Thr
            260                 265                 270

Cys Pro Pro Cys Pro Ala Pro Glu Leu Leu Gly Gly Pro Ser Val Phe
        275                 280                 285

Leu Phe Pro Pro Lys Pro Lys Asp Thr Leu Met Ile Ser Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
```

```
                                465                 470                 475                 480
Asn His Tyr Thr Gln Lys Ser Leu Ser Leu Ser Pro Gly Lys Ser Glu
                                485                 490                 495

Lys Asp Glu Leu
            500

<210> SEQ ID NO 7
<211> LENGTH: 473
<212> TYPE: PRT
<213> ORGANISM: Artificial sequence
<220> FEATURE:
<223> OTHER INFORMATION: prh TNFR2:Fc (PRX106) mature polypeptide

<400> SEQUENCE: 7

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
        50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
```

```
                325                 330                 335
Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys Ser Glu Lys Asp Glu Leu
465                 470

<210> SEQ ID NO 8
<211> LENGTH: 696
<212> TYPE: DNA
<213> ORGANISM: Artificial sequence
<220> FEATURE:
<223> OTHER INFORMATION: IgG1-FC encoding sequence

<400> SEQUENCE: 8
gagccaaagt cttgcgataa gactcatact tgtccaccat gtccagctcc agaacttctt     60
ggaggaccat ctgttttcct tttcccacca agcccaaagg atactcttat gatttctagg    120
actccagagg ttacttgcgt tgttgttgat gtttcacatg aagatccaga ggtgaagttc    180
aattggtacg ttgatggagt tgaggttcat aatgctaaga ctaagccaag ggaggagcaa    240
tacaattcaa catacagggt tgtttctgtt cttactgttc ttcatcaaga ttggcttaat    300
ggaaaggaat acaagtgcaa ggtttctaat aaggctttgc cagcaccaat tgaaaagact    360
atttctaagg ctaagggaca accaagagag ccacaagttt acactcttcc accatctagg    420
gaggagatga ctaagaatca gtttctcttt cttgccttgt taagggattt ctacccatct    480
gatattgctg ttgagtggga gtctaacgga cagcctgaga taattacaa gactactcca     540 ccagttcttg attctgatgg atcttctctt ctttactcta gttgactgt tgataagtct     600 aggtggcaac agggaaatgt tttctcttgc tctgttatgc atgaggctct tcataatcat    660
tacactcaga aatcactttc tcttctccca ggtaag                              696

<210> SEQ ID NO 9
<211> LENGTH: 232
<212> TYPE: PRT
<213> ORGANISM: Artificial sequence
<220> FEATURE:
<223> OTHER INFORMATION: IgG1-FC

<400> SEQUENCE: 9

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 10
<211> LENGTH: 467
<212> TYPE: PRT
<213> ORGANISM: Artificial sequence
<220> FEATURE:
<223> OTHER INFORMATION: Etanercept polypeptide

<400> SEQUENCE: 10

Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160
```

-continued

```
Gln Ile Cys Asn Val Val Ala Ile Pro Gly Asn Ala Ser Met Asp Ala
                165                 170                 175
Val Cys Thr Ser Thr Ser Pro Thr Arg Ser Met Ala Pro Gly Ala Val
            180                 185                 190
His Leu Pro Gln Pro Val Ser Thr Arg Ser Gln His Thr Gln Pro Thr
        195                 200                 205
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp Glu Pro Lys Ser Cys
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 11
<211> LENGTH: 4
<212> TYPE: PRT
<213> ORGANISM: Artificial sequence
<220> FEATURE:
<223> OTHER INFORMATION: TNFR2 derived sequence

<400> SEQUENCE: 11

Leu Cys Ala Pro
1

<210> SEQ ID NO 12
<211> LENGTH: 4
<212> TYPE: PRT
<213> ORGANISM: Artificial sequence
<220> FEATURE:
```

```
<223> OTHER INFORMATION: TNFR2 derived sequence

<400> SEQUENCE: 12

Val Phe Cys Thr
1

<210> SEQ ID NO 13
<211> LENGTH: 18
<212> TYPE: PRT
<213> ORGANISM: Artificial sequence
<220> FEATURE:
<223> OTHER INFORMATION: TNFR2 derived sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 13

Leu Pro Ala Gln Val Ala Phe Xaa Pro Tyr Ala Pro Glu Pro Gly Ser
1               5                   10                  15

Thr Cys

<210> SEQ ID NO 14
<211> LENGTH: 4
<212> TYPE: PRT
<213> ORGANISM: Artificial sequence
<220> FEATURE:
<223> OTHER INFORMATION: ER retention signal peptide

<400> SEQUENCE: 14

His Asp Glu Leu
1

<210> SEQ ID NO 15
<211> LENGTH: 4
<212> TYPE: PRT
<213> ORGANISM: Artificial sequence
<220> FEATURE:
<223> OTHER INFORMATION: ER retention signal peptide

<400> SEQUENCE: 15

Lys Asp Glu Leu
1

<210> SEQ ID NO 16
<211> LENGTH: 6
<212> TYPE: PRT
<213> ORGANISM: Artificial sequence
<220> FEATURE:
<223> OTHER INFORMATION: ER retention signal peptide

<400> SEQUENCE: 16

Ser Glu Lys Asp Glu Leu
1               5

<210> SEQ ID NO 17
<211> LENGTH: 18
<212> TYPE: PRT
<213> ORGANISM: Artificial Sequence
<220> FEATURE:
<223> OTHER INFORMATION: TNFR2 derived sequence

<400> SEQUENCE: 17

Leu Pro Ala Gln Val Ala Phe Thr Pro Tyr Ala Pro Glu Pro Gly Ser
1               5                   10                  15

Thr Cys
```

```
<210> SEQ ID NO 18
<211> LENGTH: 5
<212> TYPE: PRT
<213> ORGANISM: Artificial Sequence
<220> FEATURE:
<223> OTHER INFORMATION: Peptide degradation product derived from prh
      TNFR2:Fc (PRX106)

<400> SEQUENCE: 18

Leu Pro Ala Gln Val
1               5

<210> SEQ ID NO 19
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 19

Trp Gln Gln Gly Asn Val Phe Ser Cys Ser Val Met His Glu Ala Leu
1               5                   10                  15

His Asn His Tyr Thr Gln Lys
            20

<210> SEQ ID NO 20
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 20

Trp Gln Gln Gly Asn Val Phe Ser Cys Ser Val Met His Glu Ala Leu
1               5                   10                  15

His Asn His Tyr Thr Gln Lys
            20

<210> SEQ ID NO 21
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 21

Gly Phe Tyr Pro Ser Asp Ile Ala Val Glu Trp Glu Ser Asn Gly Gln
1               5                   10                  15

Pro Glu Asn Asn Tyr Lys Thr
            20

<210> SEQ ID NO 22
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 22

Gln Tyr Asn Ser Thr Tyr Arg Val Val Ser Val Leu Thr Val Leu His
1               5                   10                  15
```

Gln Asp Trp Leu Asn Gly Lys
            20

<210> SEQ ID NO 23
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 23

Trp Gln Gln Gly Asn Val Phe Ser Cys Ser Val Met His Glu Ala Leu
1               5                   10                  15

His Asn His Tyr Thr Gln Lys Ser
            20

<210> SEQ ID NO 24
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 24

Val Val Ser Val Leu Thr Val Leu His Gln Asp Trp Leu Asn Gly Lys
1               5                   10                  15

Glu Tyr Lys Cys
            20

<210> SEQ ID NO 25
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 25

Val Val Ser Val Leu Thr Val Leu His Gln Asp Trp Leu Asn Gly Lys
1               5                   10                  15

Glu Tyr Lys

<210> SEQ ID NO 26
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 26

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
            35

<210> SEQ ID NO 27
<211> LENGTH: 20
<212> TYPE: PRT
<213> ORGANISM: Artificial sequence -continued

```
<220> FEATURE:
<223> OTHER INFORMATION: Peptide degradation product derived from prh
      TNFR2:Fc (PRX106)

<400> SEQUENCE: 27

Trp Gln Gln Gly Asn Val Phe Ser Cys Ser Val Met His Glu Ala Leu
1               5                   10                  15

His Asn His Tyr
            20

<210> SEQ ID NO 28
<211> LENGTH: 31
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 28

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp
            20                  25                  30

<210> SEQ ID NO 29
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 29

Gly Gln Pro Arg Glu Pro Gln Val Tyr Thr Leu Pro Pro Ser Arg Glu
1               5                   10                  15

Glu Met Thr Lys
            20

<210> SEQ ID NO 30
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 30

Gly Phe Tyr Pro Ser Asp Ile Ala Val Glu Trp Glu Ser Asn Gly Gln
1               5                   10                  15

Pro Glu Asn Asn Tyr Lys Thr
            20

<210> SEQ ID NO 31
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 31

Leu Pro Ala Gln Val Ala Phe Thr Pro Tyr Ala Pro Glu Pro Gly Ser
1               5                   10                  15

Thr Cys Arg
```

```
<210> SEQ ID NO 32
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 32

Glu Ala Leu His Asn His Tyr Thr Gln Lys
1               5                   10

<210> SEQ ID NO 33
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 33

Gln Asn Arg Ile Cys Thr Cys Arg Pro Gly Trp Tyr Cys Ala Leu Ser
1               5                   10                  15

Lys Gln Glu Gly Cys Arg
            20

<210> SEQ ID NO 34
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 34

Trp Gln Gln Gly Asn Val Phe Ser Cys Ser Val Met His Glu Ala Leu
1               5                   10                  15

His Asn His Tyr Thr Gln Lys
            20

<210> SEQ ID NO 35
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 35

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
        35

<210> SEQ ID NO 36
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 36
```

```
Gly Gln Pro Arg Glu Pro Gln Val Tyr Thr Leu Pro Pro Ser Arg Glu
1               5                   10                  15

Glu Met Thr Lys
            20
```

<210> SEQ ID NO 37
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 37

```
Gly Phe Tyr Pro Ser Asp Ile Ala Val Glu Trp Glu Ser Asn Gly Gln
1               5                   10                  15

Pro Glu Asn Asn Tyr Lys
            20
```

<210> SEQ ID NO 38
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 38

```
Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
        35
```

<210> SEQ ID NO 39
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 39

```
Val Val Ser Val Leu Thr Val Leu His Gln Asp Trp Leu Asn Gly Lys
1               5                   10                  15
```

<210> SEQ ID NO 40
<211> LENGTH: 31
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 40

```
Thr Tyr Thr Gln Leu Trp Asn Trp Val Pro Glu Cys Leu Ser Cys Gly
1               5                   10                  15

Ser Arg Cys Ser Ser Asp Gln Val Glu Thr Gln Ala Cys Thr Arg
            20                  25                  30
```

<210> SEQ ID NO 41
<211> LENGTH: 23
<212> TYPE: PRT
<213> ORGANISM: Artificial sequence

```
<220> FEATURE:
<223> OTHER INFORMATION: Peptide degradation product derived from prh
      TNFR2:Fc (PRX106)

<400> SEQUENCE: 41

Trp Gln Gln Gly Asn Val Phe Ser Cys Ser Val Met His Glu Ala Leu
1               5                  10                  15

His Asn His Tyr Thr Gln Lys
            20

<210> SEQ ID NO 42
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 42

Gly Phe Tyr Pro Ser Asp Ile Ala Val Glu Trp Glu Ser Asn Gly Gln
1               5                  10                  15

Pro Glu Asn Asn Tyr Lys Thr
            20

<210> SEQ ID NO 43
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 43

Val Val Val Asp Val Ser His Glu Asp Pro Glu Val Lys
1               5                  10

<210> SEQ ID NO 44
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 44

Pro Ser Thr Ser Phe Leu Leu Pro Met Gly Pro Ser Pro Pro Ala Glu
1               5                  10                  15

Gly Ser Thr Gly Asp Glu Pro Lys
            20

<210> SEQ ID NO 45
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 45

Leu Pro Ala Gln Val Ala Phe Thr Pro Tyr Ala Pro Glu Pro Gly Ser
1               5                  10                  15

Thr Cys Arg

<210> SEQ ID NO 46
<211> LENGTH: 14
```

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 46

Thr Thr Pro Pro Val Leu Asp Ser Asp Gly Ser Phe Phe Leu
1               5                   10

<210> SEQ ID NO 47
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 47

Leu Ser Leu Ser Pro Gly Lys
1               5

<210> SEQ ID NO 48
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 48

Glu Pro Gln Val Tyr Thr Leu Pro Pro Ser Arg Glu Glu Met Thr Lys
1               5                   10                  15

Asn

<210> SEQ ID NO 49
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 49

Ser Met Ala Pro Gly Ala Val His Leu Pro Gln
1               5                   10

<210> SEQ ID NO 50
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 50

Thr Thr Pro Pro Val Leu Asp Ser Asp Gly Ser Phe Phe Leu Tyr Ser
1               5                   10                  15

Lys

<210> SEQ ID NO 51
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)
```

```
<400> SEQUENCE: 51

Trp Gln Gln Gly Asn Val Phe Ser Cys Ser Val Met His Glu Ala Leu
1               5                   10                  15

His Asn His Tyr Thr Gln Lys
            20

<210> SEQ ID NO 52
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 52

Ser Met Ala Pro Gly Ala Val His
1               5

<210> SEQ ID NO 53
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 53

Ser Val Met His Glu Ala Leu His Asn His Tyr Thr Gln Lys
1               5                   10

<210> SEQ ID NO 54
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 54

Val Val Ser Val Leu Thr Val Leu His
1               5

<210> SEQ ID NO 55
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 55

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
            20                  25                  30

Gly Asp Glu Pro Lys
            35

<210> SEQ ID NO 56
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)
```

```
<400> SEQUENCE: 56

Gly Gln Pro Arg Glu Pro Gln Val Tyr
1               5

<210> SEQ ID NO 57
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 57

Ala Gln Val Ala Phe Thr Pro Tyr Ala Pro Glu Pro Gly Ser Thr Cys
1               5                  10                  15

Arg

<210> SEQ ID NO 58
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 58

Cys Ala Pro Leu Arg Lys
1               5

<210> SEQ ID NO 59
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 59

Glu Pro Gln Val Tyr Thr Leu Pro Pro Ser Arg Glu Glu Met Thr Lys
1               5                  10                  15

Asn Gln Val Ser Leu Thr Cys Leu Val Lys
            20                  25

<210> SEQ ID NO 60
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 60

Ser Met Ala Pro Gly Ala Val His
1               5

<210> SEQ ID NO 61
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 61

Val Val Ser Val Leu Thr Val Leu His Gln Asp
```

<210> SEQ ID NO 62
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 62

Leu Phe Pro Pro Lys Pro Lys
1               5

<210> SEQ ID NO 63
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 63

Gly Ser Phe Phe Leu Tyr Ser Lys
1               5

<210> SEQ ID NO 64
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 64

Ile Cys Thr Cys Arg Pro Gly Trp Tyr
1               5

<210> SEQ ID NO 65
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 65

Ser Gln His Thr Gln Pro Thr Pro Glu Pro Ser
1               5                   10

<210> SEQ ID NO 66
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 66

Ser Val Leu Thr Val Leu His Gln Asp Trp Leu Asn Gly Lys Glu Tyr
1               5                   10                  15

Lys

<210> SEQ ID NO 67
<211> LENGTH: 9
<212> TYPE: PRT
<213> ORGANISM: Artificial sequence

```
<220> FEATURE:
<223> OTHER INFORMATION: Peptide degradation product derived from prh
      TNFR2:Fc (PRX106)

<400> SEQUENCE: 67

Gln Val Glu Thr Gln Ala Cys Thr Arg
1               5

<210> SEQ ID NO 68
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 68

Ser Leu Ser Leu Ser Pro Gly Lys
1               5

<210> SEQ ID NO 69
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 69

Ser Asp Gly Ser Phe Phe Leu Tyr Ser Lys
1               5                   10

<210> SEQ ID NO 70
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 70

Lys Ala Leu Pro Ala Pro Ile Glu Lys
1               5

<210> SEQ ID NO 71
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 71

Ala Leu Pro Ala Pro Ile Glu Lys
1               5

<210> SEQ ID NO 72
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 72

Ala Val Cys Thr Ser Thr Ser Pro Thr Arg
1               5                   10
```

```
<210> SEQ ID NO 73
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 73

Ser Gln His Thr Gln Pro Thr Pro Glu Pro Ser Thr Ala Pro Ser Thr
1               5                   10                  15

Ser Phe

<210> SEQ ID NO 74
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 74

Gln Val Ser Leu Thr Cys Leu Val Lys
1               5

<210> SEQ ID NO 75
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 75

Leu Arg Glu Tyr Tyr Asp Gln Thr Ala Gln Met Cys Cys Ser Lys Cys
1               5                   10                  15

Ser Pro Gly Gln His Ala Lys
            20

<210> SEQ ID NO 76
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 76

Trp Gln Gln Gly Asn Val Phe Ser Cys Ser Val Met His Glu Ala Leu
1               5                   10                  15

His

<210> SEQ ID NO 77
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 77

Asp Thr Leu Met Ile Ser Arg
1               5

<210> SEQ ID NO 78
```

```
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 78

Pro Met Gly Pro Ser Pro Pro Ala Glu Gly Ser Thr Gly Asp Glu Pro
1               5                   10                  15

Lys

<210> SEQ ID NO 79
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 79

Thr His Thr Cys Pro Pro Cys Pro Ala Pro Glu Leu Leu Gly Gly Pro
1               5                   10                  15

Ser Val Phe

<210> SEQ ID NO 80
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 80

Asp Thr Leu Met Ile Ser Arg
1               5

<210> SEQ ID NO 81
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 81

Ser Asp Gln Val Glu Thr Gln Ala Cys Thr Arg
1               5                   10

<210> SEQ ID NO 82
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 82

Lys Cys Arg Pro Gly Phe Gly Val Ala Arg
1               5                   10

<210> SEQ ID NO 83
<211> LENGTH: 12
<212> TYPE: PRT
<213> ORGANISM: Artificial sequence
<220> FEATURE:
<223> OTHER INFORMATION: Peptide degradation product derived from prh
```

```
                TNFR2:Fc (PRX106)

<400> SEQUENCE: 83

Trp Tyr Val Asp Gly Val Glu Val His Asn Ala Lys
1               5                   10

<210> SEQ ID NO 84
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 84

Tyr Val Asp Gly Val Glu Val His Asn Ala Lys
1               5                   10

<210> SEQ ID NO 85
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 85

Thr Thr Pro Pro Val Leu Asp Ser Asp Gly Ser Phe Phe
1               5                   10

<210> SEQ ID NO 86
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 86

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 87
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 87

Pro Ser Pro Pro Ala Glu Gly Ser Thr Gly Asp Glu Pro Lys
1               5                   10

<210> SEQ ID NO 88
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 88

Ser Leu Ser Leu Ser Pro Gly Lys Ser Glu Lys Asp
1               5                   10
```

<210> SEQ ID NO 89
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 89

Met Ala Pro Gly Ala Val His Leu Pro Gln Pro Val Ser Thr Arg
1               5                   10                  15

<210> SEQ ID NO 90
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 90

Val Asp Gly Val Glu Val His Asn Ala Lys
1               5                   10

<210> SEQ ID NO 91
<211> LENGTH: 23
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 91

Ser Cys Asp Lys Thr His Thr Cys Pro Pro Cys Pro Ala Pro Glu Leu
1               5                   10                  15

Leu Gly Gly Pro Ser Val Phe
            20

<210> SEQ ID NO 92
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 92

Val Val Ser Val Leu Thr Val Leu His Gln Asp Trp Leu Asn Gly Lys
1               5                   10                  15

<210> SEQ ID NO 93
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 93

Ser Leu Ser Leu Ser Pro Gly Lys Ser Glu Lys
1               5                   10

<210> SEQ ID NO 94
<211> LENGTH: 22
<212> TYPE: PRT
<213> ORGANISM: Artificial sequence

```
<220> FEATURE:
<223> OTHER INFORMATION: Peptide degradation product derived from prh
      TNFR2:Fc (PRX106)

<400> SEQUENCE: 94

Pro Pro Cys Pro Ala Pro Glu Leu Leu Gly Gly Pro Ser Val Phe Leu
1               5                   10                  15

Phe Pro Pro Lys Pro Lys
            20

<210> SEQ ID NO 95
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 95

Ser Phe Phe Leu Tyr Ser Lys
1               5

<210> SEQ ID NO 96
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 96

Phe Asn Trp Tyr Val Asp Gly Val Glu Val His Asn Ala Lys
1               5                   10

<210> SEQ ID NO 97
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 97

Phe Leu Leu Pro Met Gly Pro Ser Pro Pro Ala Glu Gly Ser Thr Gly
1               5                   10                  15

Asp Glu Pro Lys
            20

<210> SEQ ID NO 98
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 98

Asp Ala Val Cys Thr Ser Thr Ser Pro Thr Arg
1               5                   10

<210> SEQ ID NO 99
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)
```

```
<400> SEQUENCE: 99

Asn Gln Val Ser Leu Thr Cys Leu Val Lys
1               5                   10

<210> SEQ ID NO 100
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 100

Asn Gln Val Ser Leu Thr Cys Leu Val Lys Gly
1               5                   10

<210> SEQ ID NO 101
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 101

Ser Leu Ser Pro Gly Lys Ser Glu Lys
1               5

<210> SEQ ID NO 102
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 102

Thr Pro Glu Val Thr Cys Val Val Val Asp Val Ser His Glu Asp Pro
1               5                   10                  15

Glu Val Lys

<210> SEQ ID NO 103
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 103

Leu Arg Glu Tyr Tyr Asp Gln Thr Ala Gln Met
1               5                   10

<210> SEQ ID NO 104
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 104

Gly Phe Tyr Pro Ser Asp Ile Ala Val Glu Trp Glu Ser Asn Gly Gln
1               5                   10                  15

Pro Glu Asn Asn Tyr Lys
```

<210> SEQ ID NO 105
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 105

Phe Asn Trp Tyr Val Asp Gly Val Glu Val His Asn
1               5                   10

<210> SEQ ID NO 106
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 106

Val Val Ser Val Leu Thr Val Leu His Gln Asp Trp Leu Asn
1               5                   10

<210> SEQ ID NO 107
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 107

Ser Gln His Thr Gln Pro Thr Pro Glu Pro Ser Thr Ala Pro Ser Thr
1               5                   10                  15

<210> SEQ ID NO 108
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 108

Arg Thr Pro Glu Val Thr Cys Val Val Val Asp Val Ser His Glu Asp
1               5                   10                  15

Pro Glu Val Lys
            20

<210> SEQ ID NO 109
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 109

Ser Leu Ser Leu Ser Pro Gly Lys Ser
1               5

<210> SEQ ID NO 110
<211> LENGTH: 11
<212> TYPE: PRT

```
<213> ORGANISM: Artificial sequence
<220> FEATURE:
<223> OTHER INFORMATION: Peptide degradation product derived from prh
      TNFR2:Fc (PRX106)

<400> SEQUENCE: 110

Leu Ser Pro Gly Lys Ser Glu Lys Asp Glu Leu
1               5                   10

<210> SEQ ID NO 111
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 111

Leu Pro Gln Pro Val Ser Thr Arg
1               5

<210> SEQ ID NO 112
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 112

Thr Thr Pro Pro Val Leu Asp Ser Asp Gly Ser Phe Phe Leu Tyr
1               5                   10                  15

<210> SEQ ID NO 113
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 113

Thr Ser Asp Thr Val Cys Asp Ser Cys Glu Asp Ser Thr Tyr Thr Gln
1               5                   10                  15

Leu Trp Asn

<210> SEQ ID NO 114
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 114

Ala Leu Pro Ala Gln Val Ala Phe Thr Pro Tyr Ala Pro Glu Pro Gly
1               5                   10                  15

Ser Thr Cys Arg
            20

<210> SEQ ID NO 115
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)
```

```
<400> SEQUENCE: 115

Glu Glu Gln Tyr Asn Ser Thr Tyr Arg
1               5

<210> SEQ ID NO 116
<211> LENGTH: 30
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 116

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30

<210> SEQ ID NO 117
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 117

Cys Ser Pro Gly Gln His Ala Lys Val Phe Cys Thr Lys
1               5                   10

<210> SEQ ID NO 118
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 118

Thr Pro Glu Val Thr Cys Val Val Val Asp Val Ser His Glu Asp
1               5                   10                  15

<210> SEQ ID NO 119
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 119

Ser Met Ala Pro Gly Ala Val His Leu Pro Gln Pro Val
1               5                   10

<210> SEQ ID NO 120
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 120

Thr Cys Arg Pro Gly Trp Tyr Cys Ala Leu Ser Lys
1               5                   10
```

```
<210> SEQ ID NO 121
<211> LENGTH: 24
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 121

Thr Cys Pro Pro Cys Pro Ala Pro Glu Leu Leu Gly Gly Pro Ser Val
1               5                   10                  15

Phe Leu Phe Pro Pro Lys Pro Lys
            20

<210> SEQ ID NO 122
<211> LENGTH: 30
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 122

Thr Ser Asp Thr Val Cys Asp Ser Cys Glu Asp Ser Thr Tyr Thr Gln
1               5                   10                  15

Leu Trp Asn Trp Val Pro Glu Cys Leu Ser Cys Gly Ser Arg
            20                  25                  30

<210> SEQ ID NO 123
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 123

Leu Cys Ala Pro Leu Arg Lys
1               5

<210> SEQ ID NO 124
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 124

Ser Pro Pro Ala Glu Gly Ser Thr Gly Asp Glu Pro Lys
1               5                   10

<210> SEQ ID NO 125
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 125

Trp Val Pro Glu Cys Leu Ser Cys Gly Ser Arg
1               5                   10

<210> SEQ ID NO 126
<211> LENGTH: 15
```

```
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 126

Gly Pro Ser Pro Pro Ala Glu Gly Ser Thr Gly Asp Glu Pro Lys
1               5                   10                  15

<210> SEQ ID NO 127
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 127

Ser Ser Asp Gln Val Glu Thr Gln Ala Cys Thr Arg
1               5                   10

<210> SEQ ID NO 128
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 128

Glu Glu Gln Tyr Asn Ser Thr Tyr Arg
1               5

<210> SEQ ID NO 129
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 129

Val Ala Phe Thr Pro Tyr Ala Pro Glu Pro Gly Ser Thr Cys Arg
1               5                   10                  15

<210> SEQ ID NO 130
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 130

Pro Gly Trp Tyr Cys Ala Leu Ser Lys
1               5

<210> SEQ ID NO 131
<211> LENGTH: 9
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 131

Cys Arg Pro Gly Phe Gly Val Ala Arg
```

<210> SEQ ID NO 132
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 132

Ser Cys Ser Val Met His Glu Ala Leu His Asn His Tyr Thr Gln Lys
1               5                   10                  15

<210> SEQ ID NO 133
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 133

Val Val Ser Val Leu Thr Val Leu His Gln Asp Trp Leu Asn Gly Lys
1               5                   10                  15

Glu Tyr Lys

<210> SEQ ID NO 134
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 134

Leu Cys Ala Pro Leu Arg
1               5

<210> SEQ ID NO 135
<211> LENGTH: 26
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 135

Glu Pro Gln Val Tyr Thr Leu Pro Pro Ser Arg Glu Glu Met Thr Lys
1               5                   10                  15

Asn Gln Val Ser Leu Thr Cys Leu Val Lys
            20                  25

<210> SEQ ID NO 136
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 136

Leu Leu Pro Met Gly Pro Ser Pro Ala Glu Gly Ser Thr Gly Asp
1               5                   10                  15

Glu Pro Lys

<210> SEQ ID NO 137
<211> LENGTH: 37
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 137

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

Gly Asp Glu Pro Lys
        35

<210> SEQ ID NO 138
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 138

Ser Leu Ser Leu Ser Pro Gly Lys Ser Glu
1               5                   10

<210> SEQ ID NO 139
<211> LENGTH: 8
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 139

Glu Glu Met Thr Lys Asn Gln Val
1               5

<210> SEQ ID NO 140
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 140

Ser Val Met His Glu Ala Leu His Asn His Tyr Thr Gln Lys
1               5                   10

<210> SEQ ID NO 141
<211> LENGTH: 41
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 141

Ser Gln His Thr Gln Pro Thr Pro Glu Pro Ser Thr Ala Pro Ser Thr
1               5                   10                  15

Ser Phe Leu Leu Pro Met Gly Pro Ser Pro Pro Ala Glu Gly Ser Thr
                20                  25                  30

```
Gly Asp Glu Pro Lys Ser Cys Asp Lys
        35                  40

<210> SEQ ID NO 142
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 142

Glu Glu Met Thr Lys Asn Gln Val Ser Leu Thr Cys Leu Val Lys Gly
1               5                   10                  15

<210> SEQ ID NO 143
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 143

Leu Arg Glu Tyr Tyr Asp Gln Thr Ala Gln Met Cys Cys Ser Lys
1               5                   10                  15

<210> SEQ ID NO 144
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 144

Cys Ser Ser Asp Gln Val Glu Thr Gln Ala Cys Thr Arg
1               5                   10

<210> SEQ ID NO 145
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 145

Glu Pro Gln Val Tyr Thr Leu Pro Pro Ser Arg Glu Glu Met Thr Lys
1               5                   10                  15

<210> SEQ ID NO 146
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 146

Asn Gln Val Ser Leu Thr Cys Leu Val Lys Gly
1               5                   10

<210> SEQ ID NO 147
<211> LENGTH: 13
<212> TYPE: PRT
<213> ORGANISM: Artificial sequence
<220> FEATURE:
```

```
<223> OTHER INFORMATION: Peptide degradation product derived from prh
      TNFR2:Fc (PRX106)

<400> SEQUENCE: 147

Cys Ser Ser Asp Gln Val Glu Thr Gln Ala Cys Thr Arg
1               5                   10

<210> SEQ ID NO 148
<211> LENGTH: 10
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 148

Asn Gln Val Ser Leu Thr Cys Leu Val Lys
1               5                   10

<210> SEQ ID NO 149
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 149

Thr Lys Pro Arg Glu Glu Gln Tyr Asn Ser Thr Tyr Arg
1               5                   10

<210> SEQ ID NO 150
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 150

Pro Ala Gln Val Ala Phe Thr Pro Tyr Ala Pro Glu Pro Gly Ser Thr
1               5                   10                  15

Cys Arg

<210> SEQ ID NO 151
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 151

Ser Leu Ser Leu Ser Pro Gly Lys Ser Glu Lys Asp Glu Leu
1               5                   10

<210> SEQ ID NO 152
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 152

Ala Phe Thr Pro Tyr Ala Pro Glu Pro Gly Ser Thr Cys Arg
1               5                   10
```

<210> SEQ ID NO 153
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 153

Ala Pro Gly Ala Val His Leu Pro Gln Pro Val Ser Thr Arg
1               5                   10

<210> SEQ ID NO 154
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 154

Ser Asp Gly Ser Phe Phe Leu Tyr Ser Lys Leu Thr Val Asp Lys
1               5                   10                  15

<210> SEQ ID NO 155
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 155

Thr His Thr Cys Pro Pro Cys Pro Ala Pro Glu Leu Leu Gly
1               5                   10

<210> SEQ ID NO 156
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 156

Val Val Ser Val Leu Thr Val Leu His Gln Asp Trp Leu Asn
1               5                   10

<210> SEQ ID NO 157
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 157

Glu Pro Gln Val Tyr Thr Leu Pro Pro Ser Arg
1               5                   10

<210> SEQ ID NO 158
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

```
<400> SEQUENCE: 158

Ser Met Ala Pro Gly Ala Val His Leu Pro Gln Pro Val Ser Thr Arg
1               5                   10                  15

<210> SEQ ID NO 159
<211> LENGTH: 20
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 159

Gly Gln Pro Arg Glu Pro Gln Val Tyr Thr Leu Pro Pro Ser Arg Glu
1               5                   10                  15

Glu Met Thr Lys
            20

<210> SEQ ID NO 160
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 160

Thr Pro Tyr Ala Pro Glu Pro Gly Ser Thr Cys Arg
1               5                   10

<210> SEQ ID NO 161
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 161

Glu Val Thr Cys Val Val Asp Val Ser His Glu Asp Pro Glu Val
1               5                   10                  15

Lys

<210> SEQ ID NO 162
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 162

Thr Lys Pro Arg Glu Glu Gln Tyr Asn Ser Thr Tyr Arg
1               5                   10

<210> SEQ ID NO 163
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 163

Val Ser Asn Lys Ala Leu Pro Ala Pro Ile Glu Lys
```

<210> SEQ ID NO 164
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 164

Leu Arg Glu Tyr Tyr Asp Gln Thr Ala Gln Met Cys Cys Ser Lys
1               5                   10                  15

<210> SEQ ID NO 165
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 165

Phe Thr Pro Tyr Ala Pro Glu Pro Gly Ser Thr Cys Arg
1               5                   10

<210> SEQ ID NO 166
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 166

Ser Met Ala Pro Gly Ala Val His Leu Pro Gln Pro Val Ser Thr Arg
1               5                   10                  15

<210> SEQ ID NO 167
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 167

Gly Pro Ser Val Phe Leu Phe Pro Pro Lys Pro Lys
1               5                   10

<210> SEQ ID NO 168
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 168

Val Val Ser Val Leu Thr Val Leu His Gln Asp Trp Leu Asn Gly Lys
1               5                   10                  15

Glu Tyr Lys

<210> SEQ ID NO 169
<211> LENGTH: 15
<212> TYPE: PRT
<213> ORGANISM: Artificial sequence

```
<220> FEATURE:
<223> OTHER INFORMATION: Peptide degradation product derived from prh
      TNFR2:Fc (PRX106)

<400> SEQUENCE: 169

Ser Gln His Thr Gln Pro Thr Pro Glu Pro Ser Thr Ala Pro Ser
1               5                   10                  15

<210> SEQ ID NO 170
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 170

Ser Met Ala Pro Gly Ala Val His Leu Pro Gln Pro Val Ser
1               5                   10

<210> SEQ ID NO 171
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 171

Ala Val His Leu Pro Gln Pro Val Ser Thr Arg
1               5                   10

<210> SEQ ID NO 172
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 172

Gly Gln Pro Arg Glu Pro Gln Val Tyr Thr Leu Pro Pro Ser Arg
1               5                   10                  15

<210> SEQ ID NO 173
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 173

Pro Gly Ala Val His Leu Pro Gln Pro Val Ser Thr Arg
1               5                   10

<210> SEQ ID NO 174
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 174

Thr Leu Met Ile Ser Arg
1               5
```

<210> SEQ ID NO 175
<211> LENGTH: 33
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 175

Lys Asn Gln Val Ser Leu Thr Cys Leu Val Lys Gly Phe Tyr Pro Ser
1               5                   10                  15

Asp Ile Ala Val Glu Trp Glu Ser Asn Gly Gln Pro Glu Asn Asn Tyr
            20                  25                  30

Lys

<210> SEQ ID NO 176
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 176

Leu Arg Glu Tyr Tyr Asp Gln Thr Ala Gln Met Cys
1               5                   10

<210> SEQ ID NO 177
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 177

Ser Met Ala Pro Gly Ala Val His Leu Pro Gln Pro Val
1               5                   10

<210> SEQ ID NO 178
<211> LENGTH: 7
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 178

Leu Pro Ala Pro Ile Glu Lys
1               5

<210> SEQ ID NO 179
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 179

Glu Tyr Tyr Asp Gln Thr Ala Gln Met Cys Cys Ser Lys
1               5                   10

<210> SEQ ID NO 180
<211> LENGTH: 12
<212> TYPE: PRT

```
<213> ORGANISM: Artificial sequence
<220> FEATURE:
<223> OTHER INFORMATION: Peptide degradation product derived from prh
      TNFR2:Fc (PRX106)

<400> SEQUENCE: 180

Asn Trp Val Pro Glu Cys Leu Ser Cys Gly Ser Arg
1               5                   10

<210> SEQ ID NO 181
<211> LENGTH: 12
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 181

Ser Leu Ser Pro Gly Lys Ser Glu Lys Asp Glu Leu
1               5                   10

<210> SEQ ID NO 182
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 182

Ile Cys Thr Cys Arg Pro Gly Trp Tyr Cys Ala Leu Ser Lys
1               5                   10

<210> SEQ ID NO 183
<211> LENGTH: 15
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 183

Ser Met Ala Pro Gly Ala Val His Leu Pro Gln Pro Val Ser Thr
1               5                   10                  15

<210> SEQ ID NO 184
<211> LENGTH: 13
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 184

Glu Tyr Tyr Asp Gln Thr Ala Gln Met Cys Cys Ser Lys
1               5                   10

<210> SEQ ID NO 185
<211> LENGTH: 14
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 185

Ala Ser Met Asp Ala Val Cys Thr Ser Thr Ser Pro Thr Arg
1               5                   10
```

```
<210> SEQ ID NO 186
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 186

Ser Gln His Thr Gln Pro Thr Pro Glu Pro Ser Thr Ala Pro Ser Thr
1               5                   10                  15

Ser

<210> SEQ ID NO 187
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 187

Thr Leu Pro Pro Ser Arg Glu Glu Met Thr Lys
1               5                   10

<210> SEQ ID NO 188
<211> LENGTH: 19
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 188

Ser Gln His Thr Gln Pro Thr Pro Glu Pro Ser Thr Ala Pro Ser Thr
1               5                   10                  15

Ser Phe Leu

<210> SEQ ID NO 189
<211> LENGTH: 6
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 189

Thr Leu Met Ile Ser Arg
1               5

<210> SEQ ID NO 190
<211> LENGTH: 16
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 190

Glu Pro Gln Val Tyr Thr Leu Pro Pro Ser Arg Glu Glu Met Thr Lys
1               5                   10                  15

<210> SEQ ID NO 191
<211> LENGTH: 20
<212> TYPE: PRT
```

<213> ORGANISM: Artificial sequence
<220> FEATURE:
<223> OTHER INFORMATION: Peptide degradation product derived from prh
      TNFR2:Fc (PRX106)

<400> SEQUENCE: 191

Gly Gln Pro Arg Glu Pro Gln Val Tyr Thr Leu Pro Pro Ser Arg Glu
1               5                   10                  15

Glu Met Thr Lys
            20

<210> SEQ ID NO 192
<211> LENGTH: 21
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 192

Thr Pro Glu Val Thr Cys Val Val Val Asp Val Ser His Glu Asp Pro
1               5                   10                  15

Glu Val Lys Phe Asn
            20

<210> SEQ ID NO 193
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 193

Ser Cys Asp Lys Thr His Thr Cys Pro Pro Cys Pro Ala Pro Glu Leu
1               5                   10                  15

Leu Gly

<210> SEQ ID NO 194
<211> LENGTH: 22
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 194

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 195
<211> LENGTH: 17
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 195

Ala Lys Gly Gln Pro Arg Glu Pro Gln Val Tyr Thr Leu Pro Pro Ser
1               5                   10                  15

Arg

<210> SEQ ID NO 196
<211> LENGTH: 13
<212> TYPE: PRT
<213> ORGANISM: Artificial sequence
<220> FEATURE:
<223> OTHER INFORMATION: Peptide degradation product derived from prh
    TNFR2:Fc (PRX106)

<400> SEQUENCE: 196

Leu Arg Glu Tyr Tyr Asp Gln Thr Ala Gln Met Cys Cys
1               5                   10

<210> SEQ ID NO 197
<211> LENGTH: 18
<212> TYPE: PRT
<213> ORGANISM: Artificial sequence
<220> FEATURE:
<223> OTHER INFORMATION: Peptide degradation product derived from prh
    TNFR2:Fc (PRX106)

<400> SEQUENCE: 197

Leu Pro Met Gly Pro Ser Pro Pro Ala Glu Gly Ser Thr Gly Asp Glu
1               5                   10                  15

Pro Lys

<210> SEQ ID NO 198
<211> LENGTH: 16
<212> TYPE: PRT
<213> ORGANISM: Artificial sequence
<220> FEATURE:
<223> OTHER INFORMATION: Peptide degradation product derived from prh
    TNFR2:Fc (PRX106)

<400> SEQUENCE: 198

Ser Cys Ser Val Met His Glu Ala Leu His Asn His Tyr Thr Gln Lys
1               5                   10                  15

<210> SEQ ID NO 199
<211> LENGTH: 14
<212> TYPE: PRT
<213> ORGANISM: Artificial sequence
<220> FEATURE:
<223> OTHER INFORMATION: Peptide degradation product derived from prh
    TNFR2:Fc (PRX106)

<400> SEQUENCE: 199

Phe Asn Trp Tyr Val Asp Gly Val Glu Val His Asn Ala Lys
1               5                   10

<210> SEQ ID NO 200
<211> LENGTH: 17
<212> TYPE: PRT
<213> ORGANISM: Artificial sequence
<220> FEATURE:
<223> OTHER INFORMATION: Peptide degradation product derived from prh
    TNFR2:Fc (PRX106)

<400> SEQUENCE: 200

Pro Met Gly Pro Ser Pro Pro Ala Glu Gly Ser Thr Gly Asp Glu Pro
1               5                   10                  15

Lys

<210> SEQ ID NO 201
<211> LENGTH: 16
<212> TYPE: PRT
<213> ORGANISM: Artificial sequence -continued

```
<220> FEATURE:
<223> OTHER INFORMATION: Peptide degradation product derived from prh
      TNFR2:Fc (PRX106)

<400> SEQUENCE: 201

Ser Met Ala Pro Gly Ala Val His Leu Pro Gln Pro Val Ser Thr Arg
1               5                   10                  15

<210> SEQ ID NO 202
<211> LENGTH: 11
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 202

Ser Met Ala Pro Gly Ala Val His Leu Pro Gln
1               5                   10

<210> SEQ ID NO 203
<211> LENGTH: 18
<212> TYPE: PRT
<213> ORGANISM: Artificial sequence
<220> FEATURE:
<223> OTHER INFORMATION: Peptide degradation product derived from prh
      TNFR2:Fc (PRX106)

<400> SEQUENCE: 203

Leu Pro Met Gly Pro Ser Pro Pro Ala Glu Gly Ser Thr Gly Asp Glu
1               5                   10                  15

Pro Lys

<210> SEQ ID NO 204
<211> LENGTH: 474
<212> TYPE: PRT
<213> ORGANISM: Artificial Sequence
<220> FEATURE:
<223> OTHER INFORMATION: PRX106

<400> SEQUENCE: 204

Ala Leu Pro Ala Gln Val Ala Phe Thr Pro Tyr Ala Pro Glu Pro Gly
1               5                   10                  15

Ser Thr Cys Arg Leu Arg Glu Tyr Tyr Asp Gln Thr Ala Gln Met Cys
                20                  25                  30

Cys Ser Lys Cys Ser Pro Gly Gln His Ala Lys Val Phe Cys Thr Lys
            35                  40                  45

Thr Ser Asp Thr Val Cys Asp Ser Cys Glu Asp Ser Thr Tyr Thr Gln
        50                  55                  60

Leu Trp Asn Trp Val Pro Glu Cys Leu Ser Cys Gly Ser Arg Cys Ser
65                  70                  75                  80

Ser Asp Gln Val Glu Thr Gln Ala Cys Thr Arg Glu Gln Asn Arg Ile
                85                  90                  95

Cys Thr Cys Arg Pro Gly Trp Tyr Cys Ala Leu Ser Lys Gln Glu Gly
            100                 105                 110

Cys Arg Leu Cys Ala Pro Leu Arg Lys Cys Arg Pro Gly Phe Gly Val
        115                 120                 125

Ala Arg Pro Gly Thr Glu Thr Ser Asp Val Val Cys Lys Pro Cys Ala
    130                 135                 140

Pro Gly Thr Phe Ser Asn Thr Thr Ser Ser Thr Asp Ile Cys Arg Pro
145                 150                 155                 160
```

```
His Gln Ile Cys Asn Val Ala Ile Pro Gly Asn Ala Ser Met Asp
            165                 170                 175

Ala Val Cys Thr Ser Thr Ser Pro Thr Arg Ser Met Ala Pro Gly Ala
        180                 185                 190

Val His Leu Pro Gln Pro Val Ser Thr Arg Ser Gln His Thr Gln Pro
        195                 200                 205

Thr Pro Glu Pro Ser Thr Ala Pro Ser Thr Ser Phe Leu Leu Pro Met
    210                 215                 220

Gly Pro Ser Pro Pro Ala Glu Gly Ser Thr Gly Asp Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
                260                 265                 270

Met Ile Ser Arg Thr Pro Glu Val Thr Cys Val Val Val Asp Val Ser
                275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys Ser Glu Lys Asp Glu Leu
465                 470

<210> SEQ ID NO 205
<211> LENGTH: 472
<212> TYPE: PRT
<213> ORGANISM: Artificial Sequence
<220> FEATURE:
<223> OTHER INFORMATION: PRX106

<400> SEQUENCE: 205

Pro Ala Gln Val Ala Phe Thr Pro Tyr Ala Pro Glu Pro Gly Ser Thr
1               5                   10                  15

Cys Arg Leu Arg Glu Tyr Tyr Asp Gln Thr Ala Gln Met Cys Cys Ser
                20                  25                  30

Lys Cys Ser Pro Gly Gln His Ala Lys Val Phe Cys Thr Lys Thr Ser
            35                  40                  45
```

```
Asp Thr Val Cys Asp Ser Cys Glu Asp Ser Thr Tyr Thr Gln Leu Trp
    50              55                  60

Asn Trp Val Pro Glu Cys Leu Ser Cys Gly Ser Arg Cys Ser Ser Asp
 65              70                  75                      80

Gln Val Glu Thr Gln Ala Cys Thr Arg Glu Gln Asn Arg Ile Cys Thr
                85                  90                  95

Cys Arg Pro Gly Trp Tyr Cys Ala Leu Ser Lys Gln Glu Gly Cys Arg
            100                 105             110

Leu Cys Ala Pro Leu Arg Lys Cys Arg Pro Gly Phe Gly Val Ala Arg
        115                 120             125

Pro Gly Thr Glu Thr Ser Asp Val Val Cys Lys Pro Cys Ala Pro Gly
    130                 135             140

Thr Phe Ser Asn Thr Thr Ser Ser Thr Asp Ile Cys Arg Pro His Gln
145             150                 155                     160

Ile Cys Asn Val Val Ala Ile Pro Gly Asn Ala Ser Met Asp Ala Val
                165             170                 175

Cys Thr Ser Thr Ser Pro Thr Arg Ser Met Ala Pro Gly Ala Val His
            180                 185             190

Leu Pro Gln Pro Val Ser Thr Arg Ser Gln His Thr Gln Pro Thr Pro
            195                 200             205

Glu Pro Ser Thr Ala Pro Ser Thr Ser Phe Leu Leu Pro Met Gly Pro
    210                 215             220

Ser Pro Pro Ala Glu Gly Ser Thr Gly Asp Glu Pro Lys Ser Cys Asp
225             230                 235                     240

Lys Thr His Thr Cys Pro Pro Cys Pro Ala Pro Glu Leu Leu Gly Gly
                245             250                 255

Pro Ser Val Phe Leu Phe Pro Pro Lys Pro Lys Asp Thr Leu Met Ile
            260                 265             270

Ser Arg Thr Pro Glu Val Thr Cys Val Val Val Asp Val Ser His Glu
            275                 280             285

Asp Pro Glu Val Lys Phe Asn Trp Tyr Val Asp Gly Val Glu Val His
    290                 295             300

Asn Ala Lys Thr Lys Pro Arg Glu Glu Gln Tyr Asn Ser Thr Tyr Arg
305             310                 315                     320

Val Val Ser Val Leu Thr Val Leu His Gln Asp Trp Leu Asn Gly Lys
                325             330                 335

Glu Tyr Lys Cys Lys Val Ser Asn Lys Ala Leu Pro Ala Pro Ile Glu
            340                 345             350

Lys Thr Ile Ser Lys Ala Lys Gly Gln Pro Arg Glu Pro Gln Val Tyr
            355                 360             365

Thr Leu Pro Pro Ser Arg Glu Glu Met Thr Lys Asn Gln Val Ser Leu
    370                 375             380

Thr Cys Leu Val Lys Gly Phe Tyr Pro Ser Asp Ile Ala Val Glu Trp
385             390                 395                     400

Glu Ser Asn Gly Gln Pro Glu Asn Asn Tyr Lys Thr Thr Pro Pro Val
                405             410                 415

Leu Asp Ser Asp Gly Ser Phe Phe Leu Tyr Ser Lys Leu Thr Val Asp
            420                 425             430

Lys Ser Arg Trp Gln Gln Gly Asn Val Phe Ser Cys Ser Val Met His
            435                 440             445

Glu Ala Leu His Asn His Tyr Thr Gln Lys Ser Leu Ser Leu Ser Pro
    450                 455             460
```

```
Gly Lys Ser Glu Lys Asp Glu Leu
465                 470
```